(12) United States Patent
Love et al.

(10) Patent No.: US 7,138,403 B2
(45) Date of Patent: Nov. 21, 2006

(54) 2,4,5-TRISUBSTITUTED THIAZOLYL DERIVATIVES AND THEIR ANTIINFLAMMATORY ACTIVITY

(75) Inventors: Christopher John Love, Deurne (BE); Jean Pierre Frans Van Wauwe, Beerse (BE); Marc J. De Brabander, Zoersel (BE); Roger Clive Moses, Wadebridge (GB); Mykhalyo Goncharenko, London (CA); Ludwig Paul Cooymans, Beerse (BE); Nele Vandermaesen, Olmen (BE); Gaston Stanislas Marcella Diels, Ravels (BE); Anthony William Sibley, Camelford (GB); Caterina Noula, St. Columb Major (GB)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 10/486,820

(22) PCT Filed: Aug. 9, 2002

(86) PCT No.: PCT/EP02/08956

§ 371 (c)(1),
(2), (4) Date: Feb. 11, 2004

(87) PCT Pub. No.: WO03/015776

PCT Pub. Date: Feb. 27, 2003

(65) Prior Publication Data

US 2004/0254192 A1    Dec. 16, 2004

(30) Foreign Application Priority Data

Aug. 13, 2001 (EP) .................. 01203088

(51) Int. Cl.
*C07D 239/24* (2006.01)
*A61K 31/495* (2006.01)

(52) U.S. Cl. .................. 514/266.2; 544/242; 544/284; 514/365; 548/146

(58) Field of Classification Search .................. 544/242, 544/284; 514/266.2
See application file for complete search history.

(56) References Cited

U.S. PATENT DOCUMENTS

| 3,933,838 | A | * | 1/1976 | Manghisi et al. ............ 548/194 |
| 5,240,929 | A |   | 8/1993 | Connor et al. |
| 6,231,786 | B1 |  | 5/2001 | Wingen et al. |
| 6,531,479 | B1 | * | 3/2003 | Wang et al. .................. 514/275 |

FOREIGN PATENT DOCUMENTS

| DE | 1 959 307 | 11/1969 |
| DE | 258 165 A | 3/1987 |
| EP | 117 082 A2 | 8/1984 |
| GB | 1 189 008 | 4/1970 |
| JP | 3 144 612 A | 12/1992 |
| WO | WO 96/03392 A1 | 2/1996 |
| WO | WO 97/05131 A1 | 2/1997 |
| WO | WO 98/01449 A1 | 1/1998 |
| WO | WO 98/08830 A1 | 3/1998 |
| WO | WO 98/08841 A1 | 3/1998 |
| WO | WO 00/35911 A1 | 6/2000 |
| WO | WO 01/30778 A1 | 5/2001 |
| WO | WO 01/64674 A1 | 9/2001 |
| WO | WO 02/50047 A1 | 6/2002 |
| WO | WO 02/50048 A1 | 6/2002 |
| WO | WO 02/059098 A1 | 8/2002 |
| WO | WO 02/062774 A1 | 8/2002 |

OTHER PUBLICATIONS

Simiti et al, "Synthese und antibakterielle Wirkung von 2-Aryl-4-R-5-glyoxyloyl-thiazolen," Arch. Pharm. (Weinheim) 314, 744-750 (1981).*

Simiti, I. et al., Synthese und antibakterielle Wirkung von 2-Aryl-4-R-5-glyoxyloyl-thiazolen, Arch. Pharm. (Weinheim) 314, pp. 744-750 (1981).*

Benko, A. et al., "4-Methyl-2-[p-nitro-phenyl]-5-diazoacetyl-thiazol, ein neues, sehr stabiles Diazoketon." *Chem. Ber.* 1967, pp. 2184-2187, vol. 100, No. 7+.

Kempter, G. et al., "Thiazolyl- und Pyrrolytchinoline1)²)." *Z. Chem., 9. Jg.*, 1969, pp. 186-187, vol. 5, No. 9.

(Continued)

*Primary Examiner*—Kamal Saeed
*Assistant Examiner*—Susannah L. Chung
(74) *Attorney, Agent, or Firm*—Thomas Dodd

(57) ABSTRACT

This invention concerns the use of a compound of formula (I)

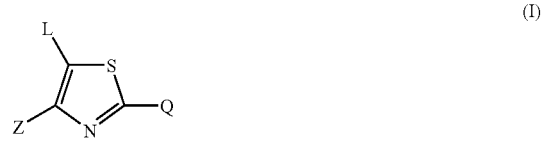

a N-oxide, a pharmaceutically acceptable addition salt, a quaternary amine and a stereochemically isomeric form thereof, wherein Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl or $C_{1-6}$alkyloxy; polyhalo$C_{1-4}$alkyl; $C_{1-4}$alkyloxy; cyano; amino; aminocarbonyl; mono- or di($C_{1-6}$alkyl)aminocarbonyl; $C_{1-6}$alkyloxycarbonyl; $C_{1-6}$alkylcarbonyloxy; $H_2N$—$S(=O)_2$—; mono- or di($C_{1-6}$alkyl)amino-$S(=O)_2$; —$C(=N-R^x)NR^yR^z$; Q is an optionally substituted carbocycle or an optionally substituted heterocycle; L is substituted phenyl or an optionally substituted monocyclic 5 or 6-membered partially saturated or aromatic heterocycle or a bicyclic partially saturated or aromatic heterocycle; aryl is optionally substituted phenyl; for the manufacture of a medicament for the prevention or the treatment of diseases mediated through TNF-α and/or IL-12.

27 Claims, No Drawings

OTHER PUBLICATIONS

Csavassy, G. et al., "Synthese und Umsetzung von 2-Aryly-5-diazoacetyl-4-methyl-thiazolen." *Justus Liebigs Ann. Chem.*, 1974, pp. 1195-1205.

Sawhney, S. N. et al., "Thiazole Derivatives: Part I-Synthesis & Anti-inflammatory Activity of Some 2'-Alkyl/Aryl-2-aryl-4-methyl-4', 5-bithiazolyls & 2'-Amino/Substitutedamino-2-aryl-4-methyl-4',5-bithiazolyls." *Indian J. Chem.*, 1976, pp. 552-555, vol. 14B.

Sarodnick G. et al., "Heterocyclisch Substituierte Thiazole als Thiabendazol-Analoge." *Z. Chem.* 1979, pp. 21-22. vol. 1, No. 19.

Simiti, I, et al., "Synthase Und antibakterielle Wirkung von 2-Aryl-4-R-5-glyxyloyl-thiazolen." *Arch. Pharm.*, 1981, pp. 744-750, vol. 9, No. 314.

Yousif, M. M., "Studies on Tertiary Amine Oxides. LXXIV.') Reactions of Aromatic N-Oxides with 2-Phenyl-2-Thiazolin-4-one in the Presence of Acetic Anhydride." *Chem. Pharm. Bull.*, 1982, pp. 174-179, vol. 30(6).

Burger, K. et al., "Zum Reaktionsverhalten von Trifluormethyl-Gruppen Synthese von 1,3-Azolen aus Trifluormethyl-substituierten Hetero-1,3-dienen." *Chem. Ber.*, 1982, pp. 2494-2507, vol. 115.

Moriya, T. et al., "Synthesis of Ethyl 2-(4-Chlorophenyl)-5-(2-furyl)-4-oxazoleacetate, A Hypolipedmic Agent, and Related Compounds1." *J. Med. Chem.* 1988, pp. 1197-1204, vol. 31, No. 6.

Burger, K., et al., "Uber eine neue Methode zur positionsselektiven Einfuhrung von Trifluormethyl-Gruppen in Heteroaromaten, Teil 2. 'Nucleophile Substitution an 5-fluor-4-trifluormethyl-substituierten 1,3-Azolen." *Synthesis*, 1988, pp. 194-198, vol. 3.

Burger, K., et al., "Zum Cyloadditionsverhalten von 5-Azido-4-trifluormethyl-1, 3-azolen." *Z. Naturforsch, B. Chem. Sci.*, 1990, pp. 1695-1708, vol. 12, No. 45.

PCT International Search Report for PCT Appln. No. PCT/EP02/08956, mailed Aug. 9, 2003 which relates to this corresponding U.S. Appl. filed herewith.

* cited by examiner

2,4,5-TRISUBSTITUTED THIAZOLYL DERIVATIVES AND THEIR ANTIINFLAMMATORY ACTIVITY

CROSS REFERENCE TO RELATED APPLICATIONS

This application is the national stage of Application No. PCT/EP02/08956, filed Aug. 9, 2002, which application claims priority from EP 01203088.8, filed Aug. 13, 2001.

The present invention is concerned with 2,4,5-trisubstituted thiazolyl derivatives having proinflammatory cytokine production inhibiting properties. The invention further relates to methods for their preparation and pharmaceutical compositions comprising them. The invention also relates to the use of 2,4,5-trisubstituted thiazolyl derivatives for the manufacture of a medicament for the prevention or the treatment of diseases mediated through TNF-α and/or IL-12.

WO 00/35911 describes acetal derivatives as TNF-α inhibitors.

WO 96/03392 describes sulphonyl derivatives for treating inflammation.

WO 98/01449 describes pyrimidine fused compounds as antiallergic and antiinflammatory agents.

U.S. Pat. No. 5,240,929 describes 2-heterocyclic-5-hydroxy-1,3-pyrimidines useful as antiinflammatory agents.

Z. Chem., 1969, 9(5), 186–187 describes thiazolyl quinolines as fluorescence indicators.

EP 117,082 describes thiazole derivatives as cardiotonic, blood pressure regulating and anti-ulcer agents.

Chem.Pharm. Bull., 1982, 30(6), 1974–1979 discloses studies on tertiary amine oxides.

WO 97/05131 describes heteroarylcarboxamides as agrochemical and medical fungicides.

JP 91-144612 relates to isoxazoles as disinfectants, antiseptics, anti-inflammatory agents, bactericides, viricides.

Arch.Pharm. 1981, 314(9), 744–750 describes the synthesis and antibacterial effect of 2-aryl-4-R-5 glyoxyl-thiazoles.

Z.Naturforsch. B Chem. Sci. 1990, 45(12), 1695–1708 concerns cycloaddition reactions with 5-azido-4-(trifluoromethyl)-1,3-azoles.

Synthesis 1988, 3, 194–198 describes methods for regioselective introduction of trifluoromethyl groups into heteroarenes.

J.Med.Chem. 1988, 31 (6), 1197–1204 describes the synthesis of oxazole derivatives as hypolipidemic, anticholesteremic and blood platelet aggregation inhibiting agents.

Chem.Ber. 1982, 115(7), 2494–2507 relates to the synthesis of 1,3-azoles. DD 258165 describes quinoxaline derivatives as herbicides and fungicides.

Z.Chem. 1979, 19(1), 21–22 relates to heterocyclic substituted thiazoles as pesticides. Indian J.Chem., Sect. B, 1976, 14B(7), 552–555 concerns the synthesis and antiinflammatory activity of bithiazolyl derivatives.

Justus Liebigs Ann. Chem. 1974, 8, 1195–1205 describes the synthesis of thiazole compounds.

DE 1959307 concerns benzoxazole derivatives as fluorescent whiteners.

GB 1189008 relates to benzoxazole derivatives as fluorescent whiteners.

JP 41012946 describes benzoxazole and benzimidazole derivatives as optical brightening organic fibers.

Chem.Ber. 1967, 100(7), 2184–2187 describes the synthesis of thiazole derivatives. U.S. Pat. No. 6,231,786 describes fluorinated azoles and their use in liquid crystalline mixtures.

WO 01/30778 discloses thiazoles and imidazopyridines for treating TNF and IL-1 mediated diseases.

WO 98/08830 and WO 98/08841 disclose thiazole derivatives having PDE IV inhibiting properties.

WO 01/64674 describes 2,4-disubstituted thiazolyl derivatives as TNF-α and/or IL-12 inhibitors.

The compounds of the present invention are distinguishable from the prior art because of their structure, pharmacological activity, potency or physicochemical characteristics (improved chemical stability, improved solubility).

The present invention relates to the use of a compound for the manufacture of a medicament for the prevention or the treatment of diseases mediated through TNF-α (Tumor Necrosis Factor-alpha) and/or IL-12 (Interleukin 12) wherein the compound is a compound of formula

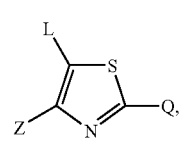

(I)

a N-oxide, a pharmaceutically acceptable addition salt, a quaternary amine and a stereochemically isomeric form thereof, wherein Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminbcarbonyl, $C_{1-6}$alkyloxycarbonyl or $C_{1-6}$alkyloxy; polyhalo$C_{1-4}$alkyl; $C_{1-4}$alkyloxy; cyano; amino; aminocarbonyl; mono- or di($C_{1-6}$alkyl)aminocarbonyl; $C_{1-6}$alkyloxycarbonyl; $C_{1-6}$alkylcarbonyloxy; $H_2N-S(=O)_2-$; mono- or di($C_{1-6}$alkyl)amino-S($=O)_2$; $-C(=N-R^x)NR^yR^z$;

$R^x$ is hydrogen, $C_{1-6}$alkyl, cyano, nitro or $-S(=O)_2-NH_2$;

$R^y$ is hydrogen, $C_{1-6}$alkyl, $C_{2-6}$alkenyl or $C_{2-6}$alkynyl;

$R^z$ is hydrogen or $C_{1-6}$alkyl;

Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhaloC, alkyloxy; polyhalo$C_{1-6}$alkylcarbonyl; $C_{1-4}$alkyl-$S(=O)_n-$ or $R^1HN-S(=O)_n-$, with $R^1$ representing hydrogen, or a radical of formula

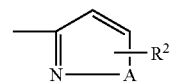

(a-1)

with A being O, S or a bivalent radical of formula —CR²═N— with CR² attached to N of formula (a-1); and R² being hydrogen, C₁₋₆alkyl or C₁₋₆alkyloxy;

or

Q is a radical of formula

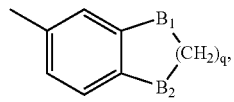

(b-1)

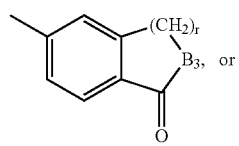

(b-2)

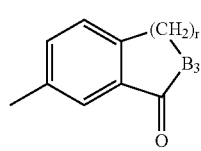

(b-3)

wherein B₁ and B₂ each independently are O, NR³, CH₂ or S, with R³ being hydrogen or C₁₋₄alkyl;

B₃ is O or NR⁴ with R⁴ being hydrogen or C₁₋₄alkyl;

q is an integer with value 1 to 4;

r is an integer with value 1 to 3;

n is an integer with value 1 or 2;

L is phenyl substituted with up to 4 substituents each substituent independently being selected from C₁₋₆alkyloxycarbonyl; C₁₋₆alkylcarbonyloxy; aminocarbonyl; mono- or di(C₁₋₆alkyl)aminocarbonyl; C₁₋₆alkyl-C(═O)—NH—; C₁₋₆alkyloxy-C(═O)—NH—; H₂N—C(═O)—NH—; mono- or di(C₁₋₄alkyl)amino-C(═O)—NH—; Het¹-NH—; Het¹-NH—; —NH—C(═N—Rˣ)NRʸRᶻ; —C(═N—Rˣ)NRʸRᶻ; Het¹; or a radical of formula —X—C₁—Y₁—C₂—Y₂—C₃—Y₃—C₄-Z    (c-1)

wherein

X represents NR5, O, S or a direct bond;

C₁, C₂, C₃ and C₄ each independently represent C₁₋₆alkanediyl, C₂₋₆alkenediyl, C₂₋₆alknediyl or a direct bond;

Y₁, Y₂ and Y₃ each independently represent NR⁵, O, S or a direct bond; Z is hydrogen, halo, cyano, hydroxy, carboxyl, —P(═O)(OH)H, —P(═O)(OH)₂, —P(═O)(OH)CH₃, —P(═O)(OH)(OCH₃), —P(═O)(OH)(OCH₂CH₃), —P(═O)(OH)NH₂, —S(═O)₂H, —S(═O)₂(OH), —S(═O)₂NH, —C(═O)—NH—S(═O)₂—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

R⁵ is hydrogen, C₁₋₆alkyl or —C(═NH)—N(Rᶻ)₂; and wherein from 1 to 3 hydrogen atoms of the C₁₋₆alkyl, C₁₋₆alkanediyl, C₂alkenediyl or C₂₋₆alknediyl groups in the definitions of R⁵ and the radical of formula (c-1) may optionally and each independently be replaced by halo, hydroxy, carboxyl, —P(═O)(OH)H, —P(═O)(OH)₂, —P(═O)(OH)CH₃, —P(═O)(OH)—(OCH₃), —P(═O)(OH)(OCH₂CH₃), —P(═O)(OH)NH₂, —S(═O)₂H, —S(═O)₂(OH), —S(═O)₂NH, —C(═O)—NH—S(═O)₂—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

or

L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from C₁₋₆alkyloxycarbonyl; C₁₋₆alkylcarbonyloxy; aminocarbonyl; mono- or di(C₁₋₆alkyl)aminocarbonyl; C₁₋₆alkyl-C(═O)—NH—; C₁₋₆alkyloxy-C(═O)—NH—; H₂N—C(═O)—NH—; mono- or di(C₁₋₄alkyl)amino-C(═O)—NH—; Het-NH—; Het¹-NH—; —NH—C(═N—Rˣ)NRʸRᶻ; —C(═N—Rˣ)NRʸRᶻ; Het¹; or a radical of formula —X—C₁—Y₁—C₂—Y₂—C₃—Y₃—C₄-Z    (c-1)

wherein

X represents NR⁵, O, S or a direct bond;

C₁, C₂, C₃ and C₄ each independently represent C₁₋₆alkanediyl, C₂₋₆alkenediyl, C₂₋₆alkynediyl or a direct bond;

Y₁, Y₂ and Y₃ each independently represent NR⁵, O, S or a direct bond;

Z is hydrogen, halo, cyano, hydroxy, carboxyl, —P(═O)(OH)H, —P(═O)(OH)₂, —P(═O)(OH)CH₃, —P(═O)(OH)(OCH₃), —P(═O)(OH)(OCH₂CH₃), —P(═O)(OH)NH₂, —S(═O)₂H, —S(═O)₂(OH), —S(═O)₂NH, —C(═O)—NH—S(—O)₂—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

R⁵ is hydrogen, C₁₋₆alkyl or —C(═NH)—N(Rᶻ)₂; and wherein from 1 to 3 hydrogen atoms of the C₁₋₆alkyl, C₁₋₆alkanediyl, C₂₋₆alkenediyl or C₂₋₆alkynediyl groups in the definitions of R⁵ and the radical of formula (c-1) may optionally and each independently be replaced by halo, hydroxy, carboxyl, —P(═O)(OH)H, —P(═O)(OH)₂, —P(═O)(OH)CH₃, —P(═O)(OH)—(OCH₃), —P(═O)(OH)(OCH₂CH₃), —P(═O)(OH)NH₂, —S(═O)₂H, —S(—O)₂(OH), —S(═O)₂NH, —C(═O)—NH—S(═O)₂—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

Het is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, amino, cyano, carboxyl, mono- or di(C₁₋₆alkyl)amino, C₁₋₆alkyl, C₁₋₆alkyl substituted with hydroxy or C₁₋₄alkyloxy or amino or mono- or di(C₁₋₄alkyl)amino, polyhaloC₁₋₆alkyl, C₁₋₆alkyloxy, C₁₋₆alkylthio, C₁₋₆alkyloxycarbonyl, C₁₋₆alkylcarbonyloxy, aminocarbonyl, mono- or di(C₁₋₆alkyl)aminocarbonyl, C₁₋₆alkyl-C(═O)—NH—, C₁₋₆alkyloxy-C(═O)—NH—, H₂N—C(═O)—NH— or mono- or di(C₁₋₄alkyl)amino-C(═O)—NH—;

Het¹ is a saturated 6-membered heterocycle selected from piperidinyl, morpholinyl, thiomorpholinyl, piperazinyl, wherein said saturated 6-membered heterocycle may optionally be substituted with amino or $C_{1-4}$alkyl optionally substituted with aryl;

aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino.

The present invention also relates to a compound of formula (I)

a N-oxide, a pharmaceutically acceptable addition salt, a quaternary amine and a stereochemically isomeric form thereof, wherein Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl or $C_{1-6}$alkyloxy; polyhalo$C_{1-4}$alkyl; $C_{1-4}$alkyloxy; cyano; amino; aminocarbonyl; mono- or di($C_{1-6}$alkyl)aminocarbonyl; $C_{1-6}$alkyloxycarbonyl; $C_{1-6}$alkylcarbonyloxy; $H_2N-S(=O)_2-$; mono- or di($C_{1-6}$alkyl)amino-$S(=O)$; $-C(=N-R^x)NR^yR^z$;

$R^x$ is hydrogen, $C_{1-6}$alkyl, cyano, nitro or $-S(=O)_2-NH_2$;

p0 $R^y$ is hydrogen, $C_{1-6}$alkyl, $C_{1-6}$alkenyl or $C_{1-6}$alkynyl;

$R^z$ is hydrogen or $C_{1-6}$alkyl;

Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl; $C_{1-4}$alkyl-$S(=O)_n-$ or $R^1HN-S(=O)_n-$, with $R^1$ representing hydrogen, or a radical of formula (a-1)

with A being O, S or a bivalent radical of formula $-CR^2=N-$ with $CR^2$ attached to N of formula (a-1); and $R^2$ being hydrogen, $C_{1-6}$alkyl or $C_{1-6}$alkyloxy;

or

Q is a radical of formula (b-1)

(b-2)

(b-3)

wherein $B_1$ and $B_2$ each independently are O, $NR^3$, $CH_2$ or S, with $R^3$ being hydrogen or $C_{1-4}$alkyl;

$B_3$ is O or $NR^4$ with $R^4$ being hydrogen or $C_{1-4}$alkyl;

q is an integer with value 1 to 4;

r is an integer with value 1 to 3;

n is an integer with value 1 or 2;

L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-$C(=O)-NH-$; $C_{1-6}$alkyloxy-$C(=O)-NH-$; $H_2N-C(=O)-NH-$; mono- or di($C_{1-4}$alkyl)amino-$C(=O)-NH-$; Het-NH-; Het$^1$-NH-; $-NH-C(=N-R^x)NR^yR^z$; $-C(=N-R^x)NR^yR^z$; Het$^1$; or a radical of formula $$-X-C_1-Y_1-C_2-Y_2-C_3-Y_3-C_4-Z \quad (c-1)$$

wherein

X represents $NR^5$, O, S or a direct bond; $C_1$, $C_2$, $C_3$ and $C_4$ each independently represent $C_{1-6}$alkanediyl, $C_{2-6}$alkenediyl, $C_{2-6}$alkynediyl or a direct bond; $Y_1$, $Y_2$ and $Y_3$ each independently represent $NR^5$, O, S or a direct bond; Z is hydrogen, halo, cyano, hydroxy, carboxyl, $-P(=O)(OH)H$, $-P(=O)(OH)_2$, $-P(=O)(OH)CH_3$, $-P(=O)(OH)(OCH_3)$, $-P(=O)(OH)(OCH_2CH_3)$, $-P(=O)(OH)NH_2$, $-S(=O)_2H$, $-S(=O)_2(OH)$, $-S(=O)_2NH$, $-C(=O)-NH-S(=O)_2-H$, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl; $R^5$ is hydrogen, $C_{1-6}$alkyl or $-C(=NH)-N(R^z)_2$; and wherein from 1 to 3 hydrogen atoms of the $C_{1-6}$alkyl, $C_{1-6}$alkanediyl, $C_{2-6}$alkenediyl or $C_{2-6}$alknediyl groups in the definitions of $R^5$ and the radical of formula (c-1) may optionally and each independently be replaced by halo, hydroxy, carboxyl, $-P(=O)(OH)H$, $-P(=O)(OH)_2$, $-P(=O)(OH)CH_3$, $-P(=O)(OH)-(OCH_3)$, $-P(=O)(OH)(OCH_2CH_3)$, $-P(=O)(OH)NH_2$, $-S(=O)H$, $-S(=O)_2(OH)$, $-S(=O)_2NH$, $-C(=O)-NH-S(=O)_2-H$, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

Het is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkylthio, $C_{1-6}$alkyloxycarbonyl, $C_{1-6}$alkylcarbonyloxy, aminocarbonyl, mono- or di($C_{1-6}$allyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—;

Het$^1$ is a saturated 6-membered heterocycle selected from piperidinyl, morpholinyl, thiomorpholinyl, piperazinyl, wherein said saturated 6-membered heterocycle may optionally be substituted with amino or $C_{1-4}$alkyl optionally substituted with aryl;

aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino.

provided that when Z is methyl, Q is phenyl or phenyl substituted with halo, methyl or ethyloxy, then L is other than quinoxalinyl;

when Z is methyl, Q is phenyl or phenyl substituted at the para position with methyl, chloro, nitro or methyloxy, then L is other than thiazolyl substituted with methyl or amino;

when Z is trifluoromethyl, Q is 4-methylphenyl, then L is other than 1,2,3-triazolyl mono- or disubstituted with methyloxycarbonyl;

L is other than unsubstituted or substituted benzoxazolyl or unsubstituted or substituted benzimidazolyl;

the compound is other than

| L | Z | Q |
|---|---|---|
| 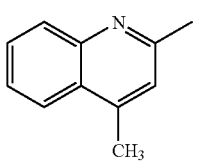 | $CH_3$— | phenyl |
| 3-pyridyl | $CH_3$— | 4-pyridyl |
| 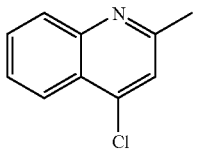 | $CH_3$—C(=O)—O— | phenyl |
| 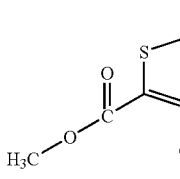 | $CH_3$— | 4-chloro-phenyl |
| 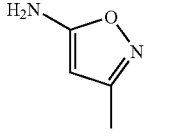 | $CH_3$— | phenyl |
| 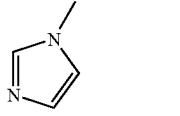 | —$CF_3$ | 4-methyl-phenyl |

| L | Z | Q |
|---|---|---|
| 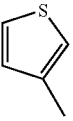 | —CH$_2$—C(=O)—O—CH$_2$CH$_3$ | 4-chloro-phenyl |
| 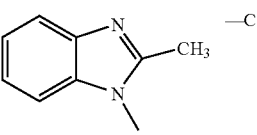 | —CF$_3$ | phenyl |
| 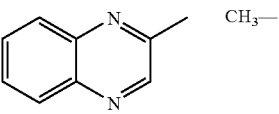 | CH$_3$— | phenyl |
| 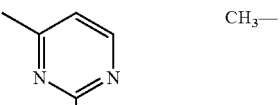 | CH$_3$— | 4-chlorophenyl |
| 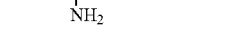 | CH$_3$— | phenyl |
| 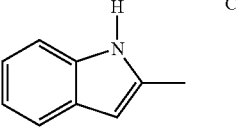 | CH$_3$— | 2-thienyl |
| 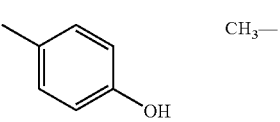 | F— | 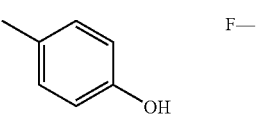 |
| 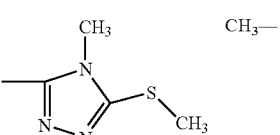 | CH$_3$— | phenyl |
| 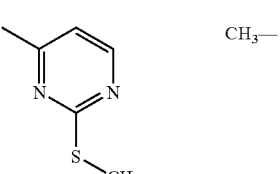 | CH$_3$— | 4-chlorophenyl |

The present invention further relates to a compound of formula

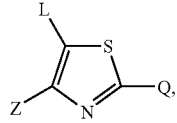
(I)

a N-oxide, a pharmaceutically acceptable addition salt, a quaternary amine and a stereochemically isomeric form thereof, wherein Z is halo; $C_{1-6}$alkyl; $C_{1-6}$alkyl substituted with hydroxy, carboxyl, cyano, amino, mono- or di($C_{1-6}$alykylamino, aminocarbonyl, mono- or di($C_{1-6}$alkyl)aminocarbonyl, $C_{1-6}$alkyloxycarbonyl or $C_{1-6}$alkoxy; polyhalo$C_{1-6}$alkyl; $C_{1-4}$allyloxy; cyano; amino; aminocarbonyl; mono- or di($C_{1-6}$alkyl)aminocarbonyl; $C_{1-6}$alkyloxycarbonyl; $C_{1-6}$alkylcarbonyloxy; $H_2N-S(=)_2-$; mono- or di($C_{1-6}$alkyl)amino-$S(=O)_2$; $-C(=N-R^x)NR^yR^z$;

$R^x$ is hydrogen, $C_{1-6}$alkyl, cyano, nitro or $-S(=O)_2-NH_2$;
$R^y$ is hydrogen, $C_{1-6}$alkyl, $C_{2-6}$alkenyl or $C_{2-6}$alkynyl;
$R^z$ is hydrogen or $C_{1-6}$alkyl;
Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-6}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl; $C_{1-4}$alkyl-$S(=O)_n-$ or $R^1HN-S(=O)_n-$, with $R^1$ representing hydrogen, or a radical of formula

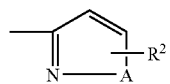
(a-1)

with A being O, S or ambivalent radical of formula $-CR^2=N-$ with $CR^2$ attached to N of formula (a-1); and
$R^2$ being hydrogen, $C_{1-6}$alkyl or $C_{1-6}$alkyloxy;
or
Q is a radical of formula

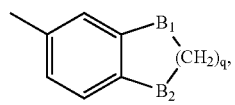
(b-1)

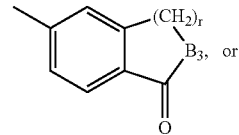
(b-2)

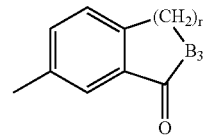
(b-3)

wherein $B_1$ and $B_2$ each independently are O, $NR^3$, $CH_2$ or S, with $R^3$ being hydrogen or $C_{1-4}$alkyl;
$B_3$ is O or $NR^4$ with $R^4$ being hydrogen or $C_{1-4}$alkyl;
q is an integer with value 1 to 4;
r is an integer with value 1 to 3;
n is an integer with value 1 or 2;
L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-$C(=O)-NH-$; $C_{1-6}$alkyloxy-$C(=O)-NH-$; $H_2N-C(=O)-NH-$; mono- or di($C_{1-4}$alkyl)amino-$C(=O)-NH-$; Het-NH-; $Het^1$-NH-; $-NH-C(=N-R^x)NR^yR^z$; $-C(=N-R^x)NR^yR^z$; $Het^1$; or a radical of formula

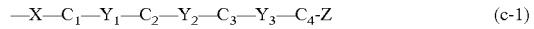
$-X-C_1-Y_1-C_2-Y_2-C_3-Y_3-C_4-Z$ (c-1)

wherein
X represents $NR^5$, O, S or a direct bond; $C_1$, $C_2$, $C_3$ and $C_4$ each independently represent $C_{1-6}$alkanediyl, $C_2$alkenediyl, $C_{2-6}$alkynediyl or a direct bond; $Y_1$, $Y_2$ and $Y_3$ each independently represent $NR^5$, O, S or a direct bond; Z is hydrogen, halo, cyano, hydroxy, carboxyl, $-P(=O)(OH)H$, $-P(=O)(OH)_2$, $-P(=O)(OH)CH_3$, $-P(=O)(OH)(OCH_3)$, $-P(=O)(OH)(OCH_2CH_3)$, $-P(=O)(OH)NH_2$, $-S(=O)_2H$, $-S(=O)_2(OH)$, $-S(=O)_2NH$, $-C(=O)-NH-S(=O)_2-H$, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;
$R^5$ is hydrogen, $C_1$alkyl or $-C(=NH)-N(R^z)_2$; and wherein from 1 to 3 hydrogen atoms of the $C_{1-6}$alkyl, $C_{1-6}$alkanediyl, $C_{2-6}$alkenediyl or $C_{2-6}$alknediyl groups in the definitions of $R^5$ and the radical of formula (c-1) may optionally and each independently be replaced by halo, hydroxy, carboxyl, $-P(=O)(OH)H$, $-P(=O)(OH)_2$, $-P(=O)(OH)CH_3$, $-P(=O)(OH)-(OCH_3)$, $-P(=O)(OH)(OCH_2CH_3)$, $-P(=O)(OH)NH_2$, $-S(=O)H$, $-S(=O)_2(OH)$, $-S(=O)_2NH$, $-C(=O)-NH-S(=O)_2-H$, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;
Het is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkylthio, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—;

$Het^1$ is a saturated 6-membered heterocycle selected from piperidinyl, morpholinyl, thiomorpholinyl, piperazinyl, wherein said saturated 6-membered heterocycle may optionally be substituted with amino or $C_{1-4}$alkyl optionally substituted with aryl;

aryl is phenyl, optionally substituted with up to five substituents each independently selected from halo, hydroxy, $C_{1-6}$alkyl, polyhalo$_{1-6}$alkyl, $C_{1-6}$alkyloxy, $C_{1-6}$alkylthio, cyano, nitro, amino, mono- or di($C_{1-6}$alkyl)amino.

provided that

L is other than substituted phenyl;

when Z is methyl, Q is phenyl or phenyl substituted with halo, $CH_3$ or ethyloxy, then L is other than quinoxalinyl;

when Z is methyl, Q is phenyl or phenyl substituted at the para position with methyl, chloro, nitro or methyloxy, then L is other than thiazolyl substituted with methyl or amino;

the compound is other than

| L | Z | Q |
|---|---|---|
| 3-pyridyl | $CH_3$— | 4-pyridyl |
| [2-methyl-thiazol-5-yl with 4-methyl and 5-C(=O)—O—CH$_3$ ester substituent] | $CH_3$— | 4-chloro-phenyl |
| [5-amino-isoxazol-3-yl] | $CH_3$— | phenyl |
| [3-methyl-thiophen-2-yl] | —$CH_2$—C(=O)—O—$CH_2CH_3$ | 4-chloro-phenyl |
| [3-methyl-quinoxalin-2-yl] | $CH_3$— | phenyl |
| [4-methylphenyl with OH] | F— | [4-methylphenyl]—$(CH_2)_5$—$CH_3$ | for use as a medicine.

As used hereinabove or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl, 2-methylpropyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl, 3-methylpentyl and the like; $C_{1-12}$alkyl as a group or part of a group defines straight or branched chain saturated hydrocarbon radicals having from 1 to 12 carbon atoms such as the groups defined for $C_{1-6}$alkyl and heptyl, octyl, nonyl, decyl, 3-ethylpentyl and the like; $C_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl, 1,6-hexanediyl and the like; $C_{2-6}$alkenyl as a group or part of a group defines straight or branched chain hydrocarbon radicals having from 2 to 6 carbon atoms and having 1 double bond such as ethenyl, propenyl, butenyl, pentenyl, hexenyl, 3-methylbutenyl and the like; $C_{2-6}$alkenediyl as a group or part of a group defines straight or branched chain bivalent hydrocarbon radicals having from 2 to 6 carbon atoms and having 1 double bond such as ethenediyl, 2-butene-1,4-diyl and the like; $C_{2-6}$alkynyl as a group or part of a group defines straight or branched chain hydrocarbon radicals having from 2 to 6 carbon atoms and having 1 triple bond such as ethynyl, propynyl, butynyl, pentynyl, hexynyl, 3-methylbutynyl and the like; $C_{2-6}$alkynediyl as a group or part of a group defines straight or branched chain bivalent hydrocarbon radicals having from 2 to 6 carbon atoms and having 1 triple bond such as ethynediyl, 3-pentyne-1,5-diyl and the like; $C_{3-6}$cycloalkyl is generic to cyclopropyl, cyclobutyl, cyclopentyl and cyclohexyl; a monocyclic or bicyclic partially saturated heterocycle represents a ring system consisting of 1 or 2 rings and comprising at least one heteroatom selected from O, N or S, and at least one double bond provided that the ring system is not an aromatic system; a monocyclic or bicyclic aromatic heterocycle represents an aromatic ring system consisting of 1 or 2 rings and comprising at least one heteroatom selected from O, N or S; the term aromatic is well known to a person skilled in the art and designates cyclically conjugated systems of 4n'+2 electrons, that is with 6, 10, 14 etc. π-electrons (rule of Hückel).

The L or Q radical as described above for the compounds of formula (I) may be attached to the remainder of the molecule of formula (I) through any ring carbon or heteroatom as appropriate. For example, when Q is pyridyl, it may be 2-pyridyl, 3-pyridyl or 4-pyridyl.

Lines drawn into ring systems indicate that the bond may be attached to any suitable ring atom. When the ring system is a bicyclic ring system, the bond may be attached to any suitable ring atom of either of the two rings.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-6}$alkyl, they may be the same or different.

When any variable occurs more than one time in any constituent, each definition is independent.

Whenever used hereinbefore or hereinafter that substituents can be selected each independently out of a list of numerous definitions, such as for example the substituents of L or Q, all possible combinations are intended which are chemically possible and which lead to chemically stable molecules. When ring systems are attached to the remainder of the molecule via a linker, such as for example Het$^1$-NH—, all possible combinations of ring system and linker are intended which are chemically possible and which lead to chemically stable molecules.

When several consecutive substituents in the radical of formula (c-1) represent a direct bond, this has to be interpreted as one single direct bond. For instance, when X represents a direct bond, $C_1$ represents $CH_2$, $Y_1$, $C_2$, $Y_2$; $C_3$, $Y_3$ and $C_4$ represent a direct bond and Z represents hydrogen, then said radical of formula (c-1) represents methyl ($CH_3$).

It will be appreciated that some of the compounds of formula (1) and their N-oxides, addition salts, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of formula (I) and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (1) and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic,.pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like.

Conversely the salt form can be converted by treatment with acid into the free acid form.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of formula (I) wherein one or several tertiary nitrogen atoms are oxidized to the so-called N-oxide.

Some of the compounds of formula (I) may also exist in their tautomeric form. Such forms although not explicitly indicated in the above formula are intended to be included within the scope of the present invention.

Particular examples of monocyclic or bicyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic or bicyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl.

An interesting embodiment of the present invention concerns the use of those compounds of formula (I) wherein Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyl-S(=O)$_n$— or $R^1HN$—S(=O)$_n$—; or Q is a radical of formula

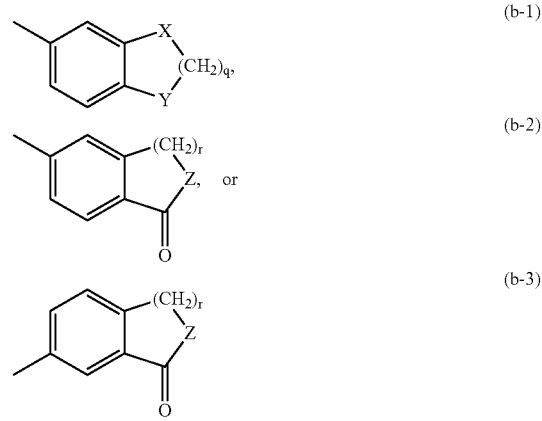

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3;
Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy; polyhalo$C_{1-4}$alkyl; cyano; amino; aminocarbonyl;
mono- or di($C_{1-6}$alkyl)aminocarbonyl; $C_{1-6}$alkyloxycarbonyl; $C_{1-6}$alkylcarbonyloxy;
aminoS(=O)$_2$—; mono- or di($C_{1-6}$alkyl)aminoS(=O)$_2$; —C(=N—$R^x$)$NR^yR^z$;

L is phenyl, substituted with up to 4 substituents each independently being selected from halo, hydroxy, mercapto, amino, cyano, carboxyl, mono- or di($C_{1-6}$alkyl) amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-4}$alkyl-C(=O)—NH—, $C_{1-6}$alkyloxy-C(=O)—NH—, $H_2N$—C(=O)—NH—, mono- or di($C_{1-4}$alkyl)amino-C(=O)—NH— or Het-NH—, —C(=N—$R^x$)$NR^yR^z$;or L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, mercapto, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkylthio, $C_{1-6}$alkyloxycarbonyl, $C_{1-6}$alkylcarbonyloxy, aminocarbonyl, mono- or di($C_{1-6}$alkyl)aminocarbonyl, $C_{1-4}$alkyl-C(=O)—NH—, $C_{1-6}$alkyloxy-C(=O)—NH—, $H_2N$—C(=O)—NH—, mono- or di($C_{1-4}$alkyl)amino-C(=O)—NH— or Het-NH—, —C(=N—$R^x$)$NR^yR^z$.

Another interesting embodiment of the present invention concerns those compounds of formula (I) wherein Q is $C_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyl-S(=O)$_n$— or $R^1$HN—S(=O)$_n$—;

or
Q is a radical of formula

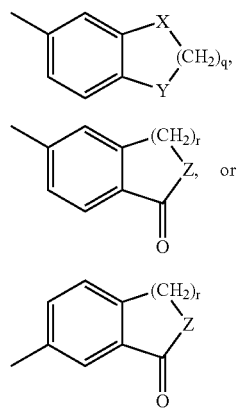

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3;

Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy; polyhalo$C_{1-4}$alkyl; cyano; amino; aminocarbonyl; mono- or di($C_{1-6}$alkyl)aminocarbonyl; $C_{1-6}$alkyloxycarbonyl; $C_{1-6}$alkylcarbonyloxy; aminoS(=O)$_2$—; mono- or di($C_{1-6}$alkyl)aminoS(=O)$_2$; —C(=N—$R^x$)$NR^yR^z$;

L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, mercapto, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-6}$alkyl)amino, polyhalo$C_{1-6}$alkyl, $C_{1-6}$alkyloxy, $C_{1-6}$alkylthio, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH—, mono- or di($C_{1-4}$alkyl)amino-C(=O)—NH— or Het-NH—, —C(=N—$R^x$)$NR^yR^z$.

A further interesting embodiment of the present invention concerns the use of those compounds of formula (I) wherein L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_1$alkyloxy-C(=O)—NH—; $H_2N$—C(=O)—NH—; mono- or di($C_{1-4}$alkyl)amino-C(=O)—NH—; Het-NH—; $Het^1$-NH—; —NH—C(=N—$R^x$)$NR^yR^z$; —C(=N—$R^x$)$NR^yR^z$; $Het^1$; or a radical of formula —X—$C_1$—$Y_1$—$C_2$—$Y_2$—$C_3$—$Y_3$—$C_4$-Z (c-1).

Also an interesting embodiment of the present invention concerns those compounds of formula (I) wherein one or, wherever possible, more of the following restrictions apply:
a) Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)-amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl or $C_{1-4}$alkyl-S(=O)$_n$—; or Q is pyridyl substituted with up to three substituents each independently selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl or $C_{1-4}$alkyl-S(=O)$_n$—;

b) Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_1$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo $C_{1-6}$alkylcarbonyl; $C_{1-4}$alkyl-S(=O)$_n$—;

c) Q is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl;

C$_{1-6}$alkyloxycarbonyl; arylC$_{1-6}$alkyloxy; aryloxy; polyhaloC$_{1-6}$alkyl; polyhaloC$_{1-6}$alkyloxy; polyhaloC$_{1-6}$alkylcarbonyl; C$_{1-4}$alkyl-S(=O)$_n$—;

d) Q is C$_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; cyano; carboxyl; azido; amino; mono- or di(C$_{1-6}$alkyl)amino; C$_{1-6}$alkylcarbonylamino; C$_{1-6}$alkyl; C$_{2-6}$alkenyl; C$_{2-6}$alkynyl; C$_{3-6}$cycloalkyl; C$_{1-6}$alkyl substituted with hydroxy, C$_{1-6}$alkyloxy, amino, mono- or di(C$_{1-4}$alkyl)amino; C$_{1-6}$alkyloxy; C$_{1-6}$alkylthio; C$_{1-6}$alkylcarbonyl; C$_{1-6}$alkyloxycarbonyl; arylC$_{1-6}$alkyloxy; aryloxy; polyhaloC$_{1-6}$alkyl; polyhaloC$_{1-6}$alkyloxy; polyhaloC$_{1-6}$alkylcarbonyl; C$_{1-4}$alkyl-S(=O)$_n$—;

e) Q is C$_{3-6}$cycoalkyl, furanyl, thienyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di(C$_{1-6}$alkyl)-amino; C$_{1-6}$alkylcarbonylamino; C$_{1-6}$alkyl; C$_{2-6}$alkenyl; C$_{2-6}$alkynyl; C$_{3-6}$cycloalkyl; C$_{1-6}$alkyl substituted with hydroxy, C$_{1-6}$alkyloxy, amino, mono- or di(C$_{1-4}$alkyl)amino; C$_{1-6}$alkyloxy; C$_{1-6}$alkylthio; C$_{1-6}$alkylcarbonyl; C$_{1-6}$alkyloxycarbonyl; arylC$_{1-6}$alkyloxy; aryloxy; polyhaloC$_{1-6}$alkyl; polyhaloC$_{1-6}$alkyloxy; polyhaloC$_{1-6}$alkylcarbonyl; C$_{1-4}$alkyl-S(=O)$_n$— or R$^1$HN—S(=O)$_n$—;

f) L is furanyl, pyrrolyl, oxazolyl, imidazolyl, pyrazolyl, isothiazolyl, oxadiazolyl, triazolyl, thiadiazolyl, a 5-membered partially saturated heterocycle, a 6-membered partially saturated or aromatic heterocycle or a bicyclic partially saturated or aromatic heterocycle wherein each of the aforesaid ring systems may optionally be substituted with up to 3 substituents, each substituent independently being selected from C$_{1-6}$alkyloxycarbonyl; C$_{1-6}$alkylcarbonyloxy; aminocarbonyl; mono- or di(C$_{1-6}$alkyl)aminocarbonyl; C$_{1-6}$alkyl-C(=O)—NH—; C$_{1-6}$alkyloxy-C(=O)NH—; H$_2$N—C(=O)NH—; mono- or di(C$_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z (c-1); provided L is other than optionally substituted quinoxalinyl;

g) L is a 6-membered partially saturated or aromatic heterocycle wherein each of said ring systems may optionally be substituted with up to 3 substituents, each substituent independently being selected from C$_{1-6}$alkyloxycarbonyl; C$_{1-6}$alkylcarbonyloxy; aminocarbonyl; mono- or di(C$_{1-6}$alkyl)aminocarbonyl; C$_{1-6}$alkyl-C(=O)—NH—; C$_{1-6}$alkyloxy-C(=O)—NH—; H$_2$N—C(=O)—NH—; mono- or di(C$_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z (c-1);

h) L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from C$_{1-6}$alkyloxycarbonyl; C$_{1-6}$alkylcarbonyloxy; aminocarbonyl; mono- or di(C$_{1-6}$alkyl)aminocarbonyl; C$_{1-6}$alkyl-C(=O)—NH—; C$_{1-6}$alkyloxy-C(=O)—NH—; H$_2$N—C(=O)—NH—; mono- or di(C$_{1-4}$alkyl)amino-C(=O)—NH—; —NH—C(=N—R$^x$)NR$^y$R$^z$; —C(=N—R$^x$)NR$^y$R$^z$; Het$^1$; or a radical of formula —X—C$_1$—Y$_2$—C$_2$—Y$_2$—C$_3$—Y$_3$—C$_4$-Z (c-1);

i) L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from a radical of formula —X—C$_1$—Y$_1$—C$_2$—Y$_2$—C$_3$—Y$_3$—C$_4$-Z (c-1);

j) L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from a radical of formula —X—C$_1$—Y$_1$—C$_2$—Y$_2$—C$_3$—Y$_3$—C$_4$-Z (c-1) provided said radical does not represent hydroxy;

k) L is a monocyclic 5 or 6-membered partially saturated or aromatic heterocycle or a bicyclic partially saturated or aromatic heterocycle wherein each of said ring systems may optionally be substituted with 1 or 2 substituents, each of said two substituent independently being selected from C$_{1-6}$alkyloxycarbonyl; C$_{1-6}$alkylcarbonyloxy; aminocarbonyl; mono- or di(C$_{1-6}$alkyl)aminocarbonyl; C$_{1-6}$alkyl-C(=O)—NH—; C$_{1-6}$alkyloxy-C(=O)—NH—; H$_2$N—C(=O)—NH—; mono- or di(C$_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z (c-1);

l) L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo; hydroxy; mercapto; amino; cyano; carboxyl; mono- or di(C$_{1-12}$alkyl)amino optionally being substituted with one, two or three substituents each independently being selected from hydroxy, amino, mono- or di(C$_{1-4}$alkyl)amino, C$_{1-4}$alkyloxy, C$_{1-4}$alkyloxyC$_{1-4}$alkyloxy, aminoC$_{1-4}$alkyloxy, aminoC$_{1-4}$alkyloxyC$_{1-4}$alkyloxy, mono- or di(C$_{1-4}$alkyl)aminoC$_{1-4}$alkyloxy, mono- or di(C$_{1-4}$alkyl)aminoC$_{1-4}$alkyloxyC$_{1-4}$alkyloxy; C$_{1-6}$alkyl; C$_{1-6}$alkyl substituted with hydroxy, C$_{1-4}$alkyloxy, amino or mono- or di(C$_{1-4}$alkyl)amino; polyhaloC$_{1-6}$alkyl; C$_{1-6}$alkyloxy; C$_{1-6}$alkylthio; C$_{1-6}$alkyloxycarbonyl; C$_{1-6}$alkylcarbonyloxy; aminocarbonyl; mono- or di(C$_{1-6}$alkyl)aminocarbonyl; C$_{1-6}$alkyl-C(=O)—NH—; C$_{1-6}$alkyloxy-C(=O)—NH—; H$_2$N—C(=O)—NH—; mono- or di(C$_1$alkyl)amino-C(=O)—NH—; Het-NH—; Het$^1$-NH—; —NH—C(=N—R$^x$)NR$^y$R$^z$; —C(=N—R$^x$)NR$^y$R$^z$ r Het$^1$;

m) Z is halo; C$_{1-6}$alkyl; C$_{1-6}$alkyl substituted with hydroxy, carboxyl, cyano, amino, mono- or di(C$_{1-6}$alkyl)amino, aminocarbonyl, mono- or di(C$_{1-6}$alkyl)aminocarbonyl, C$_{1-6}$alkyloxycarbonyl or C$_{1-6}$alkyloxy; polyhaloC$_{1-4}$alkyl; cyano; aminocarbonyl; mono- or di(C$_{1-6}$alkyl)aminocarbonyl; C$_{1-6}$alkyloxycarbonyl; C$_{1-6}$alkylcarbonyloxy; H$_2$N—S(=O)$_2$—; mono- or di(C$_{1-6}$alkyl)aminoS(=O)$_2$; —C(=N—R$^x$)NR$^y$R$^z$.

Also an interesting embodiment of the present invention concerns those compounds of formula (I) wherein L is a substituted aromatic 6-membered heterocycle, in particular substituted pyrimidinyl or substituted triazinyl, more in particular substituted pyrimidin-4-yl, even more in particular pyrimidin-4-yl substituted with 1 or 2 substituents, said substituents preferably being selected from amino, amino$C_{1-6}$alkylamino, hydroxy$C_{1-6}$alkylamino (e.g. 3-hydroxypropylamino), carboxy$C_{1-6}$alkylamino (e.g. 2-carboxyethylamino) or halo (e.g. fluoro).

A further interesting embodiment of the present invention concerns those compounds of formula (I) wherein Q is phenyl; phenyl substituted with one of two substituents selected from halo, polyhalo$C_{1-6}$alkyl; pyridyl; Z is $C_{1-6}$alkyl or halo; L is pyrimidinyl, pyrazolyl or triazolyl, each of said three rings being optionally substituted with one or two substituents selected from halo, amino, $C_{1-6}$alkylcarbonylamino, $C_{1-6}$alkylamino, $C_{1-6}$alkylthio, Het-NH—.

Also a preferred embodiment of the present invention concerns those compounds of formula (I) wherein Q is phenyl substituted with polyhalo$C_{1-6}$alkyl, in particular trifluoromethyl.

Also preferred are those compounds of formula (I) wherein Z is halo or $C_{1-6}$alkyl, in particular chloro or methyl.

Also a preferred embodiment of the present invention concerns those compounds of formula (I) wherein Q is phenyl, pyridyl, pyrrolyl, pyrazolyl or thienyl, wherein each of said ring systems may optionally be substituted with one or two substituents each independently being selected from halo or polyhalo$C_{1-6}$alkyl; Z is $C_{1-6}$alkyl, halo, $C_{1-6}$alkyloxy, aminocarbonyl; L is pyrimidinyl, pyrazolyl, triazolyl or triazinyl, wherein each of said ring systems may optionally be substituted with one or two substituents each independently being selected from amino, $C_{1-6}$alkylcarbonylamino, halo, Het-NH—, hydroxy, $C_{1-6}$alkylthio, $C_{1-6}$alkyloxy, $C_{1-6}$alkyl, $C_{1-12}$alkylamino, mono- or di(hydroxy$C_{1-12}$alkyl)amino wherein $C_{1-12}$alkyl may further optionally be substituted with hydroxy, Het$^1$, aminocarbonyl, cyano, amino$C_{1-12}$alkylamino, hydroxy$C_{1-12}$alkyloxy, —NH—C(=NH)—NH$_2$, carboxy$C_{1-12}$alkylamino or amino$C_{1-6}$alkyloxy$C_{1-6}$alkyloxy$C_{1-6}$alkylamino.

Still a further interesting embodiment of the present invention concerns those compounds of formula (I) wherein Q is phenyl; phenyl substituted with one or two substituents selected from chloro, fluoro, trifluoromethyl; 2-pyridyl or 3-pyridyl; Z is methyl; L is 2-amino-pyrimidin-4-yl, 2-methylcarbonylamino-pyrimidin-4-yl, 2-methylamino-pyrimidin-4-yl, 2-methylthio-pyrimidin-4-yl, 2-[(4-methyl-2-thiazolyl)amino]-pyrimidin-4-yl, 2-amino-5-bromo-pyrimidin-4-yl, 2-amino-5-chloro-pyrimidin-4-yl, 4-pyrimidinyl, 3-pyrazolyl, 2-methylthio-1-methyl-1,3,4-triazol-5-yl.

Another interesting embodiment of the present invention concerns those compounds of formula (I) wherein Q is pyrrolyl; pyrazolyl; thienyl; phenyl; phenyl substituted with one or two substituents selected from chloro, fluoro, methyl, trifluoromethyl; 2-pyridyl; 2-pyridyl substituted with chloro, fluoro or trifluoromethyl; 3-pyridyl; Z is methyl, chloro, methoxy or aminocarbonyl; L is 2-amino-pyrimidin-4-yl, 2-methylcarbonylamino-pyrimidin-4-yl, 2-methylamino-pyrimidin-4-yl, 2-methylthio-pyrimidin-4-yl, 2-[(4-methyl-2-thiazolyl)amino]-pyrimidin-4-yl, 2-amino-5-bromo-pyrimidin-4-yl, 2-amino-5-chloro-pyrimidin-4-yl, 2-amino-5-fluoro-pyrimidin-4-yl, 2-piperazinyl-pyrimidin-4-yl, 2-(4-methylpiperazinyl)-pyrimidin-4-yl, 2-(2-amino)ethylamino-pyrimidin-4-yl, 2-(3-amino)propylamino-pyrimidin-4-yl, 2-(6-amino)hexylamino-pyrimidin-4-yl, 2-(7-amino)heptylamino-pyrimidin-4-yl, 2-(8-amino)octylamino-pyrimidin-4-yl, 2-hydroxylamino-pyrimidin-4yl, 2-(2-hydroxy-3-hydroxy)propylamino-pyrimidin-4-yl, 2-guanidino-pyrimidin-4-yl, 2morpholin4yl)-pyrimidin-4-yl, 2-(di(2-hydroxy)ethyl)amino-pyrimidin-4yl, 2-(1-methyl)piperidin-4-yl-pyrimidin-4-yl, 2-(1-benzyl)piperidin-4-yl-pyrimidinyl, 2-[(1-hydroxymethyl-2-hydroxy)ethylamino]-pyrimidinyl, 2-methyl-pyrimidinyl, 2-aminocarbonyl-pyrimidin-4-yl, 2-cyano-pyrimidin-4-yl, 2-(piperidin-1-yl)-pyrimidin-4-yl, 2-methylamino-pyrimidin-4-yl, 4-pyrimidinyl, 3-pyrazolyl, 2-methylthio-1-methyl-1,3,4-triazol-5-yl, 2-amino-1,3,5-triazin-4-yl, 2-methoxy-pyrimidin-4-yl, 2-(2-carboxy)ethylamino-pyrimidin-4yl, 2-carboxymethylamino-pyrimidin-4-yl, 2-(2-hydroxy)ethyloxy-pyrimidinyl, 6-hydroxy-2-amino-pyrimidin-4-yl, 2-(2-amino)ethyloxyethyloxyethyl-pyrimidin-4-yl.

Most preferred compounds are compounds 9 (see Table 3), 34 (see Table 2), 58 (see Table 2) and 84 (see Table 3).

In general, compounds of formula (I) wherein L is 4-pyrimidinyl substituted with R$^a$ in position 2, wherein R$^1$ represents hydrogen, amino, optionally substituted $C_{1-6}$alkyl, optionally substituted mono- or di($C_{1-12}$alkyl)amino, Het-NH— or Het$^1$, said compounds being represented by formula (I-a), can be prepared by reacting an intermediate of formula (II) with an intermediate of formula (II) or a suitable salt thereof, such as for example formamidine acetate, guanidine hydrochloride, guanidine carbonate (2:1), guanidine sulphate, guanidine hemisulphate, N-(3-hydroxypropyl)guanidine hemisulphate, 1-piperazinecarboximidamide sulfate (2:1) and the like, in the presence of a suitable solvent, such as for example N,N-dimethylformamide, dimethylsulphoxide, an alcohol, such as for example ethanol, 2-ethoxyethanol, 2-methoxyethanol and the like, a suitable base, e.g. sodium methanolate (sodium methoxide), sodium ethanolate (sodium ethoxide), sodium hydride and the like. Sodium in the presence of a suitable alcohol may also be used. The reaction may be performed at elevated temperature.

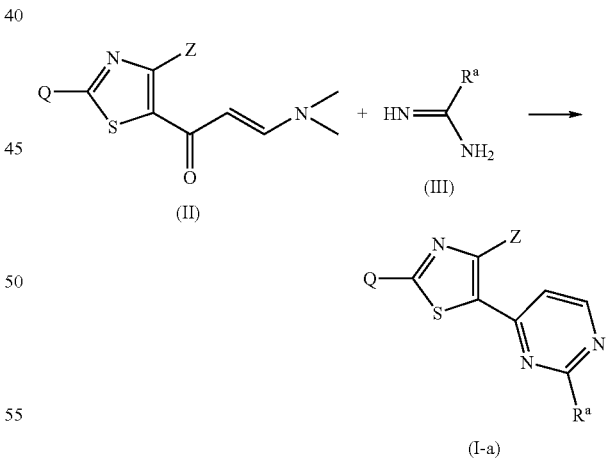

Compounds of formula (I-a) wherein Z represents aminocarbonyl, said compounds being represented by formula (I-a-1), can be prepared by reacting an intermediate of formula (II') with an intermediate of formula (I or a suitable salt thereof, such as for example formamidine acetate, guanidine hydrochloride, guanidine carbonate (2:1), guanidine sulphate, guanidine hemisulphate, N-(3-hydroxypropyl)guanidine hemisulphate, 1-piperaainecarboximidamide sulfate (2:1) and the like, in the presence of a suitable solvent, such as for example N,N-dimethylformamide, dimethylsulphoxide, an alcohol, such as for example ethanol, 2-ethoxyethanol, 2-methoxyethanol and the like, a suitable base, e.g. sodium methanolate (sodium methoxide), sodium hydride and the like. Sodium in the presence of a suitable alcohol may also be used. The reaction may be performed at elevated temperature.

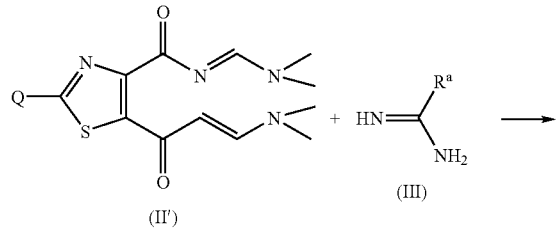

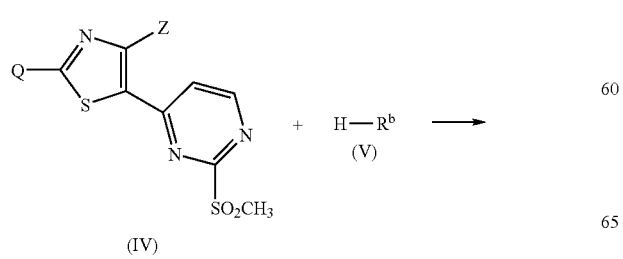

Compounds of formula (I) wherein L is 4-pyrimidinyl substituted with $R^b$ in position 2, wherein $R^b$ represents —$NH_2$, $Het^1$-NH—; $Het^1$; —NH—C(=NH)—N($R^2$)$_2$; $C_{1-12}$alkyloxy optionally substituted with one, two or three hydroxy groups; optionally substituted mono- or di($C_{1-12}$allyl)amino, in particular unsubstituted mono- or di($C_{1-12}$alkyl)amino or mono- or di($C_{1-12}$alkyl)amino wherein $C_{1-12}$alkyl is substituted with one, two or three substituents selected from hydroxy, carboxyl, amino, amino$C_{1-4}$alkyloxy$C_{1-4}$alkyloxy, said compounds being represented by formula (I-b), can be prepared by reacting an intermediate of formula (IV) with an intermediate of formula (V) optionally at elevated temperature and optionally in the presence of a suitable solvent, such as for example N,N-dimethylformamide, dimethylsulphoxide, tetrahydrofuran, an alcohol, e.g. 2-propanol, methanol, methanol/sodium methoxide and the like, and optionally in the presence of a suitable base, such as for example disodium carbonate, in order to form the corresponding salt wherever possible, or a suitable acid, such as for example hydrochloric acid or acetic acid and the like, and optionally in the presence of sodium hydride, for instance when H—$R^b$ represents hydroxy$C_{1-12}$alkyloxy, and optionally under pressure.

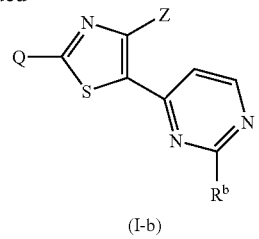

An analogous reaction can be performed to convert an intermediate of formula (IV') into a compound of formula (I'-b).

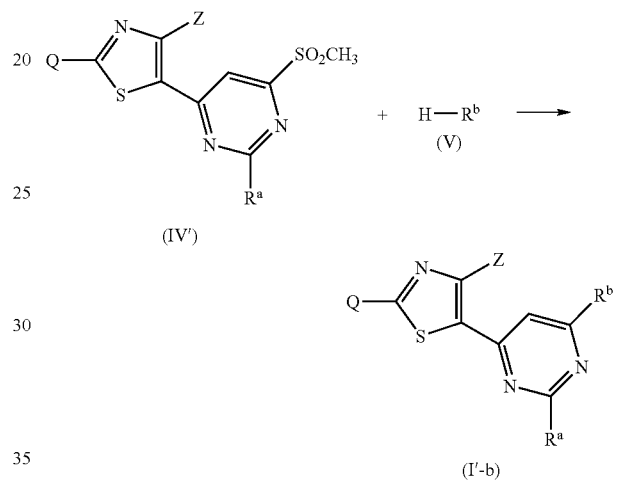

Compounds of formula (I) wherein L is 4-pyrimidinyl substituted with cyano in position 2, said compounds being represented by formula (I-c), can be prepared by reacting an intermediate of formula (IV) with a suitable cyanide salt, such as for example potassium cyanide, in the presence of a suitable solvent, such as for example N,N-dimethylformamide. The reaction may be performed at elevated temperature.

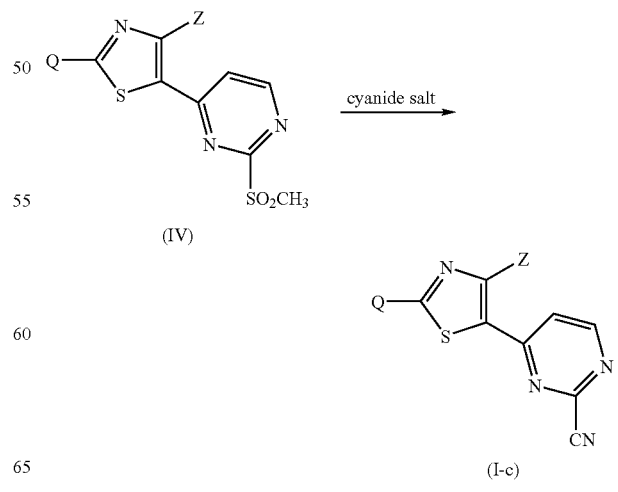

Compounds of formula (I) wherein L is 4-pyrimidinyl substituted with hydroxy in position 2, said compounds being represented by formula (I-d), may be prepared by reacting an intermediate of formula (IV) with a suitable hydroxide base, such as for example sodium hydroxide, in the presence of a suitable solvent, such as for example water, tetrahydrofuran.

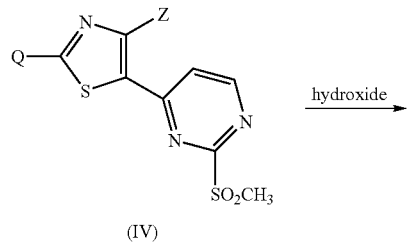

Compounds of formula (I) wherein L is 4-pyrimidinyl substituted with $CH_3$—S— in position 2, said compounds being represented by formula (I-e), can be prepared by reacting an intermediate of formula (II) with thiourea in the presence of a suitable solvent, such as for example an alcohol, e.g. ethanol and the like, a suitable alcoholate, e.g. sodium ethanolate (sodium ethoxide) and the like, dimethyl sulphate, and a suitable base, such as for example sodium hydroxide.

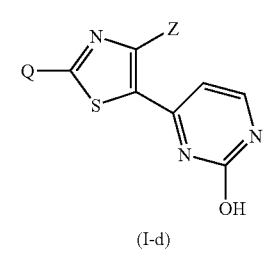

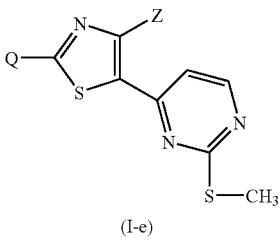

Compounds of formula (I) wherein L is 4-pyrimidinyl substituted with $R^a$ in position 2 and $CH_3$—S— in position 6, said compounds being represented by formula (I'-e), can be prepared by reacting an intermediate of formula (XXXV) with an intermediate of formula (III) in the presence of a suitable solvent, such as for example N,N-dimethylformamide. The reaction may be performed at elevated temperature.

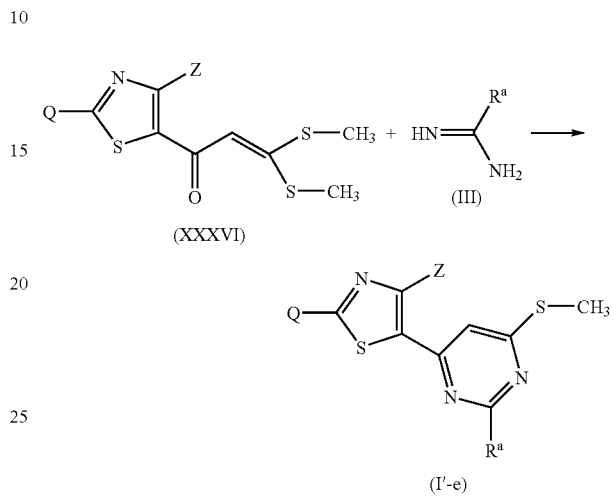

Compounds of formula (I) wherein L is 3-pyrazolyl, said compounds being represented by formula (I-f), can be prepared by reacting an intermediate of formula (II) with hydrazine monohydrate in the presence of a suitable acid, such as for example acetic acid.

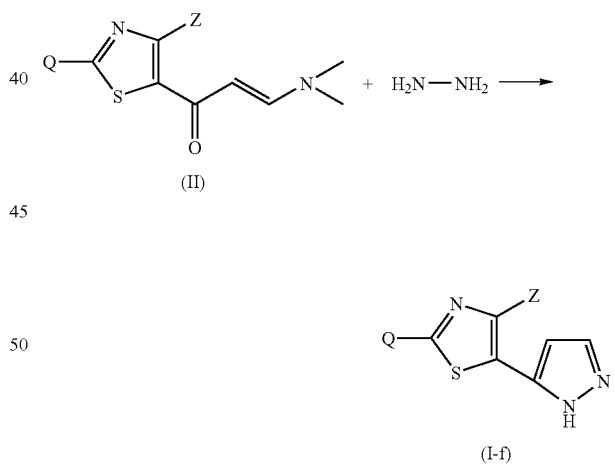

Compounds of formula (I) wherein L is triazolyl substituted with mercapto, said compounds being represented by formula (I-g), can be prepared by reacting an intermediate of formula (VII) with an intermediate of formula (VIII) wherein $R^c$ represents hydrogen or $C_{1-6}$alkyl, in the presence of a suitable base, such as for example 1,8-diazabicyclo[5,4,0]undec-7-ene, and a suitable solvent, such as for example an alcohol, e.g. butanol.

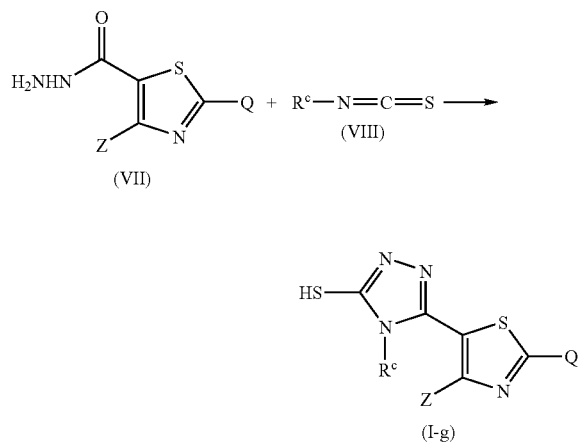

(VII) + (VIII) →

(I-g)

Compounds of formula (I) wherein L is 4-pyrimidinyl substituted with $R^a$ in position 2 and substituted with hydroxy in position 6, said compounds being represented by formula (I-h), can be prepared by reacting an intermediate of formula (VI) with an intermediate of formula (III) or a suitable salt thereof, such as for example formamidine acetate, guanidine hydrochloride, guanidine carbonate (2:1), guanidine sulphate, guanidine hemisulphate, N-(3-hydroxypropyl)guanidine hemisulphate, 1-piperazinecarboximidamide sulfate (2:1) and the like, in the presence of a suitable solvent, such as for example 2-ethoxyethanol/sodium methoxide. The reaction may be performed at elevated temperature.

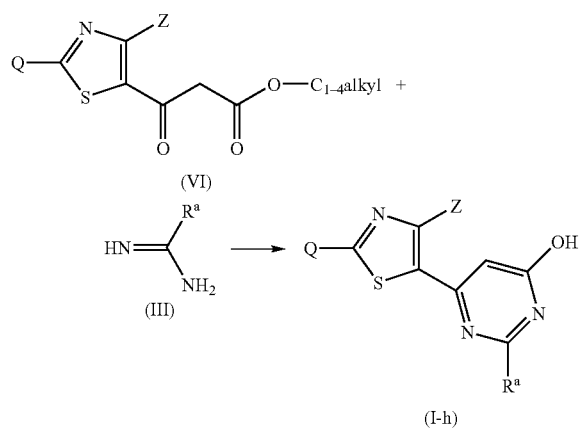

(I-h)

Compounds of formula (I) wherein L is 1,3,5-triazin-4yl substituted with $R^a$ in position 2, said compounds being represented by formula (I-i), can be prepared by reacting an intermediate of formula (XXX) with an intermediate of formula (III) or a suitable salt thereof, such as for example formamidine acetate, guanidine hydrochloride, guanidine carbonate (2:1), guanidine sulphate, guanidine hemisulphate, N-(3-hydroxypropyl)guanidine hemisulphate, 1-piperazinecarboximidamide sulfate (2:1) and the like, in the presence of 1,1-dimethoxy-N,N-dimethyl-methanamine and in the presence of a suitable solvent, such as for example methanol/sodium methoxide.

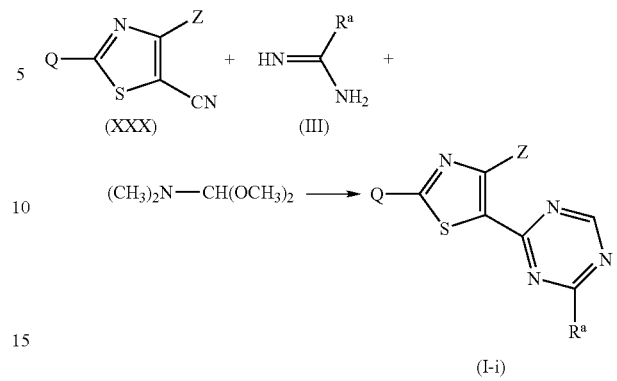

(I-i)

Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein L is substituted with amino may be converted into a compound of formula (I) wherein L is substituted with $C_{1-6}$alkylcarbonylamino by reaction with a $C_{1-6}$alkylcarbonyl chloride in a suitable solvent, such as for example pyridine.

Compounds of formula (I) wherein Q or L is substituted with cyano may be converted into a compound of formula (I), wherein Q or L is substituted with carboxyl by reaction with a suitable acid, such as concentrated hydrochloric acid, in the presence of a suitable reaction-inert solvent, e.g. water.

Compounds of formula (I) wherein Q or L is substituted with cyano may also be converted into a compound of formula (I), wherein Q or L is substituted with aminocarbonyl by reaction with a suitable acid, such as for example sulphuric acid, in the presence of water.

Compounds of formula (I), wherein L is substituted with $C_{1-6}$alkyl-C(=O)—NH—, may be converted into a compound of formula (I), wherein L is substituted with amino, by reaction with a suitable acid, such as for example hydrobromic acid and the like, in the presence of a suitable solvent, such as water.

Compounds of formula (I) wherein L is substituted with mercapto can be converted into a compound of formula (I) wherein L is substituted with $C_{1-6}$alkylthio by reaction with a suitable alkylating agent, such as for example $C_{1-6}$alkyl-I, e.g. $CH_3$—I, in the presence of a suitable solvent, such as for example an alcohol, e.g. ethanol.

Compounds of formula (I) wherein L is substituted with fluoro may be prepared from a compound of formula (I) wherein L is not substituted with fluoro by reaction with select fluor in the presence of 2,6-lutidine and a suitable solvent, such as for example N,N-dimethylformamide. Compounds of formula (a) wherein L is substituted with chloro or bromo may be prepared from a compound of formula (I) wherein L is not substituted with chloro or bromo by reaction with N-chlorosuccinimide or N-bromosuccinimide in the presence of a suitable solvent, such as for example carbon tetrachloride.

In the following paragraphs, there are described several methods of preparing the intermediates in the foregoing preparations. A number of intermediates and starting materials are commercially available or are known compounds which may be prepared according to conventional reaction procedures generally known in the art.

Intermediates of formula (II) can be prepared by reacting an intermediate of formula (IX) with $(CH_3)_2N—CH(OCH_3)_2$ at elevated temperature, optionally in the presence of a suitable solvent, such as for example N,N-dimethylformamide or toluene.

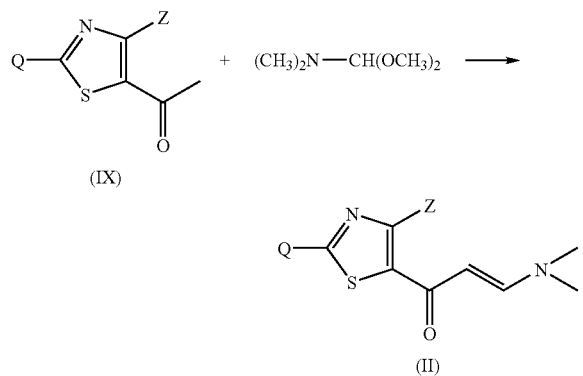

Intermediates of formula (IX) wherein Z represents $C_{1-6}$alkyl or $C_{1-6}$alkyloxycarbonyl, said Z being represented by $Z^a$ and said intermediates being represented by formula (IX-a), can be prepared by reacting an intermediate of formula (X) with an intermediate of formula (XI) wherein $W_1$ represents a suitable leaving group, such as halo, for example chloro, bromo, and $Z^a$ represents $C_{1-6}$alkyl or $C_{1-6}$alkyloxycarbonyl as described above, in the presence of a suitable solvent, such as for example, an alcohol, e.g. methanol, ethanol and the like, at elevated temperature.

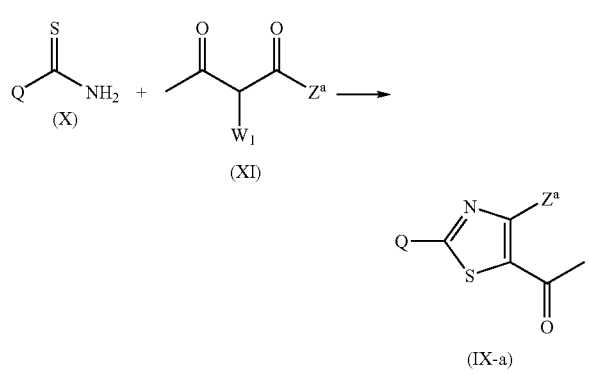

Intermediates of formula (IX) can also be prepared by oxidizing an intermediate of formula (XII) in the presence of a suitable oxidation reagent, such as for example pyridinium chlorochromate, in the presence of a suitable solvent, such as for example 1,2-dichloroethane and at elevated temperature.

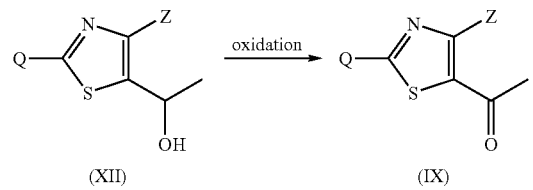

Intermediates of formula (XII) can be prepared by reacing an intermediate of formula (XIII) with $CH_3MgCl$ in the presence of a suitable solvent, such as for example tetrahydrofuran.

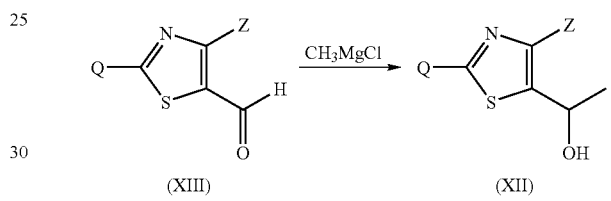

Intermediates of formula (XIII) can be prepared by reacting an intermediate of formula (XIV) wherein $W_2$ represents a suitable leaving group, such as for example halo, e.g. chloro and the like, with an intermediate of formula (XV) in the presence of a suitable catalyst, such as for example palladiumtetrakistriphenylphosphine, and a suitable solvent, such as for example tetrahydrofuran and a suitable salt, such as for example disodium carbonate in water.

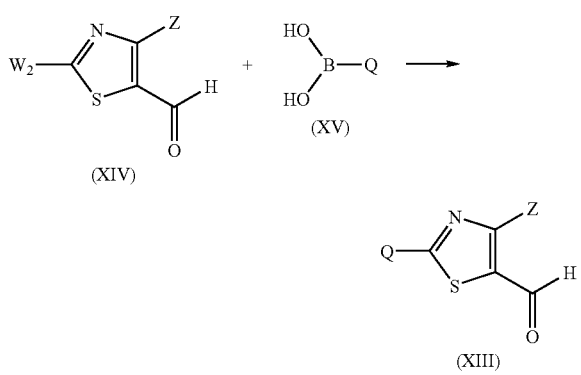

Intermediates of formula (IX) wherein Z represents chloro, said intermediates being represented by formula (IX-b), or intermediates of formula (XIII) wherein Z represents chloro, said intermediates being represented by formula (XIII-a), can be prepared by reacting an intermediate of formula (XVI) with N,N-dimethylformamide in the presence of $POCl_3$ at elevated temperature

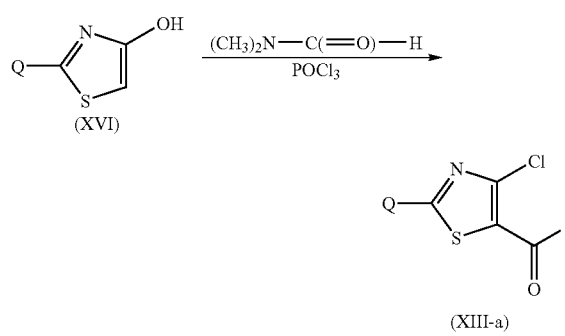

(XVI) → (XIII-a)

Intermediates of formula (XVI) can be prepared by reacting an intermediate of formula (X) with Cl—CH₂—C(=O)-Cl at elevated temperature.

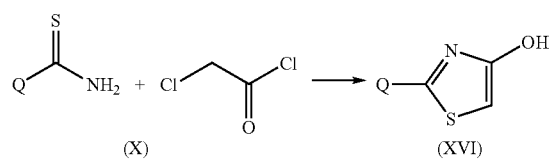

(X)　　　　(XVI)

Intermediates of formula (XIII-a) wherein Q represents 1-pyrrolyl, said intermediates being represented by formula (XIII-a-1), can be prepared by reacting 2-amino4-chloro-5-thiazolecarboxaldehyde (CAS 76874–79–8) with tetrahydro-2,5 dimethoxy-furan (CAS 696-59-3) in the presence of a suitable acid, such as for example acetic acid.

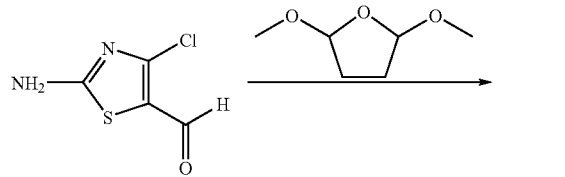

(XIII-a-1)

In an analogous manner can 2-amino-4-methyl-5-thiazolyl-ethanone (CAS 10601240–2) react with tetrahydro-2,5-dimethoxy-furan in the presence of a suitable acid, such as for example acetic acid, to form 2-pyrrol-1-ylmethyl-5-thiazolyl-ethanone.

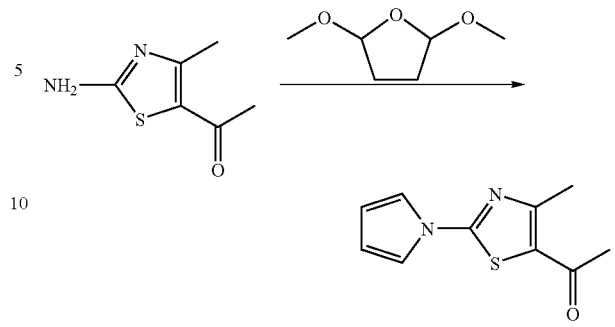

Intermediates of formula (XIII-a) wherein Q represents 1-pyrazolyl, said intermediates being represented by formula (XIII-a-2), can be prepared by reacting intermediate (XXXI) with an acid, such as for example acetic acid, in the presence of a suitable solvent, such as for example an alcohol, e.g. methanol and the like, at elevated temperature.

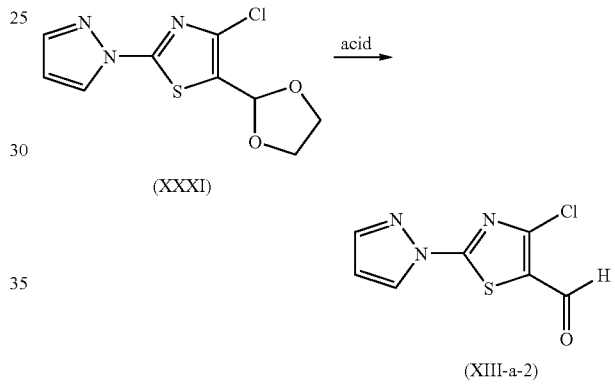

(XXXI) → (XIII-a-2)

Intermediates of formula (XXXI) can be prepared by reacting an intermediate of formula (X) with pyrazole in the presence of a suitable solvent, such as for example N,N-dimethylformamide and in the presence of sodium hydride.

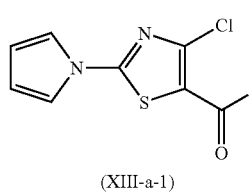

(XXXII) → (XXXI)

Intermediates of formula (XXXII) can be prepared by reacting an intermediate of formula (XXIII) with ethan-1,2-diol in the presence of a suitable acid, such as 4-toluenesulphonic acid, and a suitable solvent, such as toluene.

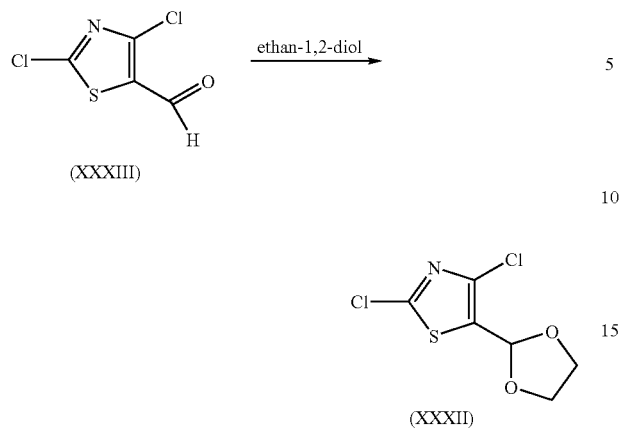

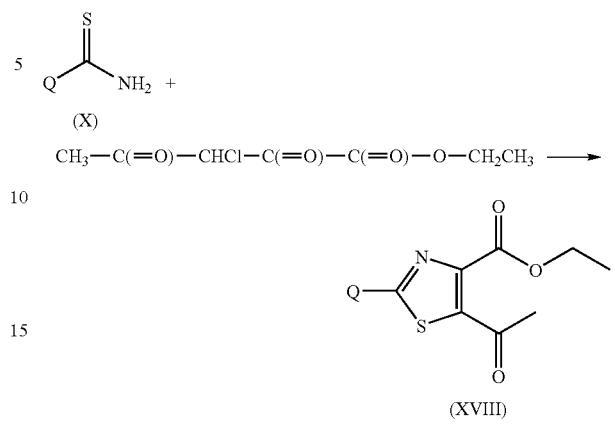

Intermediates of formula (II') can be prepared by reacting an intermediate of formula (XVII) with $(CH_3)_2N-CH(OCH_3)_2$ at elevated temperature.

Intermediates of formula (IV) can be prepared by reacting a compound of formula (I-e) with a suitable oxidation reagent, such as for example 3-chloroperoxybenzoic acid, in the presence of a suitable solvent, such as for example methylene chloride.

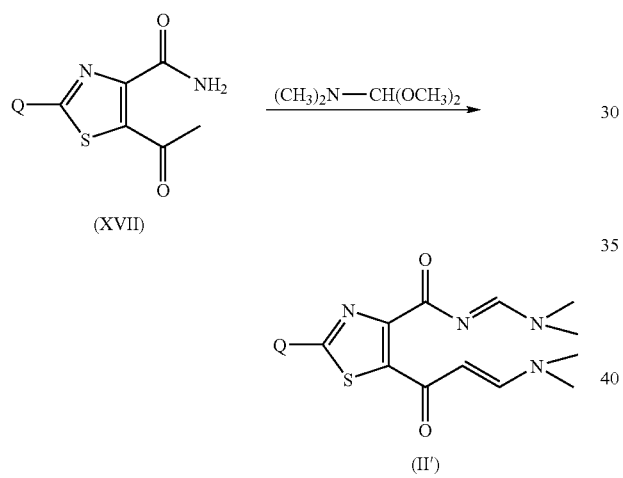

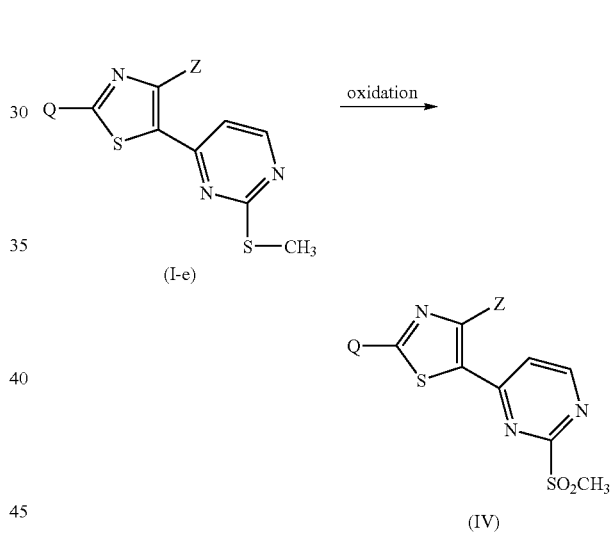

Intermediates of formula (XVII) can be prepared by reacting an intermediate of formula Q(VIII) with NH3 in the presence of a suitable solvent, such as for example an alcohol, e.g. methanol and the like.

Intermediates of formula (IV') can be prepared by reacting a compound of formula (I'-e) with a suitable oxidation reagent, such as for example 3-chloroperoxybenzoic acid, in the presence of a suitable solvent, such as for example chloroform, and a suitable base, such as for example disodium carbonate and sodium metabisulphite.

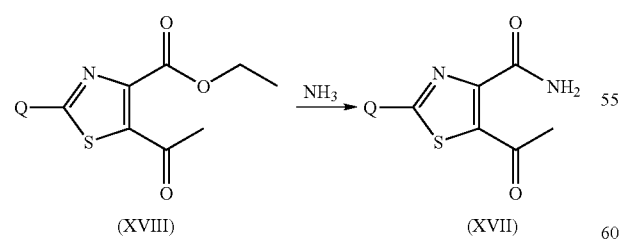

Intermediates of formula (XVIII) can be prepared by reacting an intermediate of formula (X) with $CH_3-C(=O)-CHCl-C(=O)-C(=O)-O-CH_2CH_3$ at elevated temperature in the presence of a suitable solvent, such as for example an alcohol, e.g. ethanol and the like.

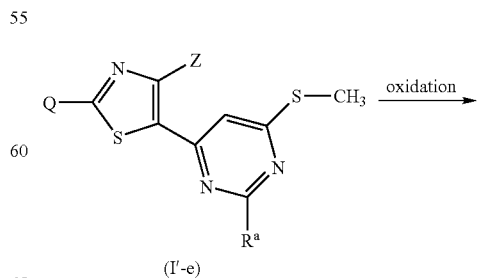

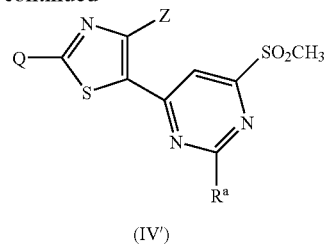

(IV')

Intermediates of formula (VI) can be prepared by reacting an intermediate of formula (IX) with $CH_3$-C(=O)—O—$C_{1-4}$ alkyl at elevated temperature in the presence of a suitable solvent, such as for example tetrahydrofuran, and in the presence of sodium hydride.

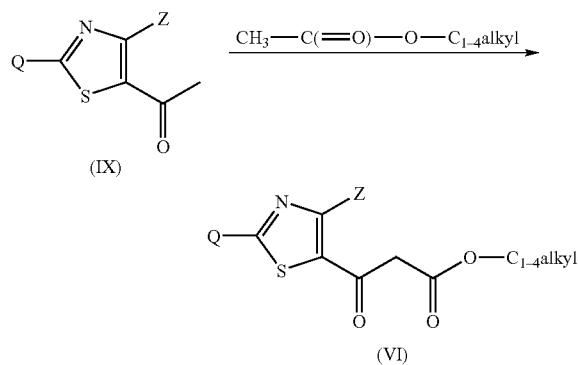

Intermediates of formula (IX) wherein Z represents chloro, said intermediates being represented by formula (IX-b), can be converted into an intermediate of formula (IX) wherein Z represents $C_{1-4}$alkyloxy, said intermediates being represented by formula (Ix-c), by reaction at elevated temperature with a suitable alcoholate, such as for example sodium methanolate (sodium methoxide) in the presence of a suitable solvent, such as for example an alcohol, e.g. methanol.

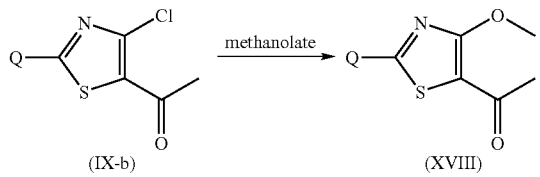

Intermediates of formula (VII) may be prepared by reacting an intermediate of formula (IXX) with hydrazine hydrate.

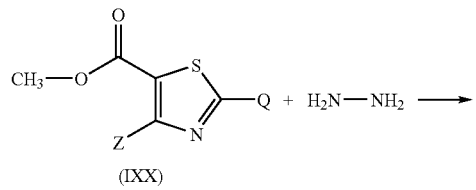

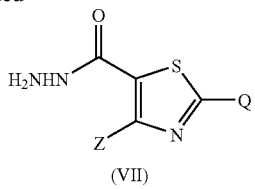

(VII)

Intermediates of formual (XXX) can be prepared by reacting an intermediate of formula (XXXIV) with a suitable anhydride, such as for example trifluoroacetic anhydride.

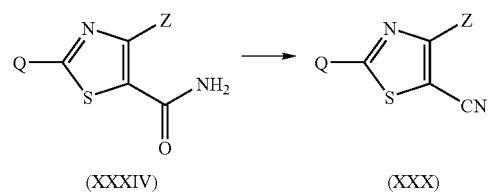

Intermediates of formula (XXXIV) can be prepared by reacting an intermediate of formula (V) with ammonia in the presence of oxalyl chloride and a suitable solvent, such as for example methylene chloride and N,N-dimethylformamide.

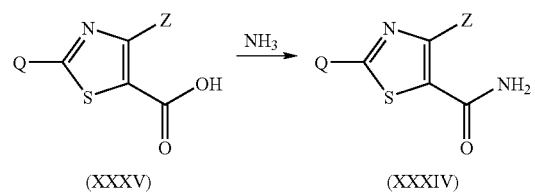

Intermediates of formula (XXXVI) can be prepared by reacting an intermediate of formula (IX) with carbon disulphide and methyl iodide in the presence of a suitable solvent, such as for example tetrahydrofuran, and a suitable base, such as for example potassium tert.-butoxide.

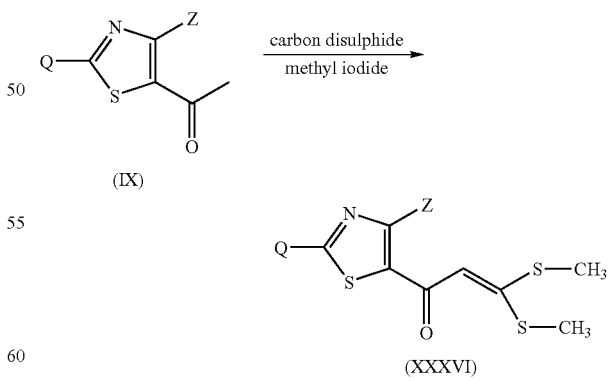

The intermediates of formula (IX) wherein Q represents 4-trifluoromethylphenyl and Z represents halo or $C_{1-4}$alkyl, said Z being represented by formula $Z^b$, and said intermediates being represented by formula (IX-c), are novel and also form part of the present invention.

Therefore, the present invention also relates to a compound of formula

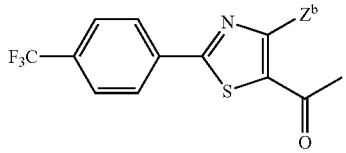

(IX-c)

wherein $Z^b$ represents halo or $C_{1-4}$alkyl.

Preferred compounds of formula (IX-c) are those compounds wherein $Z^b$ represents halo, in particular chloro.

The intermediates of formula (XIII) wherein Q represents 4-trifluoromethylphenyl and Z represents halo or $C_{1-4}$alkyl, said Z being represented by formula $Z^b$, and said intermediates being represented by formula (XIII-b), are novel and also form part of the present invention.

Therefore, the present invention also relates to a compound of formula

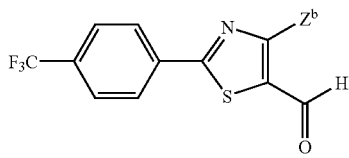

(XIII-b)

wherein $Z^b$ represents halo or $C_{1-4}$alkyl.

Preferred compounds of formula (XIII-b) are those compounds wherein $Z^b$ represents halo, in particular chloro.

The compounds of the present invention show cytokine production modulating activity, in particular cytokine production inhibitory activity, more in particular proinflammatory cytokine production inhibitory activity. A cytokine is any secreted polypeptide that affects the function of other cells by modulating interactions between cells in the immune or inflammatory response. Examples of cytokines include Interleukin-1 (IL-1) up to Interleukin-23 (IL-23), Tumor Necrosis Factor-alpha (TNF-α), Tumor Necrosis Factor-beta (TNF-β). The present compounds also show inhibitory activity on the production of chemotactic cytokines or chemokines responsible for trafficking and activation of leucocytes. A chemoline production inhibited by the compounds of formula (I) is MCP-1 production (Monocyte Chemotactic Protein 1).

The cytokine production specifically inhibited by the compounds of formula (I) is TNF-α and/or Interleukin-12 (IL-12) production.

TNF-α is primarily produced by monocytes, macrophages, T and B lymphocytes, neutrophils, mast cells, tumour cells, fibroblasts, keratinocytes, astrocytes, microglial cells, smooth muscle cells and others. This proinflammatory cytokine is established at the pinnacle of proinflammatory cascades; it exerts a key role in the cytokine network with regard to the pathogenesis of many infectious, inflammatory and autoimmune diseases. Excessive or unregulated TNF-α production is implicated in mediating or exacerbating a number of diseases including rheumatoid arthritis, rheumatoid spondylitis, spondyloarthropathies, systemic lupus erythematosus, osteoarthritis, gouty arthritis, juvenile arthritis and other arthritic conditions, polychondritis, sclero-doma, Wegener granulamatosis, dermatomyositis, Steven-Johnson syndrome, idiopatic sprue, endocrine opthalmopathy, Grave's disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupus, phthinoid bronchitis), chronic obstructive airway or pulmonary disease, pulmonary fibrosis, pneumoconiosis (aluminosis,anthracosis, asbestosis, chalicocis, ptilosis, siderosis, silicosis, tobaccosis, byssionosis), tuberculosis, silicosis, exacerbation of airways hyperreactivity to other drug therapy (e.g. aspirin or β-agonist therapy), pulmonary sarcoidosis, bone resorption diseases, meningitis, reperfusion injury, graft versus host reaction, allograft rejections, transplant rejections, fever and myalgias due to infection, such as influenza, cachexia (consequential to, e.g. bacterial, viral or parasitic, infection or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behcet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL2 infusion, anti-CD3 antibody infusion, hemodialysis, yellow fever vaccination. TNF-α has also been shown to activate HIV (Human Immune deficiency Virus) replication in monocytes and/or macrophages. Therefore, inhibition of TNF-α production or activity aids in limiting HIV progression. TNF-α also plays a role in other viral infections, such as Hepatitis C, CMV (cytomegalovirus), influenza and herpes virus infections, including herpes simplex virus type-1, herpes simplex virus type-2, varicella-zoster virus; Epstein-Barr virus, human herpes virus-6,-7 and -8, pseudorabies and rhinotracheitis. IL-12 is produced primarily by monocytes, macrophages and dendritic cells in response to bacteria, bacterial products (lipopolysaccharide) and immune signals. The production of IL-12 is regulated by other cytokines and endogenous mediators produced during inflammatory and immunological responses. IL-12 plays a central role in the immune system. Evidence obtained from animal models and human diseases suggests that inappropriate and protracted production of IL-12 and the ability of IL-12 to induce the generation of T helper 1 cell type responses may be instrumental in the development and maintenance of chronic inflammatory diseases, such as rheumatoid arthritis, collagen induced arthritis, allergic encephalitis, colitis, inflammatory bowel disease, Crohn's disease and multiple sclerosis, and in the triggering of autoimmune disorders, such as diabetes, or graft versus host diseases, shock or musculoskeletal and connective tissue diseases. The adverse effects also include anemia (haemolytic, aplastic, pure red cell, idiopatic thrombocytopenia), neutropenia, lymphopenia, hepatosplenomegaly with mononuclear cell infiltration and pulmonary edema with interstitial cell infiltrates. Excessive IL-12 production may accelerate the inflammatory progress of a disease, or the onset of the disease, such as rheumatoid arthritis, or it may also augment the disease severity.

Inhibition of TNF-α and/or IL-12 production by the compounds of formula (I) might offer an interesting, potentially less toxic alternative to non-specific immunosuppression (e.g. corticosteroids) in the treatment of chronic inflammatory and autoimmune diseases. The combined modulation of TNF-α and IL-12 production may ameliorate the treated disease to a greater extent than mono-therapy. The therapeutic effect of combining the suppression of both the immune and the inflammatory arm of a disease may provide additional clinical benefits. The present compounds are also indicated for use as co-therapeutic agents for use in conjunction with immunosuppressive and/or anti-inflammatory drugs, e.g. as potentiators of the therapeutic activity of said drugs, to reduce required dosaging or thus also potential side effects of said drugs. Immunosuppressive and/or anti-inflammatory drugs include, for example cyclopeptide, cyclopeptolide or macrolide immunosuppressive or anti-inflammatory drugs, such as drugs belonging to the cyclosporin class, e.g. cyclosporine A or G, tacrolimus substances, ascomycin, rapamycin, glucocorticosteroid drugs, e.g. budesonide, beclamethasone, fluticasone, mometasone.

The compounds of formula (I) are useful in preventing or treating cytokine mediated diseases, and as such, inhibit, suppress or antagonize the production or activity of proinflammatory cytokines, such as TNF-α and/or IL-12.

Disorders mediated through TNF-α and/or IL-12 refers to any and all disorders and disease states in which TNF-α and/or IL-12 play a role, either by the cytokine itself, or by the cytokine causing another cytokine, such as for example IL-1 or IL-6, or a certain mediator to be released.

Due to their cytokine production inhibitory activity, in particular their proinflammatory cytokine production inhibitory activity, more in particular their TNF-α and/or IL-12 inhibitory activity, even more in particular their IL-12 inhibitory activity, the compounds of formula (I), their N-oxides, pharmaceutically acceptable addition salts, quaternary amines and stereochemically isomeric forms are useful in the treatment or prevention of diseases or conditions mediated through cytokines, in particular diseases or conditions related to excessive or unregulated production of proinflammatory cytokines, such as TNF-α and/or IL-12, comprising inflammatory diseases or auto-immune diseases. Diseases or conditions related to an excessive or unregulated production of proinflammatory cytokines comprise rheumatoid arthritis, rheumatoid spondylitis, spondyloarthropathies, systemic lupus erythematosus, osteoarthritis, gouty arthritis, juvenile arthritis and other arthritic conditions, polychondritis, sclerodoma, Wegener granulamatosis, dermatomyositis, Steven-Johnson syndrome, idiopatic sprue, endocrine opthalmopathy, Graves' disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupous, phthinoid bronchitis), chronic obstructive airway or pulmonary disease, pulmonary fibrosis, tuberculosis, pneumoconiosis (aluminosis,anthracosis, asbestosis, chalicocis, ptilosis, siderosis, silicosis, tobaccosis, byssionosis), exacerbation of airways hyperreactivity to other drug therapy (e.g. aspirin or β-agonist therapy), silicosis, pulmonary sarcoidosis, bone resorption diseases, meningitis, allergic encephalitis, reperfusion injury, graft versus host reaction, allograft rejections, transplant rejections, musculoskeletal and connective tissue diseases, fever and myalgias due to infection, such as influenza, cachexia (consequential to, e.g. bacterial, viral or parasitic, infection or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behcet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL-2 infusion, anti-CD3 antibody infusion, hemodialysis, yellow fever vaccination, HIV or other viral infections, such as Hepatitis C, CMV, influenza and herpes virus infections, pseudorabies and rhinotracheitis, angiofollicular lympoid hyperplasia, anemia (haemolytic, aplastic, pure red cell, idiopatic thrombocytopenia), neutropenia, lymphopenia, hepatosplenomegaly with mononuclear cell infiltration and pulmonary edema with interstitial cell infiltrates; or to prevent these diseases. In particular, the compounds of formula (I) can be used to treat rheumatoid arthritis, Crohn's disease, irritable bowel disease, colitis, psoriasis or multiple sclerosis.

The cytokine production inhibitory activity of the compounds of formula (I) such as the inhibition of TNF-α and/or IL-12 production, may be demonstrated in the in vitro test "Inhibition of cytokine production in human whole blood cultures". Suitable in vivo tests are "Determination of cytokine in serum of LPS (lipopolysaccharide) and anti-CD3 challenged mice", "Inhibition of LPS-galactosamine induced shock in mice", "Inhibition of collagen induced arthritis in mice".

The compounds of formula (I) may also inhibit Interleukin-6 (IL-6).

The present compounds may also act as intermediates for the preparation of further thiazolyl derivatives.

In view of the above described pharmacological properties, the compounds of formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through cytokines, more in particular diseases mediated through TNF-α and/or IL-12, such as inflammatory and auto-immune diseases.

In view of the utility of the compounds of formula (I), there is provided a method of treating warm-blooded animals, including humans, suffering from or a method of preventing warm-blooded animals, including humans, to suffer from diseases mediated through cytokines, in particular mediated through TNF-α and/or IL-12, such as inflammatory and auto-immune diseases. Said methods comprise the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for preventing or treating diseases mediated through cytokines, in particular TNF-α and/or IL-12 comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components ( in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastrointestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:

a) dissolving the compound of formula (I) and the water-soluble polymer in an appropriate solvent, optionally at elevated temperatures;

b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:

a) mixing a compound of formula (I) and an appropriate water-soluble polymer, b) optionally blending additives with the thus obtained mixture, c) heating and compounding the thus obtained blend until one obtains a homogenous melt, d) forcing the thus obtained melt through one or more nozzles; and e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between 0-cyclodextrin an propylene oxide and may have a MS value of about 0.125 to 10, e.g. about 0.3 to 3.

Another type of substituted cyclodextrins is sulfobutyl-cyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of formula (I) may also be used in combination with other conventional anti-inflammatory or immunosuppressive agents, such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine, antilymphocytory immunoglobulines, antithymocytory immunoglobulines, azathioprine, cyclosporine, tacrolimus substances, ascomycin, rapamycm, muromonab-CD3.

Thus, the present invention also relates to the combination of a compound of formula (I) and another anti-inflammatory or immunosuppressive agent. Said combination may be used as a medicine. The present invention also relates to a product containing (a) a compound of formula (I), and (b) another anti-inflammatory or immunosuppressive compound, as a combined preparation for simultaneous, separate or sequential use in the treatment of diseases related to an excessive or unregulated cytokine production. The different drugs may be combined in a single preparation together with pharmaceutically acceptable carriers.

Experimental part

A. Preparation of the Intermediate Compounds

EXAMPLE A1A a) Preparation of Intermediate 1a

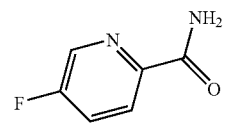

Palladium (II) acetate (0.0003 mol) and 1,3-bis(diphenylphosphino)-propane (0.0006 mol) were added to a solution of 2-chloro-5-fluoropyridine (0.01 mol) in tetrahydrofuran (100 ml) in an autoclave. Liquid ammonia (0.6 mol) was added, and carbon monoxide at a pressure of 40 atm admitted. The mixture was heated at 150° C. for 16 hours. After cooling to room temperature, methanol was added (200 ml), and the mixture stirred for 1 hour. The mixture was filtered, and the residue washed with methanol. The combined filtrates were evaporated to dryness under reduced pressure, the residue triturated under di-isopropylether, and dried under reduced pressure. Yield: 0.56 g of intermediate 1a (40%)

b) Preparation of Intermediate 1b

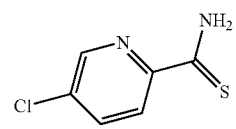

A mixture of 5-chloro-2-pyridinecarboxamide (0.004 mol), phosphorous pentasulphide (0.004 mol), and tetrahydrofuran (25 ml) were heated under reflux for 2 hours. The mixture was cooled to room temperature, filtered, and the residue washed with tetrahydrofuran. The residue was suspended in water (20 ml), and the mixture boiled for 15 minutes. After cooling it was extracted with dichloromethane:methanol 9:1. The phases were separated, the organic layer dried (MgSO$_4$), and the solvent removed under reduced pressure. Yield: 0.57 g of intermediate 1b (82%).

EXAMPLE A1B a) Preparation of Intermediate 1

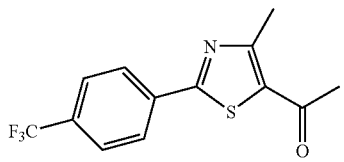

A mixture of 3-chloro-2,4-pentanedione (0.098 mol) and 4-trifluoromethylphenylcarbothioamide (0.098 mol) in ethanol (160 ml) was stirred and refluxed for 16 hours. The mixture was filtered, and the residue washed with ethanol and dried under reduced pressure. Yield: 17 g intermediate 1 (60%) (mp. 87–88° C.).

b) Preparation of Intermediate 2

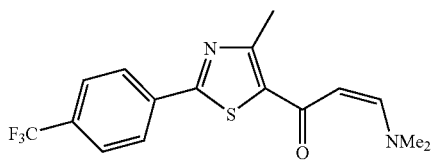

A suspension of intermediate 1 (0.035 mol) in 1,1-dimethoxy-N,N-dimethyl-methanamine (150 ml) was heated at 80° C. for 6 hours. The solvent was removed under reduced pressure, and the residue triturated under di-isopropyl ether. The mixture was filtered, the residue washed with di-isopropyl ether and then dried under reduced pressure. Yield: 11.0 g of intermediate 2 (92%) (mp. 147° C).

EXAMPLE A1C

Preparation of Intermediate 2a

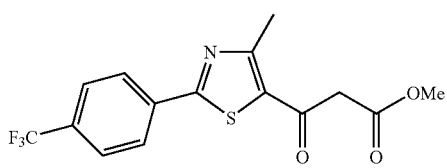

Dimethyl carbonate (0.07 mol) was added to suspension of sodium hydride (0.07 mol) in tetrahydrofuran (70 ml), and the mixture heated to 60° C. A solution of intermediate 1 (0.035 mol) in tetrahydrofuran (50 ml) was added dropwise. The reaction mixture was heated under reflux for 45 minutes, cooled to room temperature, and methanol added to destroy any remaining sodium hydride. The mixture was neutralised with acetic acid, and the solvent removed under reduced pressure. The residue was partitioned between ethyl acetate and water, the phases separated, and the aqueous layer extracted twice with ethyl acetate. The combined organic layers were washed with brine, dried (MgSO$_4$), and the solvent removed under reduced pressure. The resultant oil was triturated under diethyl ether/hexane, the mixture filtered, and the residue washed with hexane. Yield: 10.4 g intermediate 2a (87%).

EXAMPLE A2 a) Preparation of Intermediate 3

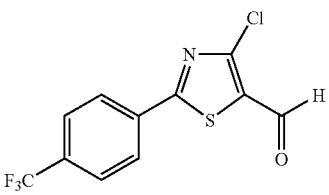

Pd(PPh$_3$)$_4$ (0.002 mol) was dissolved in tetrahydrofuran (120 ml). 2,4-dichloro-5-thiazolecarboxaldehyde (0.02 mol) was added. The reaction mixture was stirred at room temperature for 30 minutes. [4-(triuoromethyl)phenyl]boronic acid (0.021 mol) and Na$_2$CO$_3$/H$_2$O (11 g/80 ml) were added: The reaction mixture was stirred and refluxed for 3 hours. The reaction mixture was cooled, water was added. The mixture was extracted with CH$_2$Cl$_2$. The organic layer was separated, dried (NgSO$_4$), and the solvent evaporated. The residue was triturated under ethanol, washed with ethanol and dried under reduced pressure. Yield: 3,2 g of intermediate 3 (55%).

b) Preparation of Intermediate 4

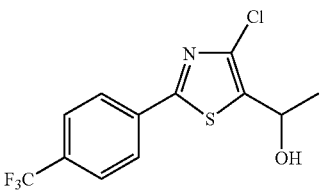

Intermediate 3 (0.011 mol) was dissolved in tetrahydrofuran ( 50 ml) and cooled to −10° C. A 3 M solution of methyl magnesiumchloride in tetrahydrofuran (3.7 ml, 0.011 mol) was added dropwise. The reaction mixture was stirred at room temperature for 3 hours. Water (3 ml) was added, followed by CH$_3$COOH (1 ml) (exothermic). The reaction mixture was extracted with ethyl acetate, the organic layer was separated, dried, filtered, and the solvent was evaporated. Yield: 3.4 g of intermediate 4 (100%).

c) Preparation of Intermediate 5

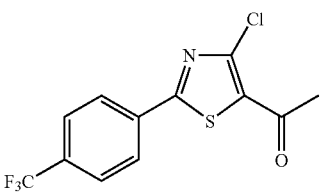

Intermediate 4 (0.01 mol) was dissolved in 1,2-dichloroethane (40 ml). Pyridinium chlorochromate (0.02 mol) was added to the reaction mixture. The reaction mixture was stirred at 70° C. for 3 hours, cooled to room temperature, poured onto a silica gel plug and eluted with dichloromethane. The eluent was evaporated under reduced pressure, and the residue dried under reduced pressure. Yield: 2.2 g of intermediate 5 (72%) (mp. 178° C.).

d) Preparation of Intermediate 6

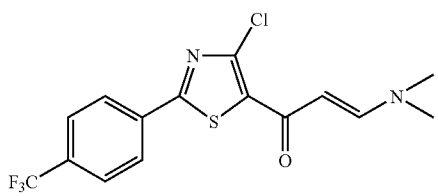

Intermediate 5 (0.004 mol) was dissolved in 1,1-dimethoxy-N,N-dimethyl-methanamine (50 ml) and stirred at 80° C. for 16 hours. The reaction mixture was cooled, water was added, and the mixture filtered. The residue was washed with water and dried under reduced pressure. Yield: 1.1 g of intermediate 6 (76%) (mp. 198° C.).

EXAMPLE A3A a) Preparation of Intermediate 7

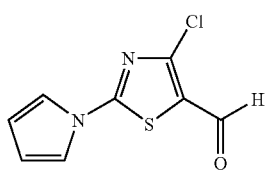

2-Amino4-chloro-5-thiazolecarboxaldehyde (0.012 mol) was dissolved in $CH_3COOH$ (80 ml) and heated. Tetrahydro-2,5dimethoxyfuran,(0.015 mol) was added dropwise to the hot solution. The reaction mixture heated under reflux for 2 hours. The solvent was evaporated. The residue was dried under reduced pressure. Yield: 2.0 g of intermediate 7 (78%). Intermediate 7 was transformed into N c intermediate 7'

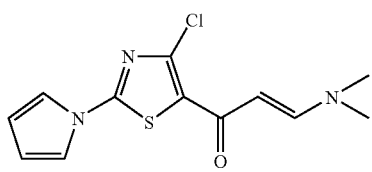

in a manner analogous to the transformation of intermediate 3 into intermediate 6 as described in Example A2. Yield: 57% of intermediate 7' (mp. 201° C.).

b) Preparation of Intermediate 7a

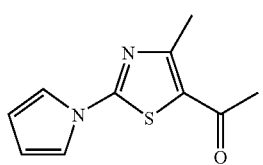

2-Amino4-methyl-5-acetylthiazole (0.030 mol) was dissolved in $CH_3COOH$ (160 ml) and heated. Tetrahydro-2,5-dimethoxyfuran (0.035 mol) was added dropwise to the hot solution. The reaction mixture was stirred under reflux for 2 hours. The solvent was evaporated. The residue was dried under reduced pressure. Yield: 5.3 g of intermediate 7a (86%).

EXAMPLE A3B a) Preparation of Intermediate 7b

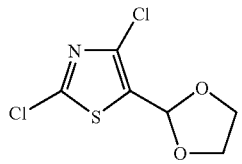

2,4-dichloro-5-thiazolecarboxaldehyde (0.027 mol), ethan-1,2-diol, and 4-toluenesulphonic acid were dissolved in toluene (60 ml) and heated under a Dean-Starck trap for 16 hours. The solvent was removed under reduced pressure and the residue chromatographed on silica gel using dichloromethane as eluent. Yield: 2.0 g of intermediate 7b (33%).

b) Preparation of Intermediate 7c

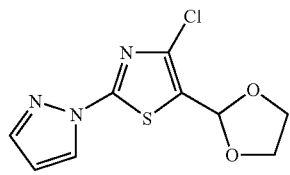

Sodium hydride (0.009 mol) was added portionwise to a stirred suspension of pyrazole (0.009 mol) in N,N-dimethylformamide (20 ml). Stirring was continued for 1 hour, and then intermediate 7b (0.009 mol) was added. The mixture was stirred for 72 hours, and ice-water added carefully. The mixture was filtered, the residue washed with water and then dried under reduced pressure. Yield: 1.7 g of intermediate 7c (74%).

c) Preparation of Intermediate 7d

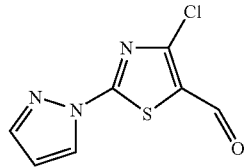

Intermediate 7c (0.0058 mol) was added to a solution of acetic acid (5 ml) in water (30 ml) and sufficient methanol added to cause dissolution. The solution was heated under reflux for 1 hour, cooled and then filtered. The residue was washed with water, and dried under reduced pressure. Yield: 1.2 g of intermediate 7d (97%).

d) Preparation of Intermediate 7e

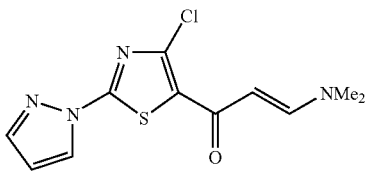

Intermediate 7d (0.0052 mol) was transformed into intermediate 7e (0.0028 mol) in a manner analogous to the transformation of intermediate 3 into intermediate 6 as described in Example A2. Yield: 0.8 g of intermediate 7e (54%) (mp 232° C.).

EXAMPLE A4 a) Preparation of Intermediate 8

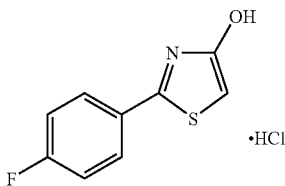

4-fluorophenylcarbothioamide (0.05 mol) and chloroacetyl chloride (0.2 mol) were mixed and stirred at room temperature for 10 minutes. The temperature of the reaction mixture was slowly increased to 60° C. After 30 minutes the reaction mixture was cooled to room temperature, and the volatile components were removed under reduced pressure. The residue was dissolved in diethyl ether, hexane was added, and the mixture was filtered. The residue was washed with diethyl ether/hexane (1/4), and then dried under reduced pressure. Yield: 8.9 g of intermediate 8 (77%).

b) Preparation of Intermediate 9

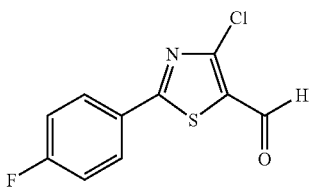

Phosphorous oxychloride (0.44 mol) was added dropwise to N,N-dimethylformamide (0.22 mol) at between 0° C. and 5° C. with rapid stirring. The reaction mixture was stirred for 30 minutes at 0° C. and then intermediate 8 (0.044 mol) was added while allowing the reaction mixture to warm up to room temperature. The reaction mixture was heated to 60° C. for 1 hour, and then heated under reflux for 90 minutes. Water was cautiously added, the mixture was filtered. The residue was triturated under diethyl ether, and dried under reduced pressure. Yield: 6.8 g of intermediate 9 (64%).

EXAMPLE A5 a) Preparation of Intermediate 11

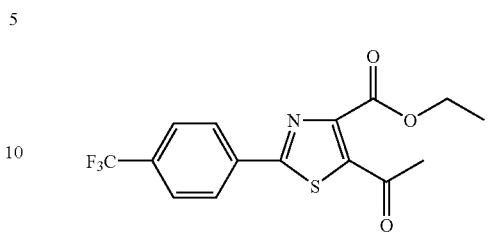

4-trifluoromethylphenylcarbothioamide (0.10 mol) was dissolved in ethanol (150 ml) and ethyl-3-chloroacetopyruvate (0.11 mol) dissolved in ethanol (50 ml) was added. The reaction mixture was stirred under reflux for 90 minutes. The solvent was evaporated under reduced pressure and the residue was partitioned between $CH_2Cl_2$ and saturated aqueous sodium bicarbonate. The phases were separated and the aqueous phase extracted twice with $CH_2Cl_2$. The combined organic layers were washed with water and then brine, dried ($MgSO_4$), and concentrated to dryness. The crude oily residue was triturated under hexane, chromatographed on silica gel using ethyl acetate:hexane (1:4) as eluent to give intermediate 11. Yield: 8.2 g of intermediate 11 (24%) (mp. 72–74° C.).

b) Preparation of Intermediate 12

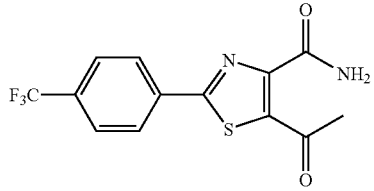

A solution of ammonia in methanol (7 M, 80 ml) was added dropwise to a cooled, stirred suspension of intermediate 11 (0.01 mol) in methanol (30 ml) at 0° C. The reaction mixture was stirred at 0° C. for a further 30 minutes and was then stirred at room temperature for 16 hours. The solvent was removed under reduced pressure, methanol added, and the bulk of the solvent removed under reduced pressure. The solution was cooled to 0° C., filtered, and the residue washed with cold methanol and then hexane. The crude product was recrystallised from ethanol:water (3:1). Yield: 1.7 g (54%) of intermediate 12 (mp. 196–200° C.).

c) Preparation of Intermediate 13

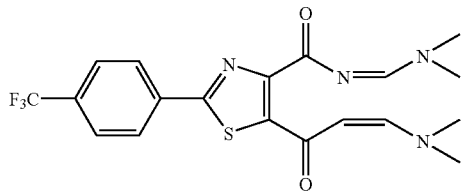

Intermediate 12 (0.002 mol) was mixed with 1,1-dimethoxy-N,N-dimethyl-methanamine (0.010 mol), and the mixture was heated at 110° C. for 40 minutes. After cooling to room temperature the mixture was filtered and the residue was triturated under hexane and separated. Yield: 0.84 g intermediate 13 (95%).

EXAMPLE A6

Preparation of Intermediate 14

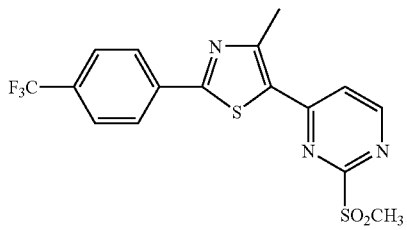

Compound 37 (prepared according to B6) (0.035 mol) and 3-chloroperoxybenzoic acid (0.077 mol) were stirred in dichloromethane for 16 hours. The reaction mixture was diluted with dichloromethane (150 ml), and washed with 5% aqueous sodium metabisulphite (3×100 ml), and then 5% aqueous sodium carbonate (2×100 ml). The reaction mixture was then washed repeatedly with water until the aqueous washings had reached pH 7. The undissolved solids were filtered off. The filtrate was dried (MgSO$_4$), and evaporated to dryness under reduced pressure to give a residue which was combined with the undissolved solids. Yield: 14 g of intermediate 14 (100%) (mp 223° C.).

Intermediate 14a

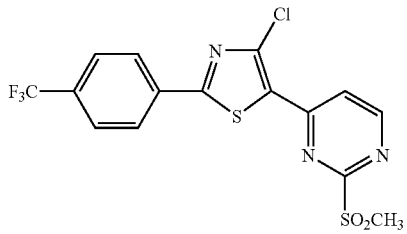

was prepared from compound 91 using the above method for intermediate 14. Yield: 74% of intermediate 14a.

EXAMPLE A7

Preparation of Intermediate 15

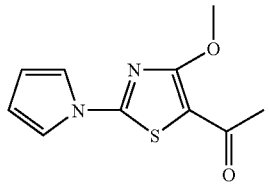

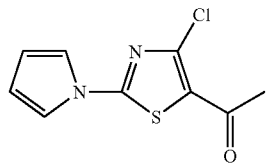

(prepared from intermediate 7 analogously to Example A2 b) and c)) (0.0044 mol) was dissolved in methanol (50 ml) and heated until total dissolution. A 30wt % solution of sodium methoxide in methanol (0.02 mol) was added. The reaction mixture was stirred and refluxed for 4 hours and stirred at room temperature overnight. The solvent was removed under reduced pressure. The residue was washed twice with water, and dried under reduced pressure. Yield: 0.7 g of intermediate 15 (71%).

EXAMPLE A8 a) Preparation of Intermediate 16

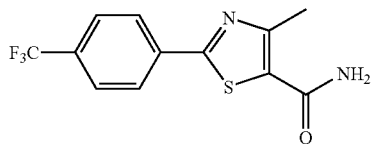

Oxalyl chloride (0.039 mol) was added dropwise to a stirred suspension of 4-methyl-2-(4-trifluoromethylphenyl)-5-thiazolecarboxylic acid (0.039 mol) and N,N-dimethylformamide (1 drop) in dichloromethane (200 ml) at 0° C. The mixture was allowed to warm to room temperature with stirring over 16 hours. The solvent was removed under reduced pressure, and dichloromethane (100 ml) was added. A solution of ammonia in methanol (7 M, 30 ml) was added, and the mixture stirred for 8 hours. The mixture was filtered, the residue washed with dichloromethane and then dried under reduced pressure. Yield: 10 g of intermediate 16 (90%) (mp 213–216° C.).

b) Preparation of Intermediate 17

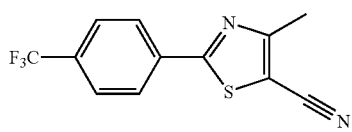

Trifluoroacetic anhydride (0.0063 mol) was added dropwise to a stirred suspension of intermediate 16 (0.0016 mol) and pyridine (0.010 mol) in 1,4-dioxane at 0° C. Stirring was continued for 30 minutes, the reaction mixture was allowed to warm to room temperature, and the mixture was stirred for a further 16 hours. The solvent was removed under reduced pressure, the residue triturated under water and dried under reduced pressure. Yield: 0.39 g of intermediate 17 (91%) (mp 90° C.).

EXAMPLE A9

Preparation of Intermediate 18

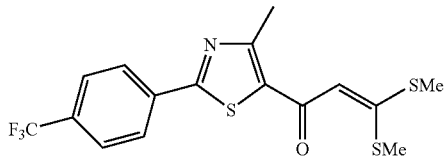

A solution of intermediate 1 (0.020 mol) in tetrahydrofuran (25 ml) was added dropwise to a stirred suspension of potassium tert-butoxide (0.040 mol) in tetrahydrofuran (100 ml) at room temperature. A deep red solution formed which was stirred for a further 30 minutes. Carbon disulphide (1.5 ml) was added dropwise, and after 30 minutes methyl iodide (4 ml) was added. The reaction mixture was stirred for 2 hours, then poured into water (11), and filtered. The residue was washed with water and dried under reduced pressure. Yield: 4.6 g of intermediate 18 (59%), mp. 164–166 (decomposition).

EXAMPLE A10

Preparation of Intermediate 19

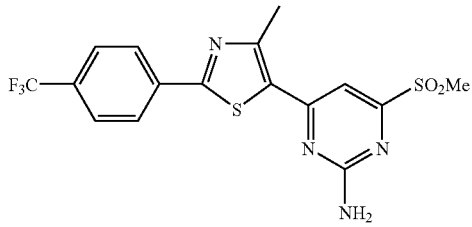

3-chloroperoxybenzoic acid (0.0045 mol) was added portionwise to a stirred suspension of compound 99 (0.0015 mol) in chloroform (10 ml) at room temperature. Stirring was continued for 16 hours. Chloroform (50 ml), and then saturated aqueous sodium metabisulphite (10 ml) were added, and rapid stirring continued for 15 minutes. Saturated aqueous disodium carbonate was added dropwise under gas evolution ceased. The mixture was washed with water and the phases were separated. The organic layer was dried ($Na_2SO_4$), and the solvent removed under reduced pressure. Yield: 0.60 g of intermediate 19 (97%) (mp.155–158° C.).

B. Preparation of the Final Compounds

EXAMPLE B1

Preparation of Compound 9

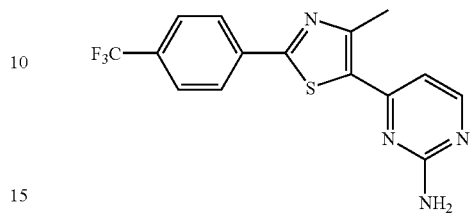

Sodium methoxide (0.045 mol) was added to a mixture of diguanidine carbonate (0.023 mol) in 2-ethoxyethanol (300 ml) and the mixture was stirred until a homogeneous solution was obtained. Intermediate 2 (0.023 mol) was added and the reaction mixture was heated under reflux for 3 hours. After cooling, water was added and the mixture was filtered. The residue was washed with water and dried under reduced pressure. Yield: 5.9 g of compound 9 (76%).

Alternative solvents are ethanol, N,N-dimethylformamide or dimethylsulphoxide.

EXAMPLE B2

A mixture of

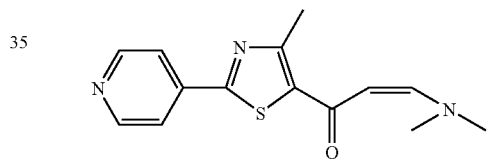

(0.016 mol) (prepared according to the procedures described in Ex. A1B) and hydrazine monohydrate (0.018 mol) in acetic acid (20 ml) were stirred under reflux overnight. Boiling water (100 ml) was added to the hot reaction mixture, and the resultant solution was allowed to cool. The mixture was filtered and the residue recrystallised from ethanol. Yield: 2.2g of compound 28 (57%).

EXAMPLE B3 a)

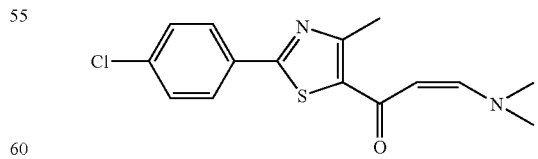

0 (0.016 mol) (prepared according to the procedures described in Ex. A1B) was added to a mixture of methylguanidine hydrochloride (0.024 mol) and sodium methoxide (0.026 mol)in N,N-dimethylformamide (30 ml). The mixture was heated at 100° C. for 26 hours. The mixture was diluted with water (80 ml) and acidified with acetic acid (2 ml). The mixture was filtered. The residue was dried and recrystallized from isooctane:toluene 3:1. Yield: 4.4 g of compound 17 (87%).

b)

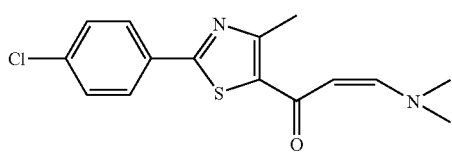

(0.0073 mol) (prepared according to the procedures described in Ex. A1B) was added to a mixture of formamidine acetate (0.022 mol) and sodium ethoxide (0.024 mol) in ethanol (20 ml), and the mixture was heated under reflux for 24 hours. A mixture of formamidine acetate (0.012 mol) and sodium ethoxide (0.013 mol) in ethanol (10 ml) was added, and the mixture heated under reflux for a further 24 hours. The mixture was diluted with water (30 ml) and acidified with acetic acid (3 ml). The solvent was removed under reduced pressure. The residue was dried under reduced pressure, and recrystallized from butan-1-ol. Yield: 1.2 g of compound 22 (57%).

c) Preparation of Compound 59

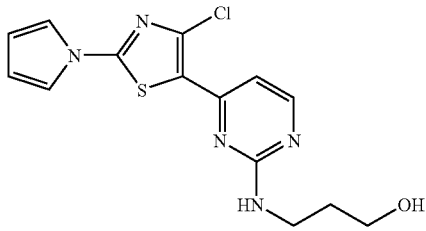

Sodium methoxide (0.0014 mol) was added to a mixture of 3-hydroxypropylguanidine hemisulphate (0.0014 mmol) in 2-methoxyethanol. Stirring was continued for 30 minutes, and then intermediate 7' (0.0007 mol) was added. The mixture was stirred at 100° C. for 16 hours, cooled, and the solvent was removed under reduced pressure. The residue was chromatographed on silica gel using dichloromethane as eluent. The residue was triturated under di-isopropylether, filtered, washed with di-isopropylether, and dried under reduced pressure. Yield: 0.013 g of compound 59 (6%).

EXAMPLE B4

Preparation of Compound 35

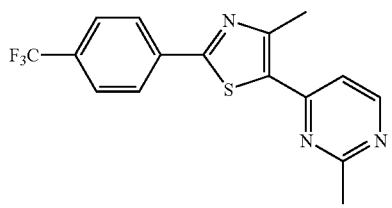

Sodium methoxide (0.0041 mol) was suspended in 2-ethoxyethanol (6 ml), and acetamidine hydrochloride (0.0041 mol) was added. The mixture was stirred for 30 minutes at room temperature. Intermediate 2 (prepared according to Ex. A1Bb)) (0.0018 mol) was added, and the mixture was stirred under reflux for 8 hours. A slurry of sodium methoxide (0.020 mol) and acetamidine hydrochloride (0.020 mol) in 2-ethoxyethanol (2 ml) was added. After stirring under reflux for 1 hour, the reaction mixture was cooled and poured into ice-cold water (70 111). The mixture was filtered and the residue washed with water. Yield: 0.59 g of compound 35 (98%).

EXAMPLE B5

Preparation of Compound 36

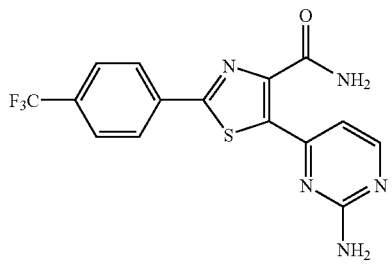

Guanidine hydrochloride (0.0054 mol) was added to a solution of sodium methoxide (0.0054 mol) in ethanol (10 ml), and the mixture was stirred for 30 minutes. A solution of intermediate 13 (prepared according to A5c) (0.0018 mol) in ethanol (10 ml) was added, and the reaction mixture refluxed for 1 hour. After cooling, water was added, the mixture was filtered, and the residue washed with ethanol-water. The residue was dried and recrystallized from 2-ethoxyethanol. Yield: 0.23 g of compound 36 (35%) (mp. 286–287° C.).

EXAMPLE B6

Intermediate 2 (0.009 mol) and thiourea (0.010 mol) were added to a solution of potassium hydroxide ( 0.009 mol) in ethanol (25 ml), and the resulting mixture was refluxed for 5 hours. The mixture was cooled on an ice-bath, filtered, and the residue was washed with diethyl ether. The residue was dried under reduced pressure, and then dissolved in a solution of sodium hydroxide (0.027 mol) in water (40 ml). Dimethyl sulphate (0.018 mol) was added dropwise at room temperature. After 2 hours, water (10 ml) was added and the reaction mixture was extracted with diethyl ether (2×40 ml).

The organic layers were combined, washed with water (100 ml) and then brine (10 ml), and then dried (NgSO₄). The solvent was removed under reduced pressure. Yield: 2.28 g of compound 37 (69%).

Compound 91

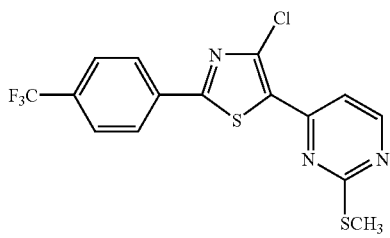

was prepared from intermediate 6 using the above method for compound 37. Yield: 52% of compound 91.

EXAMPLE B7 a) Preparation of Compound 38

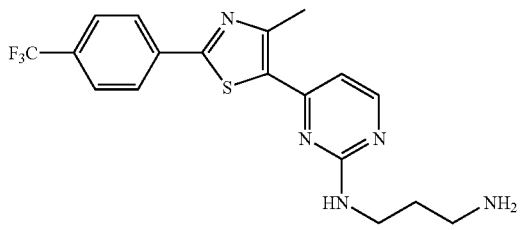

Intermediate 14 (prepared according to A6) ( 0.001 mol) was suspended in propane-1,3-diamine (2 ml), and the mixture was heated at 130° C. for 15 minutes. After cooling, water was added with stirring, and the mixture stood for 16 hours. The mixture was filtered and the residue washed with water. The residue was dried under reduced pressure. Yield: 0.35 g of compound 38 (89%).

In analogous reactions, a suitable solvent, such as N,N-dimethylformamide, may optionally be added if the amine used is not liquid at 20° C.

b) Preparation of Compound 84

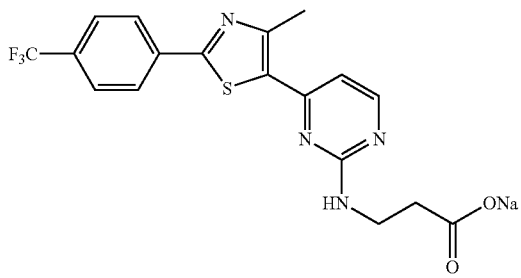

Intermediate 14 (prepared according to A6) (0.0005 mol), 3-aminopropionic acid (0.001 mol), and disodium carbonate (0.001 mol) were suspended in dimethylsulphoxide and the mixture was heated to 120° C. for 3 hours. The mixture was cooled to room temperature and water (6 ml) was added with stirring. Stirring was continued until crystallisation was complete, the mixture was filtered, and the residue dried under reduced pressure. Yield: 0.2 g of compound 84 (93%).

c) Preparation of Compound 83

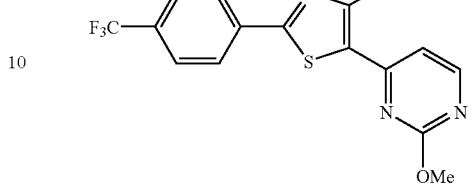

A solution of sodium methoxide in methanol (30 wt %, 0.2 ml) was added to a solution of intermediate 14 (prepared according to A6) (0.0002 mol), and methanol (0.8 ml) in tetrahydrofuran (4 ml), and the solution was stirred for 16 hours at room temperature. The solvent was removed under reduced pressure, and the residue stirred in acetonitrile (2 ml) and water (4 ml). The mixture was filtered and the residue dried under reduced pressure. Yield: 0.051 g of compound 83 (73%).

d) Preparation of Compound 82

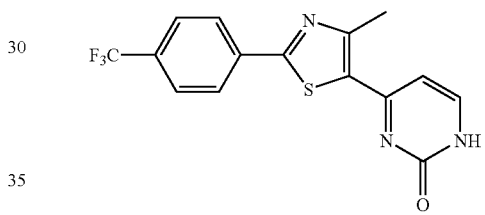

A solution of sodium hydroxide (1 M, 0.4 ml) was added to a solution of intermediate 14 (prepared according to A6) (0.0002 mol) and water (0.6 ml) in tetrahydrofuran (4 ml). The solution was briefly warmed, and then stirred at room temperature for 72 hours. The solvent was removed under reduced pressure, and the residue stirred in acetonitrile (2 ml), water (2 ml), and aqueous hydrochloric acid (1 M, 0.4 ml). The mixture was filtered and the residue dried under reduced pressure. Yield: 0.058 g of compound 82 (86%).

e) Preparation of Compound 40

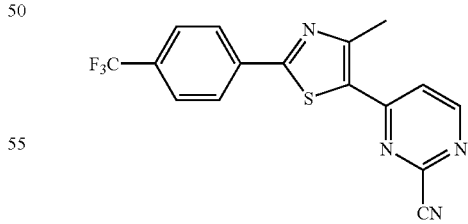

Intermediate 14 (prepared according to A6) (0.0013 mol) was suspended in N,N-dimethylformamide (5 ml) and potassium cyanide (0.003 mol) was added. The reaction mixture was heated at 100° C. for 15 minutes, cooled to room temperature and water added. The mixture was filtered and the residue was washed with water. The residue was dried under reduced pressure. Yield: 0.43 g of compound 40 (96%).

f) Preparation of Compound 70

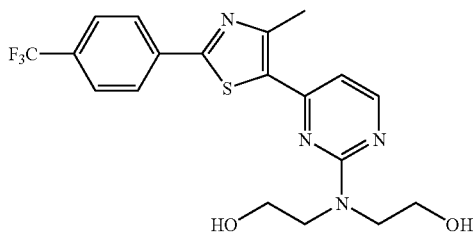

Intermediate 14 (prepared according to A6) (0.001 mol) was suspended in di-(2-hydroxyethyl)-amine (1 ml), and the mixture was heated at 100° C. for 30 minutes. After cooling, water was added with stirring, and the mixture was filtered. The residue was washed with water, and the residue was dried under reduced pressure. Yield: 0.18 g of compound 70 (42%).

g) Preparation of Compound 87

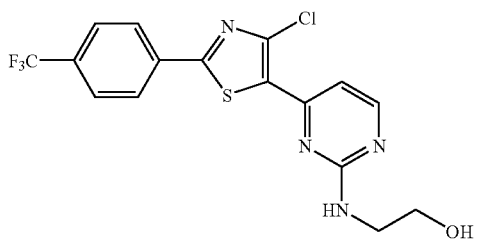

Intermediate 14a (prepared according to A6) (0.0001 mol) was dissolved in tetrahydrofuran (4 ml), and 2-aminoethanol (0.0002 mol) was added. The solution was stirred at room temperature for 1 hour, the solvent removed under reduced pressure and the residue was dissolved in MeOH (2 ml). The solution was acidified with a 6 M solution of hydrogen chloride in 2-propanol. 2-propanone (4 ml) was added, and the mixture was stirred for 16 hours. The mixture was filtered and the residue dried under reduced pressure. Yield: 0.354 g of compound 87 (87%).

h) Preparation of Compound 90

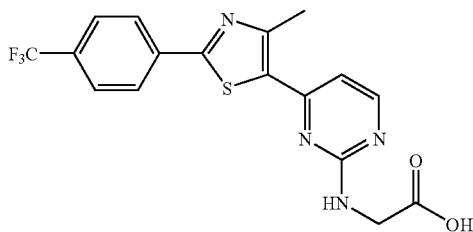

Intermediate 14 (prepared according to A6) (0.0005 mol) was added to dimethylsulphoxide (5 ml) and the suspension was warmed gently until dissolution was complete. Glycine (0.001 mol) and then sodium carbonate (0.001 mol) were added. The mixture was stirred at 120° C. for 4 hours, cooled to 100° C., and then water (5 ml) was added. The solution was neutralised with 1 M hydrochloric acid. Water (3 ml) was added and then cooled with rapid stirring to 0° C. The mixture was filtered and the residue dried under reduced pressure. Yield: 0.192 g of compound 90 (92%).

i) Preparation of Compound 89

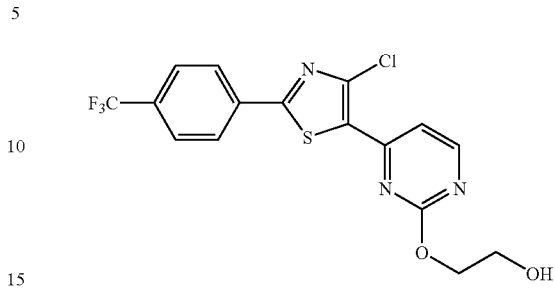

Ethan-1,2-diol (1 ml) was added dropwise to a mixture of sodium hydride (60% in oil, 0.0005 mol) in N,-dimethyl-formamide, and stirring continued for 30 minutes. Intermediate 14a (0.0002 mol) was added and the reaction stirred for 20 hours. The solvent was removed under reduced pressure, taken up in water (5 ml) and neutralised with acetic acid. The mixture was gently warmed and acetonitrile was added slowly until dissoluton was complete. After cooling, the mixture was filtered, and the residue was dried under reduced pressure and chromatographed on silica gel using dichloromethane:methanol 99:1 as eluent Yield: 0.023 g of compound 89 (29%).

EXAMPLE B8

Preparation of Compound 81

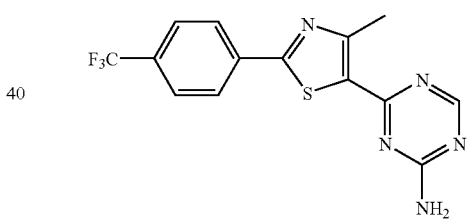

Sodium methoxide (0.0028 mol) was added to a stirred solution of intermediate 17 (0.0028 mol) (prepared according to Ex. A8b) in methanol (20 ml), and stirring was continued for 16 hours.

In a separate flask guanidine hydrochloride (0.0028 mol) was suspended in methanol (15 ml) and sodium methoxide ( 0.0028 mol) was added, and stirring continued for 1 hour. This solution was then added to the first prepared solution. Stirring was continued for 16 hours. The solvent was removed under reduced pressure and 1,1-dimethoxy-N,N-dimethyl-methanamine (0.0028 mol), followed by a solution of sodium methoxide (0.0028 mol) in methanol (5ml), was added. The reaction was stirred for 16 hours. The solvent was removed under reduced pressure, methanol (5 ml) was added, and the solvent again removed under reduced pressure. The residue was suspended in hot ethanol, and the mixture was filtered whilst hot. The cool filtrate was filtered and the residue dried under reduced pressure. Yield: 0.080 g of compound 81 (7%).

EXAMPLE B9

Preparation of Compound 2

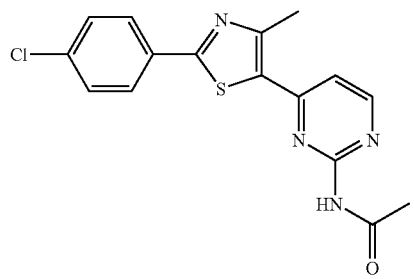

A solution of acetyl chloride (1.5 ml) in dichloromethane (10 ml) was dropwise added to a mixture of compound 32 (0.019 mol) in pyridine (30 ml). The mixture was stirred at room temperature for 75 hours, water (30 ml) was added and the mixture was filtered. The residue was washed with hexane and recrystallized from acetic acid. Yield: 3.55 g of compound 2 (54%).

EXAMPLE B10 a) Preparation of Compound 49

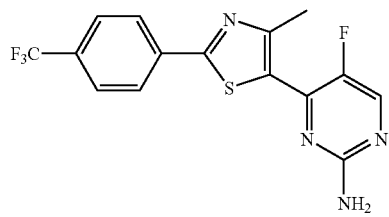

[1-(chloromethyl)4-fluoro-1,4-diazoniabicyclo[2.2.2]octane bis(tetrafluoroborate)] "Selectfluor"(0.003 mol) was added to a solution of compound 9 (0.0024 mol) (prepared according to B1) and 2,6-lutidine (0.045 mol) in N,N-dimethylformamide (5 ml). The reaction mixture was stirred at room temperature for 48 hours, and the volatile components removed under reduced pressure. The residue was chromatographed on silica gel using tetrahydrofuran:hexane 1:4 as eluent. Yield: 0.093 g of compound 49 (11%).

b) Preparation of Compound 16

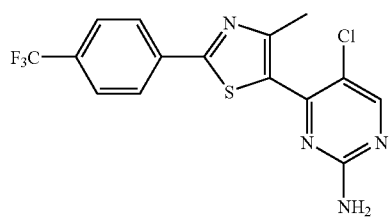

N—Chlorosuccinimide (0.0038 mol) was added to a solution of compound 9 (0.0035 mol) (prepared according to B1) in carbon tetrachloride (30 ml). The mixture was refluxed for 5 hours, and the solvent was removed at reduced pressure. The residue was suspended in water, the mixture boiled for 5 minutes, and the mixture filtered. The residue was recrystallised from ethanol. Yield: 0.81 g of compound 16 (62%).

c) Preparation of Compound 11

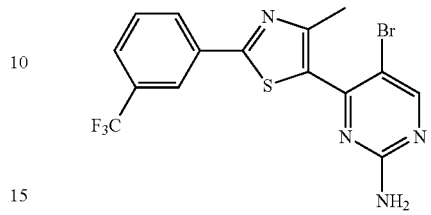

N-Bromosuccinimide (0.0026 mol) was added to a solution of compound 6 (prepared according to B1) (0.0024 mol) in carbon tetrachloride (3 ml). The mixture was refluxed for 4 hours, and the solvent removed at reduced pressure. The residue was recrystallised from ethanol:water (4:1), and then from ethanol. Yield: 0.89 g of compound 11 (89%).

EXAMPLE B11

Preparation of Compound 42

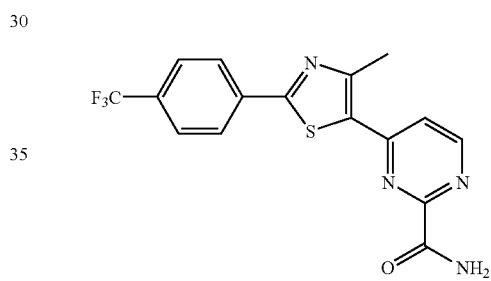

Compound 40 (prepared according to B7e) (0.00087 mol) was dissolved in concentrated sulphuric acid (98%, 28 ml) and the mixture was heated to 40° C. Water (0.35 ml) was slowly added. After stirring for 2 hours, the reaction mixture was poured onto ice and neutralised with cold aqueous ammonia. The mixture was filtered, and the residue washed with water and then with ethanol:diethyl ether (1:5). Yield: 0.25 g of compound 42 (79%).

EXAMPLE B12

Preparation of Compound 80

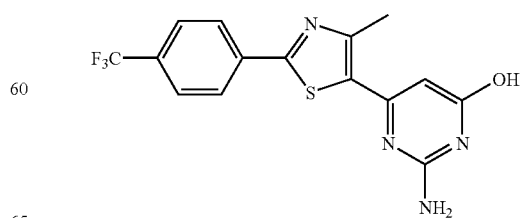

A mixture of guanidine hydrochloride (0.025 mol) and sodium methoxide (0.025 mol) in 2-ethoxyethanol (20 ml) were refluxed for 15 minutes, and then intermediate 2a (0.013 mol) was added in one portion. Stirring was continued under reflux for 90 minutes, and the solution was cooled and diluted with ethanol and water. The pH was adjusted to 3 using acetic acid. The mixture was filtered, and the residue washed with water and then dried under reduced pressure. Yield.: 3.6 g of compound 80 (79%).

EXAMPLE B13

Preparation of Compound 99

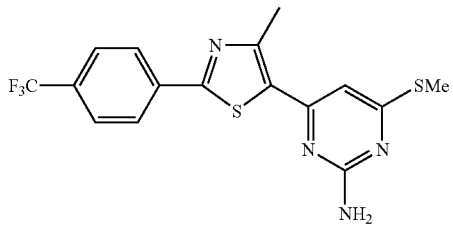

Sodium hydride (0.020 mol) was added to a solution of guanidine hydrochloride (0.020 mol) in N,N-dimethylformamide (10 ml) and stirring continued for 30 minutes. A solution of intermediate 18 (0.014 mol) in N,N-dimethylformamide (10 ml) was added, and the reaction was heated under reflux for 2 hours. The solution was cooled to 0° C., water (150 ml) was added, and the mixture was filtered. The residue was dried under reduced pressure. Yield: 1.5 g of compound 99 (28%). A sample was recrystallised from acetonitrile to give compound 99 as a yellow solid (mp. 178–180° C.).

EXAMPLE B14

Preparation of Compound 97

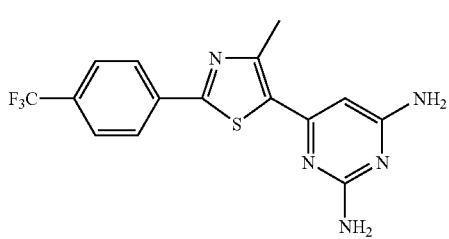

Intermediate 20 (0.001 mol) was dissolved in tetrahydrofuran (10 ml) in an autoclave and liquid ammonia (0.6 mol) was added. The autoclave was closed and the reaction stirred at room temperature for 16 hours. The mixture was filtered, and the volatile components removed from the filtrate under reduced pressure. The residue was chromatographed on silica gel using dichloromethane:methanol 99:1 as eluent. Yield: 0.15 g of compound 97 (42%).

Compounds 92, 93, 94, 95, 96 and 98 were made analogously according to the method described in Example B7a) or B7f).

Tables 1, 2 and 3 list the compounds of formula (I) which were prepared according to, analogue to one of the examples and methods described above.

TABLE 1

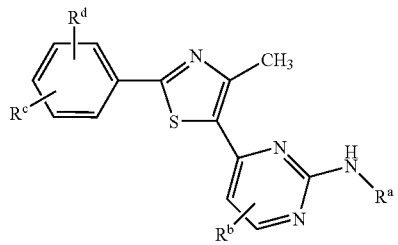

| Comp. No. | Ex. No. | $R^a$ | $R^b$ | $R^c$ | $R^d$ | Physical data (m.p.) |
|---|---|---|---|---|---|---|
| 1 | B1 | H | H | H | H | 203 |
| 2 | B9 | —C(=O)—CH₃ | H | 4-Cl | H | >280 |
| 3 | B1 | H | H | 2-Cl | H | 209 |
| 4 | B1 | H | H | 2-Cl | 3-Cl | 220 |
| 5 | B1 | H | H | 2-Cl | 4-Cl | |
| 6 | B1 | H | H | 3-CF₃ | H | 168 |
| 7 | B1 | H | H | 3-Cl | H | 175 |
| 8 | B1 | H | H | 3-F | H | 198 |
| 10 | B1 | H | H | 4-F | H | 221 |
| 11 | B10c | H | 5-Br | 3-CF₃ | H | 166 |
| 12 | B10c | H | 5-Br | 3-F | H | 136 |
| 14 | B10c | H | 5-Br | 4-F | H | 169 |
| 15 | B10b | H | 5-Cl | 3-CF₃ | H | 174 |
| 17 | B3a | CH₃ | H | 4-Cl | H | |
| 32 | B1 | H | H | H | 4-Cl | H |
| 43 | B1 | H | H | 4-CH₃ | H | 209 |
| 80 | B12 | H | 6-OH | 4-CF₃ | H | >270 |

TABLE 2
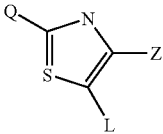
| Comp. No. | Ex. No. | Q | L | Z | Physical data (m.p.) |
|---|---|---|---|---|---|
| 20 | B1 | 2-pyridyl | 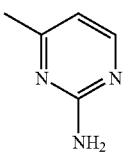 | $CH_3$ | 248 |
| 21 | B1 | 3-pyridyl | 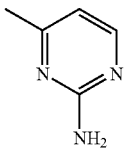 | $CH_3$ | |
| 22 | B3b | 4-chlorophenyl | 4-pyrimidinyl | $CH_3$ | 191 |
| 23 | B2 | phenyl | 3-pyrazolyl | $CH_3$ | 200 |
| 24 | B2 | 4-chlorophenyl | 3-pyrazolyl | $CH_3$ | 204 |
| 25 | B2 | 2-pyridyl | 3-pyrazolyl | $CH_3$ | 190 |
| 26 | B2 | 3-pyridyl | 3-pyrazolyl | $CH_3$ | 177 |
| 27 | | phenyl | 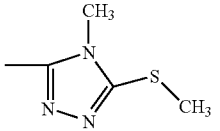 | $CH_3$ | 138 |
| 28 | B2 | 4-pyridyl | 3-pyrazolyl | $CH_3$ | 198 |
| 29 | B3a | 4-pyridyl | 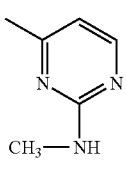 | $CH_3$ | 188 |
| 30 | B3b | 4-pyridyl | 4-pyrimidinyl | $CH_3$ | 144 |
| 31 | B1 | 4-pyridyl | 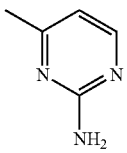 | $CH_3$ | 249 |
| 32 | B1 | 1-pyrrolyl | 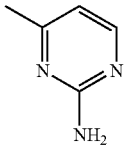 | $CH_3$ | 188 |
| 33 | B1 | 2-thienyl | 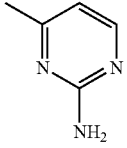 | $CH_3$ | 198 |

TABLE 2-continued
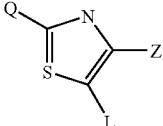
| Comp. No. | Ex. No. | Q | L | Z | Physical data (m.p.) |
|---|---|---|---|---|---|
| 34 | B1 | 1-pyrrolyl | 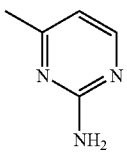 | Cl | 239 |
| 44 | B1 | 4-fluorophenyl | 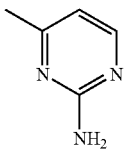 | Cl | 241 |
| 45 | B1 | phenyl | 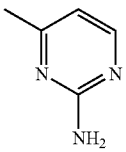 | Cl | 213 |
| 46 | B1 | 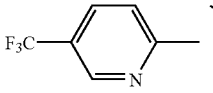 | 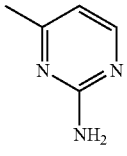 | CH$_3$ | 197 |
| 47 | B1 | 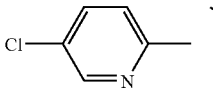 | 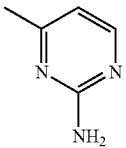 | CH$_3$ | 251 |
| 48 | B1 | 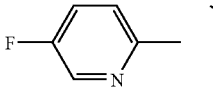 | 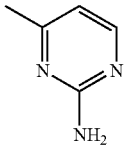 | CH$_3$ | 247 |
| 50 | B1 | 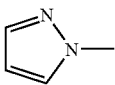 | 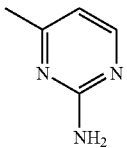 | Cl | 240 |
| 36 | B5 | 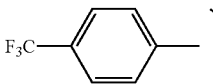 | 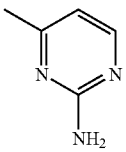 | —C(=O)—NH$_2$ | 287 |

TABLE 2-continued

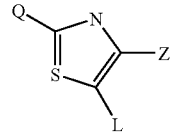

| Comp. No. | Ex. No. | Q | L | Z | Physical data (m.p.) |
|---|---|---|---|---|---|
| 51 | B3c | F₃C-pyridinyl | 4-methyl-pyrimidin-2-yl-NH-CH₂CH₂OH | CH₃ | |
| 52 | B1 | N-methylpyrrolyl | 4-methyl-pyrimidin-2-yl-NH₂ | OCH₃ | 177 |
| 53 | B3a | F₃C-pyridinyl | 4-methyl-pyrimidin-2-yl-NHCH₃ | CH₃ | .HCl(1:1) 194 |
| 54 | B3a | F₃C-phenyl | 4-methyl-pyrimidin-2-yl-NHCH₃ | Cl | 220 |
| 55 | B3c | F₃C-pyridinyl | 4-methyl-pyrimidin-2-yl-NH-CH₂CH₂CH₂OH | CH₃ | 172 |
| 56 | B3a | F₃C-pyridinyl | 4-methyl-pyrimidin-2-yl-piperazinyl | CH₃ | .HCl(1:2) .H₂O(1:1) >250 |
| 57 | B3c | N-methylpyrrolyl | 4-methyl-pyrimidin-2-yl-NH-CH₂CH₂OH | Cl | 184 |

TABLE 2-continued
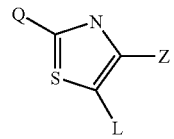
| Comp. No. | Ex. No. | Q | L | Z | Physical data (m.p.) |
|---|---|---|---|---|---|
| 58 | B3c | 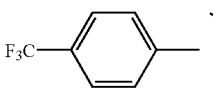 | 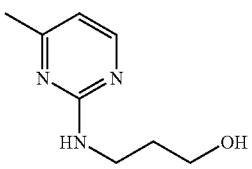 | Cl | 177 |
| 59 | B3c | 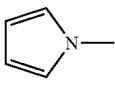 | 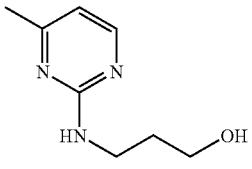 | Cl | 182 |
| 67 | B7a | 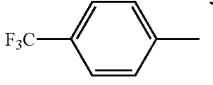 | 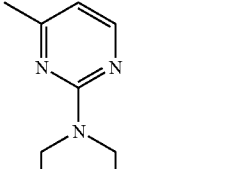 | CH$_3$ | 184 |
| 68 | B7a | 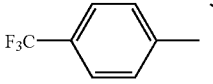 | 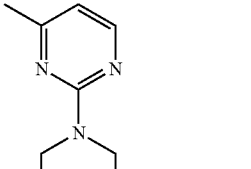 | CH$_3$ | 139 |
| 69 | B7a | 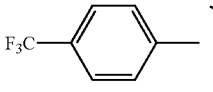 | 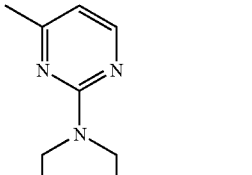 | CH$_3$ | 124 |
| 70 | B7f | 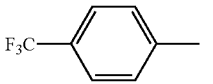 | 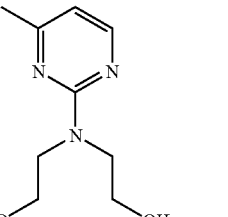 | CH$_3$ | 164–180 |

TABLE 2-continued
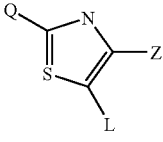
| Comp. No. | Ex. No. | Q | L | Z | Physical data (m.p.) |
|---|---|---|---|---|---|
| 35 | B4 | 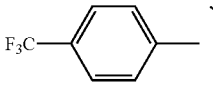 | 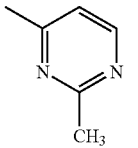 | CH$_3$ | 106 |
| 42 | B11 | 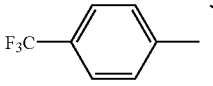 | 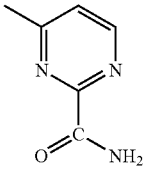 | CH$_3$ | 231 |
| 40 | B7e | 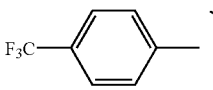 | 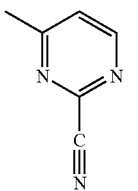 | CH$_3$ | 214 |
| 76 | B3a | 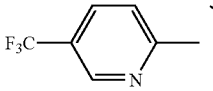 | 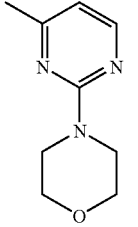 | CH$_3$ | 188 |
| 77 | B7a | 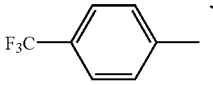 | 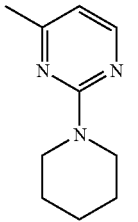 | CH$_3$ | 114 |
| 78 | B3a | 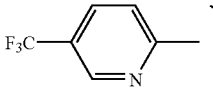 | 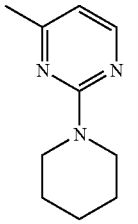 | CH$_3$ | |

TABLE 2-continued
| Comp. No. | Ex. No. | Q | L | Z | Physical data (m.p.) |
|---|---|---|---|---|---|
| 37 | B6 | 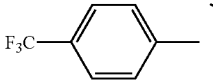 | 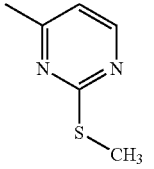 | CH$_3$ | 123 |
| 79 | B6 |  | 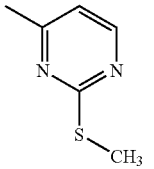 | CH$_3$ | |
| 81 | B8 | 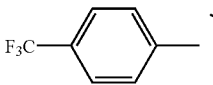 | 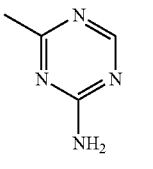 | CH$_3$ | 208 |
| 82 | B7d | 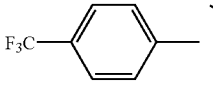 | 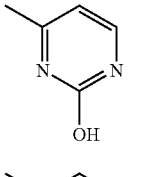 | CH$_3$ | >260 |
| 83 | B7c | 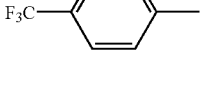 | 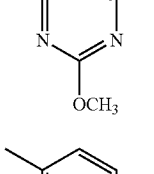 | CH$_3$ | 128 |
| 86 | B3a | 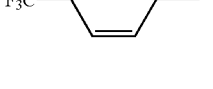 | 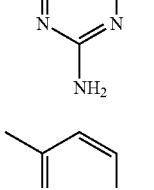 | Cl | 216 |
| 87 | B7g | 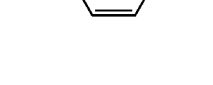 | 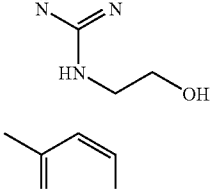 | Cl | HCl 210 |
| 88 | B7a | 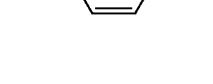 | 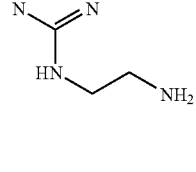 | Cl | >250 |

TABLE 2-continued
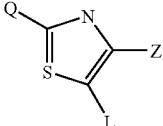
| Comp. No. | Ex. No. | Q | L | Z | Physical data (m.p.) |
|---|---|---|---|---|---|
| 89 | B7i | 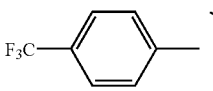 | 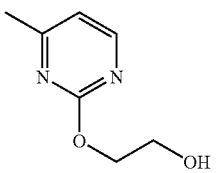 | Cl | 152 |
| 91 | B6 | 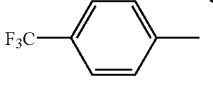 | 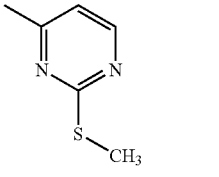 | Cl | 146 |
| 92 | B7f | 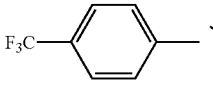 | 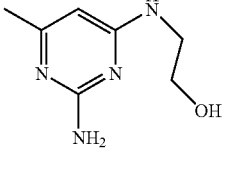 | CH$_3$ | 174 |
| 93 | B7f | 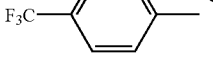 | 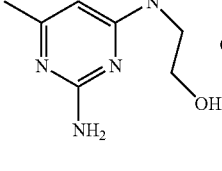 | CH$_3$ | 145 (decomposition) |
| 94 | B7f | 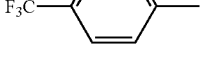 | 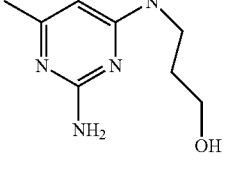 | CH$_3$ | .HCl 210 (decomposition) |
| 95 | B7a | 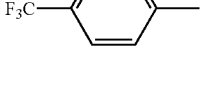 | 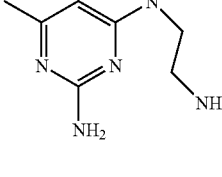 | CH$_3$ | 84 (decomposition) |
| 96 | B7a | 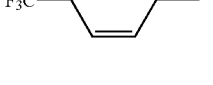 | 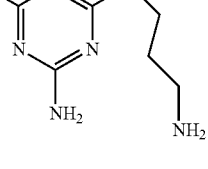 | CH$_3$ | .HCl 260 (decomposition) |

TABLE 2-continued

| Comp. No. | Ex. No. | Q | L | Z | Physical data (m.p.) |
|---|---|---|---|---|---|
| 97 | B14 | 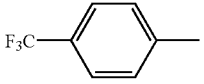 | 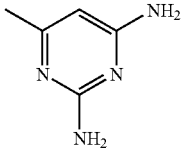 | $CH_3$ | 207 |
| 98 | B7c | 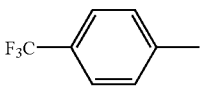 | 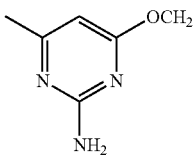 | $CH_3$ | 163 |
| 99 | B13 | 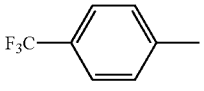 | 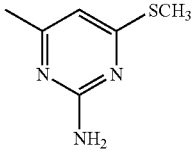 | $CH_3$ | — |

TABLE 3

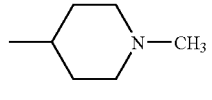

| Comp. No. | Ex. No. | $R^a$ | $R^b$ | Physical data (m.p.) |
|---|---|---|---|---|
| 9 | B1 | H | H | 186 |
| 13 | B10c | H | 5-Br | 190 |
| 16 | B10b | H | 5-Cl | 186 |
| 49 | B10a | H | 5-F | 181 |
| 60 | B7a | —$CH_2$—$CH_2$—$NH_2$ | H | 171 |
| 38 | B7a | —$CH_2$—$CH_2$—$CH_2$—$NH_2$ | H | 139 |
| 61 | B7a | —$(CH_2)_6$—$NH_2$ | H | 120–130 |
| 62 | B7a | —$(CH_2)_8$—$NH_2$ | H | 110–120 |
| 63 | B7g | —$CH_2$—$CH_2$—OH | H | 188 |
| 64 | B7g | —$CH_2$—$CH_2$—$CH_2$—OH | H | 173 |
| 65 | B7g | —$CH_2$—CH(OH)—$CH_2$—OH | H | 194 |
| 66 | B7a | —C(=NH)—$NH_2$ | H | 241 |
| 71 | B7a | —$(CH_2)_7$—$NH_2$ | H | 110 |
| 72 | B7a | 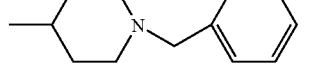 | H | 185 |
| 73 | B7a | (4-piperidinyl)—$CH_2$—phenyl | H | 155 |
| 74 | B7g | —CH($CH_2$—OH)—$CH_2$—OH | H | 201 |
| 75 | B7a | —$(CH_2)_2$—O—$(CH_2)_2$—O—$(CH_2)_2$—$NH_2$ | H | 89 |
| 84 | B7b | —$CH_2$—$CH_2$—C(=O)$O^-Na^+$ | H | >240 |

TABLE 3-continued

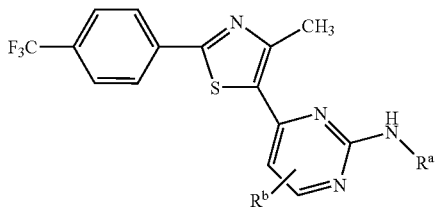

| Comp. No. | Ex. No. | Rª | Rᵇ | Physical data (m.p.) |
|---|---|---|---|---|
| 85 | B7b | —CH₂—C(=O)O⁻Na⁺ | H | |
| 90 | B7h | —CH₂—COOH | H | 248 |

C. Pharmacological Example

EXAMPLE C.1

In Vitro Inhibition of TNF-α Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 μl of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 6 hours, cell-free supernatant fluids were collected by centrifugation and stored at −20° C. until tested for the presence of TNF-α.

EXAMPLE C.2

In Vitro Inhibition of IL-12p40 Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 pi of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 24 hours, cell-free supernatant fluids were collected by centrifugation and stored at −20° C. until tested for the presence of IL-12 p40.

EXAMPLE C.3

Cytokine Measurements

Cytokine protein concentrations were determined by sandwich ELISA as described in Van Wauwe et al. (1996, Inflamm Res, 45, 357–363). Murine monoclonals used as capture antibodies to human cytokines were obtained from R&D Systems (Abingdon, United Kingdom) and code named MAB210 and MAB611 for TNF-α and IL-12 p40 respectively. Biotinylated goat polyclonal antibodies used to detect human cytokines were from R&D Systems (BAF210, BAF219). Cytokine levels were calculated from standard curves using recombinant cytokines supplied by R&D Systems.

EXAMPLE C.4

In Vitro Inhibition of IL-12p70 Production in Human Blood

Human Whole Blood Stimulation

Peripheral blood from healthy donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 200 μl fractions were distributed in 96-well plates (Nunc, Roskilde, Denmark). Blood samples were preincubated (5 minutes at 37° C.) in a humidified 5% $CO_2$-atmosphere with 25 μl of drug solvent (final concentration 0.1% dimethylsulfoxide in RPMI 1640) or with 25 μl of an appropriate dose of test compound before being stimulated by the addition of 25 μl of lipopolysaccharide at a final concentration of 100 ng/ml. After 24 hours, cell-free supernatant fluids were collected by centrifugation and stored at −20° C. until tested for the presence of IL-12.

EXAMPLE C.5

Cytokine Measurements

Cytokine protein concentrations were determined by sandwich ELISA as described in Van Wauwe et al. (1996, Inflamm Res, 45,357–363). The quantikine HS kit (R &D HS120, Abingdon, United Kingdom) was used to quantify the cytokine levels (IL12 p70) in the supernatant Table 4 lists the percentage inhibition of TNF-α and IL-12 production (column "% inhib.") at a test dose of $1\times10^{-6}$, $1\times10^{-7}$ or $1\times10^{-8}$ M for the compounds of the present invention.

TABLE 4

| Comp. No | % inhib. TNF-α | | % inhib. IL-12 (p40) | % inhib. IL-12 (p70) |
|---|---|---|---|---|
| | $1 \times 10^{-6}$ M | $1 \times 10^{-7}$ M | $1 \times 10^{-6}$ M | $1 \times 10^{-8}$ M |
| 1 | 50 | 51 | 55 | |
| 5 | | | 46 | |
| 8 | | | 59 | |
| 9 | | | 57 | 92 |
| 10 | | | 53 | |
| 20 | 54 | | 51 | |
| 32 | 55 | 54 | 56 | |
| 34 | | | | 95 |
| 35 | | | | 94 |
| 38 | | | 93 | |
| 40 | | | 93 | |
| 49 | | | 92 | |
| 58 | | | | 84 |
| 63 | | | | 93 |
| 70 | | | | 90 |
| 73 | | | | 92 |
| 74 | | | | 82 |
| 80 | | | 49 | |
| 81 | | | | 94 |
| 83 | | | 59 | |
| 84 | | | | 95 |
| 90 | | | 56 | |

The invention claimed is:

1. A compound of formula

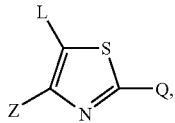

(I)

a N-oxide, a pharmaceutically acceptable addition salt, a quaternary amine and a stereochemically isomeric form thereof,
wherein
Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl or $C_{1-6}$alkyloxy; polyhalo$C_{1-4}$alkyl; $C_{1-4}$alkyloxy; cyano; amino; aminocarbonyl; mono- or di($C_{1-6}$alkyl)aminocarbonyl; $C_{1-6}$alkyloxycarbonyl; $C_{1-6}$alkylcarbonyloxy; $H_2N$—$S(=O)_2$—; mono- or di($C_{1-6}$alkyl)amino-$S(=O)_2$; —$C(=N-R^x)NR^yR^z$;
$R^x$ is hydrogen, $C_{1-6}$alkyl, cyano, nitro or —$S(=O)_2$—$NH_2$;
$R^y$ is hydrogen, $C_{1-6}$alkyl, $C_{2-6}$alkenyl or $C_{2-6}$alkynyl;
$R^z$ is hydrogen or $C_{1-6}$alkyl;
Q is $C_{3-6}$cycloalkyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyrimidinyl, pyrazinyl, pyridazinyl, benzthiazolyl, benzoxazolyl, benzimidazolyl, indazolyl, or imidazopyridyl, wherein each of said ring systems may optionally be substituted with up to three substituents each of said substituents independently being selected from halo; hydroxy; cyano; carboxyl; azido; amino; mono- or di($C_{1-6}$alkyl)amino; $C_{1-6}$alkylcarbonylamino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-4}$alkyl; polyhalo$C_{1-6}$alkyloxy; polyhalo$C_{1-6}$alkylcarbonyl; $C_{1-4}$alkyl-$S(=O)_n$— or $R^1HN$—$S(=O)_n$—, with $R^1$ representing hydrogen, or a radical of formula

(a-1)

with A being O, S or a bivalent radical of formula —$CR^2=N$— with $CR^2$ attached to N of formula (a-1); and
$R^2$ being hydrogen, $C_{1-6}$alkyl or $C_{1-6}$alkyloxy;
or
Q is a radical of formula

(b-1)

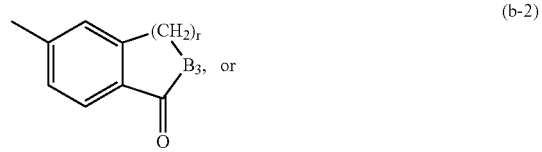

(b-2)

(b-3)

wherein $B_1$ and $B_2$ each independently are O, $NR^3$, $CH_2$ or S, with $R^3$ being hydrogen or $C_{1-4}$alkyl;
$B_3$ is O or $NR^4$ with $R^4$ being hydrogen or $C_{1-4}$alkyl;
q is an integer with value 1 to 4;
r is an integer with value 1 to 3;
n is an integer with value 1 or 2;
L is phenyl substituted with up to 4 substituents each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-$C(=O)$—NH—; $C_{1-6}$alkyloxy-$C(=O)$—NH—; $H_2N$—$C(=O)$—NH—; mono- or di($C_{1-4}$alkyl)amino-$C(=O)$—NH—; Het-NH—; $Het^1$-NH—; —NH—$C(=N-R^x)NR^yR^z$; —$C(=N-R^x)NR^yR^z$; $Het^1$; or a radical of formula

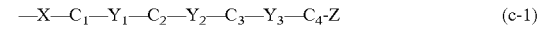

(c-1)

wherein
X represents $NR^5$, O, S or a direct bond;
$C_1$, $C_2$, $C_3$ and $C_4$ each independently represent $C_{1-6}$alkanediyl, $C_{2-6}$alkenediyl, $C_{2-6}$alkynediyl or a direct bond;
$Y_1$, $Y_2$ and $Y_3$ each independently represent $NR^5$, O, S or a direct bond;

Z is hydrogen, halo, cyano, hydroxy, carboxyl, —P(=O)(OH)H, —P(=O)(OH)$_2$, —P(=O)(OH)CH$_3$, —P(=O)(OH)(OCH$_3$), —P(=O)(OH)(OCH$_2$CH$_3$), —P(=O)(OH)NH$_2$, —S(=O)$_2$H, —S(=O)$_2$(OH), —S(=O)$_2$NH, —C(=O)—NH—S(=O)$_2$—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

R$^5$ is hydrogen, C$_{1-6}$alkyl or —C(=NH)—N(R$^z$)$_2$; and wherein from 1 to 3 hydrogen atoms of the C$_{1-6}$alkyl, C$_{1-6}$alkanediyl, C$_{2-6}$alkenediyl or C$_{2-6}$alkynediyl groups in the definitions of R$^5$ and the radical of formula (c-1) may optionally and each independently be replaced by halo, hydroxy, carboxyl, —P(=O)(OH)H, —P(=O)(OH)$_2$, —P(=O)(OH)CH$_3$, —P(=O)(OH)—(OCH$_3$), —P(=O)(OH)(OCH$_2$CH$_3$), —P(=O)(OH)NH$_2$, —S(=O)$_2$H, —S(=O)$_2$(OH), —S(=O)$_2$NH, —C(=O)—NH—S(=O)$_2$—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

or

L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from C$_{1-6}$alkyloxycarbonyl; C$_{1-6}$alkylcarbonyloxy; aminocarbonyl; mono- or di(C$_{1-4}$alkyl)aminocarbonyl; C$_{1-6}$alkyl-C(=O)—NH—; C$_{1-6}$alkyloxy-C(=O)—NH—; H$_2$N—C(=O)—NH—; mono- or di(C$_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula

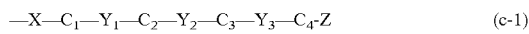

$$-X-C_1-Y_1-C_2-Y_2-C_3-Y_3-C_4-Z \qquad (c\text{-}1)$$

wherein

X represents NR$^5$, O, S or a direct bond;

C$_1$, C$_2$, C$_3$ and C$_4$ each independently represent C$_{1-6}$alkanediyl, C$_{2-6}$alkenediyl, C$_{2-6}$alkynediyl or a direct bond;

Y$_1$, Y$_2$ and Y$_3$ each independently represent NR$^5$, O, S or a direct bond;

Z is hydrogen, halo, cyano, hydroxy, carboxyl, —P(=O)(OH)H, —P(=O)(OH)$_2$, —P(=O)(OH)CH$_3$, —P(=O)(OH)(OCH$_3$), —P(=O)(OH)(OCH$_2$CH$_3$), —P(=O)(OH)NH$_2$, —S(=O)$_2$H, —S(=O)$_2$(OH), —S(=O)$_2$NH, —C(=O)—NH—S(=O)$_2$—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

R$^5$ is hydrogen, C$_{1-6}$alkyl or —C(=NH)—N(R$^z$)$_2$; and wherein from 1 to 3 hydrogen atoms of the C$_{1-6}$alkyl, C$_{1-6}$alkanediyl, C$_{2-6}$alkenediyl or C$_{2-6}$alkynediyl groups in the definitions of R$^5$ and the radical of formula (c-1) may optionally and each independently be replaced by halo, hydroxy, carboxyl, —P(=O)(OH)H, —P(=O)(OH)$_2$, —P(=O)(OH)CH$_3$, —P(=O)(OH)—(OCH$_3$), —P(=O)(OH)(OCH$_2$CH$_3$), —P(=O)(OH)NH$_2$, —S(=O)$_2$H, —S(=O)$_2$(OH), —S(=O)$_2$NH, —C(=O)—NH—S(=O)$_2$—H, tetrazolyl, 3-hydroxy-isothiazolyl, 3-hydroxy-isoxazolyl, 3-hydroxy-thiadiazolyl, mercaptotetrazolyl, 3-mercapto-triazolyl, 3-sulfinyl-triazolyl, 3-sulfonyl-triazolyl;

Het is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, amino, cyano, carboxyl, mono- or di(C$_{1-6}$alkyl)amino, C$_{1-6}$alkyl, C$_{1-6}$alkyl substituted with hydroxy or C$_{1-4}$alkyloxy or amino or mono- or di(C$_{1-4}$alkyl)amino, polyhaloC$_{1-6}$alkyl, C$_{1-6}$alkyloxy, C$_{1-6}$alkylthio, C$_{1-6}$alkyloxycarbonyl, C$_{1-6}$alkylcarbonyloxy, aminocarbonyl, mono- or di(C$_{1-6}$alkyl)aminocarbonyl, C$_{1-6}$alkyl-C(=O)—NH—, C$_{1-6}$alkyloxy-C(=O)—NH—, H$_2$N—C(=O)—NH— or mono- or di(C$_{1-4}$alkyl)amino-C(=O)—NH—;

Het$^1$ is a saturated 6-membered heterocycle selected from piperidinyl, morpholinyl, thiomorpholinyl, piperazinyl, wherein said saturated 6-membered heterocycle may optionally be substituted with amino or C$_{1-4}$alkyl optionally substituted with aryl;

aryl is phenyl, optionally substituted with up to five substituents each independently selected from halo, hydroxy, C$_{1-6}$alkyl, polyhaloC$_{1-6}$alkyl, C$_{1-6}$alkyloxy, C$_{1-6}$alkylthio, cyano, nitro, amino, mono- or di(C$_{1-6}$alkyl)amino.

2. The compound of claim 1 wherein Q is C$_{3-6}$cycloalkyl, phenyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxyl; azido; amino; mono- or di(C$_{1-6}$alkyl)-amino; C$_{1-6}$alkylcarbonylamino; C$_{1-6}$alkyl; C$_{2-6}$alkenyl; C$_{2-6}$alkynyl; C$_{3-6}$cycloalkyl; C$_{1-6}$alkyl substituted with hydroxy, C$_{1-6}$alkyloxy, amino, mono- or di(C$_{1-4}$alkyl)amino; C$_{1-6}$alkyloxy; C$_{1-6}$alkylthio; C$_{1-6}$alkylcarbonyl; C$_{1-6}$alkyloxycarbonyl; arylC$_{1-6}$alkyloxy; aryloxy; polyhaloC$_{1-6}$alkyl; polyhalo-C$_{1-6}$alkyloxy; polyhaloC$_{1-6}$alkylcarbonyl; C$_{1-4}$alkyl-S(=O)$_n$— or R$^1$HN—S(=O)$_n$—;

or

Q is a radical of formula

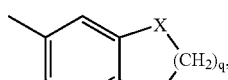

(b-1)

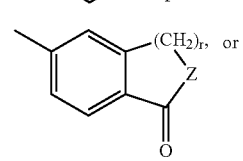

(b-2)

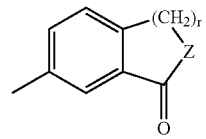

(c-3)

wherein X and Y each independently are O, NR$^3$, CH$_2$ or S, with R$^3$ being hydrogen or C$_{1-4}$alkyl;

q is an integer with value 1 to 4;

Z is O or NR$^4$ with R$^4$ being hydrogen or C$_{1-4}$alkyl;

r is an integer with value 1 to 3;

Z is halo; $C_{1-6}$alkyl; $C_{1-6}$alkyl substituted with hydroxy, carboxyl, cyano, amino, mono- or di($C_{1-6}$alkyl)amino, aminocarbonyl, mono- or di($C_{1-6}$alkyl)aminocarbonyl, $C_{1-6}$alkyloxycarbonyl, $C_{1-6}$alkyloxy; polyhalo$C_{1-4}$alkyl; cyano; amino; aminocarbonyl; mono- or di($C_{1-6}$alkyl)aminocarbonyl; $C_{1-6}$alkyloxycarbonyl; $C_{1-6}$alkylcarbonyloxy; aminoS(=O)$_2$—; mono- or di($C_{1-6}$alkyl)aminoS(=O)$_2$; —C(=N—R$^x$)NR$^y$R$^z$;

L is phenyl, substituted with up to 4 substituents each independently being selected from halo, hydroxy, mercapto, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, H$_2$N—C(=O)—NH—, mono- or di($C_{1-4}$alkyl)amino-C(=O)—NH— or Het-NH—, —C(=N—R$^x$)NR$^y$R$^z$; or L is a monocyclic 5 or 6-membered partially saturated or aromatic heterocycle or a bicyclic partially saturated or aromatic heterocycle wherein each of said ring systems may optionally be substituted with up to 3 substituents, each substituent independently being selected from halo, hydroxy, mercapto, amino, cyano, carboxyl, mono- or di($C_{1-6}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkylthio, $C_{1-6}$alkyloxycarbonyl, $C_{1-6}$alkylcarbonyloxy, aminocarbonyl, mono- or di($C_{1-6}$ alkyl)aminocarbonyl, $C_{1-6}$alkyl-C(=O)—NH—, $C_{1-6}$alkyloxy-C(=O)—NH—, H$_2$N—C(=O)—NH—, mono- or di($C_{1-4}$alkyl)amino-C(=O)—NH— or Het-NH—, —C(=N—R$^x$)NR$^y$R$^z$.

3. A compound of claim 1 wherein L is furanyl, pyrrolyl, oxazolyl, imidazolyl, pyrazolyl, isothiazolyl, oxadiazolyl, triazolyl, thiadiazolyl, a 5-membered partially saturated heterocycle, a 6-membered partially saturated or aromatic heterocycle or a bicyclic partially saturated or aromatic heterocycle wherein each of the aforesaid ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; H$_2$N—C(=O)—NH—; mono- or di($C_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z provided L is other than optionally substituted quinoxalinyl.

4. The compound of claim 1 wherein L is a 6-membered partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; H$_2$N—C(=O)—NH—; mono- or di($C_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z.

5. The compound of claim 1 wherein Q is phenyl, pyridyl, pyrrolyl, pyrazolyl or thienyl, wherein each of said ring systems may optionally be substituted with one or two substituents each independently being selected from halo or polyhalo$C_{1-6}$alkyl; Z is $C_{1-6}$alkyl, halo, $C_{1-6}$alkyloxy, aminocarbonyl; L is pyrimidinyl, pyrazolyl, triazolyl or triazinyl, wherein each of said ring systems may optionally be substituted with one or two substituents each independently being selected from amino, $C_{1-6}$alkylcarbonylamino, halo, Het-NH—, hydroxy, $C_{1-6}$alkylthio, $C_{1-6}$alkyloxy, $C_{1-6}$alkyl, $C_{1-12}$alkylamino, mono- or di(hydroxy$C_{1-12}$alkyl)amino wherein $C_{1-12}$alkyl may further optionally be substituted with hydroxy, Het$^1$, aminocarbonyl, cyano, amino$C_{1-12}$alkylamino, hydroxy$C_{1-12}$alkyloxy, —NH—C(=NH)—NH$_2$, carboxy$C_{1-12}$alkylamino or amino$C_{1-6}$alkyloxy$C_{1-6}$alkylamino.

6. The compound of claim 1 provided that

L is other than substituted phenyl;

when Z is methyl, Q is phenyl or phenyl substituted with halo, methyl or ethyloxy, then L is other than quinoxalinyl;

when Z is methyl, Q is phenyl or phenyl substituted at the para position with methyl, chloro, nitro or methyloxy, then L is other than thiazolyl substituted with methyl or amino;

when Z is trifluoromethyl, Q is 4-methylphenyl, then L is other than 1,2,3-triazolyl mono- or disubstituted with methyloxycarbonyl;

L is other than unsubstituted or substituted benzoxazolyl or unsubstituted or substituted benzimidazolyl;

the compound is other than

| L | Z | Q |
|---|---|---|
| 2,4-dimethylquinolin-?-yl (quinoline with CH$_3$ at 2 and 4) | CH$_3$— | phenyl |
| 3-pyridyl | CH$_3$— | 4-pyridyl |
| 4-chloro-2-methylquinolin-?-yl | CH$_3$—C(=O)—O— | phenyl |

-continued
| L | Z | Q |
|---|---|---|
| 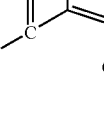 | CH₃— | 4-chloro-phenyl |
| 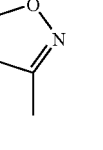 | CH₃— | phenyl |
|  | —CF₃ | 4-methyl-phenyl |
|  | —CH₂—C(=O)—O—CH₂CH₃ | 4-chloro-phenyl |
| 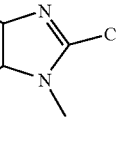 | —CF₃ | phenyl |
| 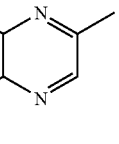 | CH₃— | phenyl |
| 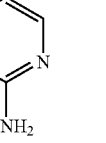 | CH₃— | 4-chlorophenyl |
| 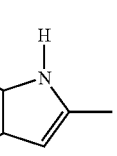 | CH₃— | phenyl |
| 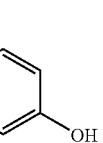 | CH₃— | 2-thienyl |

-continued

| L | Z | Q |
|---|---|---|
| 4-hydroxyphenyl (para-OH phenyl) | F— | 4-(hexyl)phenyl, -(CH₂)₅—CH₃ |
| 4-methyl-5-(methylthio)-4H-1,2,4-triazol-3-yl | CH₃— | phenyl |
| 4-methyl-2-(methylthio)pyrimidin-... yl | CH₃— | 4-chlorophenyl. |

7. The compound of claim 1 provided that

L is other than substituted phenyl;

when Z is methyl, Q is phenyl or phenyl substituted with halo, CH₃ or ethyloxy, then L is other than quinoxalinyl;

when Z is methyl, Q is phenyl or phenyl substituted at the para position with methyl, chloro, nitro or methyloxy, then L is other than thiazolyl substituted with methyl or amino;

the compound is other than

| L | Z | Q |
|---|---|---|
| 3-pyridyl | CH₃— | 4-pyridyl |
| 2-methyl-4-methyl-5-(methoxycarbonyl)thiazolyl | CH₃— | 4-chloro-phenyl |
| 5-amino-3-methyl-isoxazolyl | CH₃— | phenyl |
| 3-methylthiophen-... yl | —CH₂—C(=O)—O—CH₂CH₃ | 4-chloro-phenyl |
| 3-methylquinoxalin-2-yl | CH₃— | phenyl |
| 4-hydroxyphenyl | F— | 4-(hexyl)phenyl, -(CH₂)₅—CH₃. |

8. A pharmaceutical composition comprising a pharmaceutically acceptable carrier and as active ingredient a therapeutically effective amount of the compound of claim 1.

9. A compound of formula

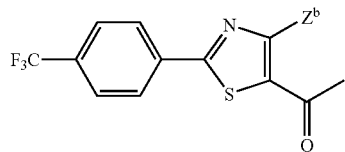

(IX-c)

wherein $Z^b$ represents halo or $C_{1-4}$alkyl.

10. A compound of formula

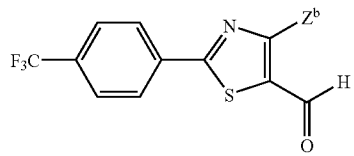

(XIII-b)

wherein $Z^b$ represents halo or $C_{1-4}$alkyl.

11. A process of preparing a compound as claimed in claim 6 characterized by a) reacting an intermediate of formula (II) with an intermediate of formula (III) or a suitable salt thereof, in the presence of a suitable solvent and a suitable alcoholate

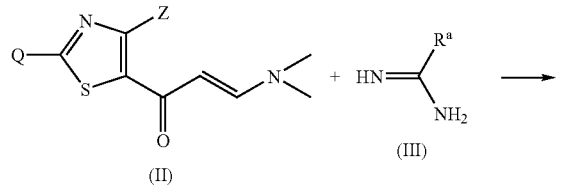

(II)      (III)

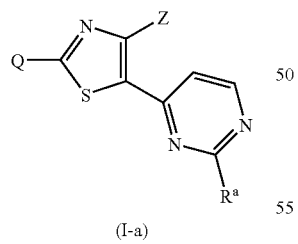

(I-a)

with Q and Z as defined in claim 1 and $R^a$ representing hydrogen, amino, optionally substituted $C_{1-6}$alkyl, optionally substituted mono- or di($C_{1-12}$alkyl)amino, Het-NH— or Het$^1$;

b) reacting an intermediate of formula (II') with an intermediate of formula (III) or a suitable salt thereof, in the presence of a suitable solvent and a suitable alcoholate,

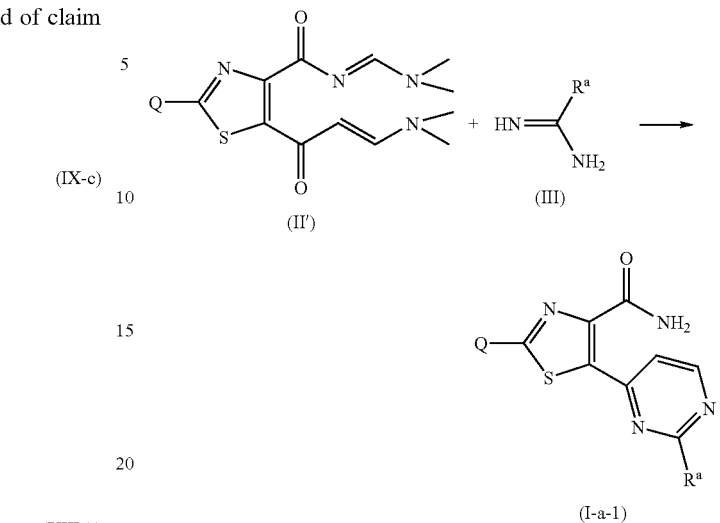

(II')      (III)

(I-a-1)

with Q as defined in claim 1 and $R^a$ representing hydrogen, amino, optionally substituted $C_{1-6}$alkyl, optionally substituted mono- or di($C_{1-12}$alkyl)amino, Het-NH— or Het$^1$;

c) reacting an intermediate of formula (IV) or (IV') with an intermediate of formula (V) optionally at elevated temperature and optionally in the presence of a suitable solvent, and optionally in the presence of a suitable base or a suitable acid, and optionally under pressure

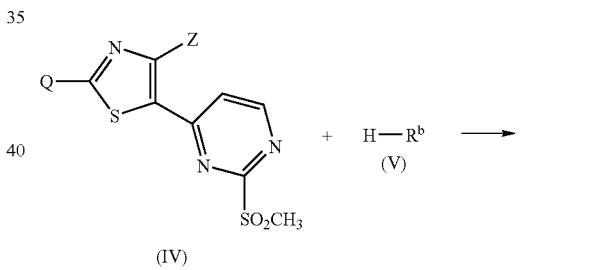

(IV)      (V)

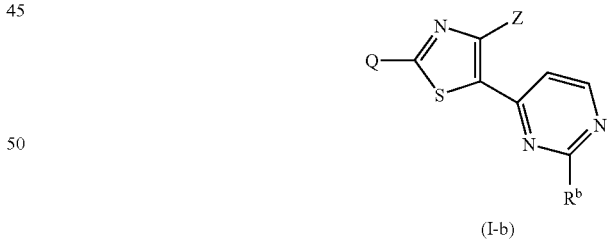

(I-b)

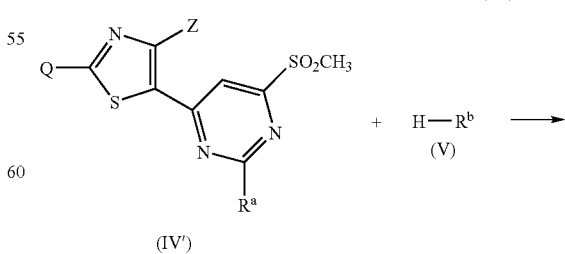

(IV')

-continued

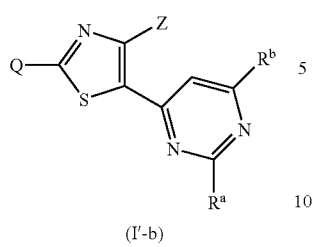
(I'-b)

with Q and Z as defined in claim 1, $R^a$ representing hydrogen, amino, optionally substituted $C_{1-6}$alkyl, optionally substituted mono- or di($C_{1-12}$alkyl)amino, Het-NH— or Het[1], and $R^b$ representing —NH$_2$, Het[1]-NH—; Het[1]; —NH—C(=NH)—N($R^z$)$_2$; $C_{1-12}$alkyloxy optionally substituted with one, two or three hydroxy groups; optionally substituted mono- or di($C_{1-12}$alkyl)amino, in particular unsubstituted mono- or di($C_{1-12}$alkyl)amino or mono- or di($C_{1-12}$alkyl)amino wherein $C_{1-12}$alkyl is substituted with one, two or three substituents selected from hydroxy, carboxyl, amino, amino$C_{1-4}$alkyloxy$C_{1-4}$alkyloxy;

d) reacting an intermediate of formula (IV) with a suitable cyanide salt in the presence of a suitable solvent

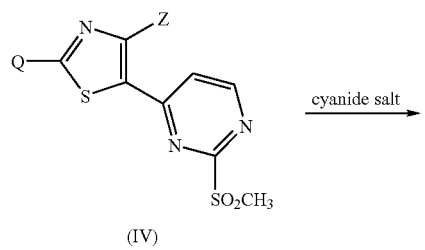

with Q and Z as defined in claim 1;

e) reacting an intermediate of formula (IV) with a suitable hydroxide base in the presence of a suitable solvent

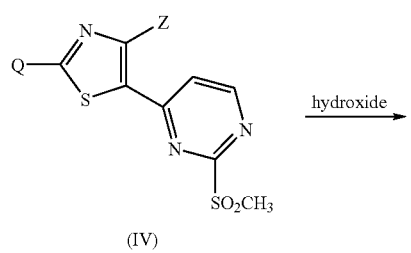

with Q and Z as defined in claim 1;

f) reacting an intermediate of formula (II) with thiourea in the presence of a suitable solvent, a suitable alcoholate, dimethyl sulphate, and a suitable base

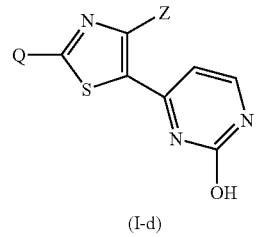

(I-d)

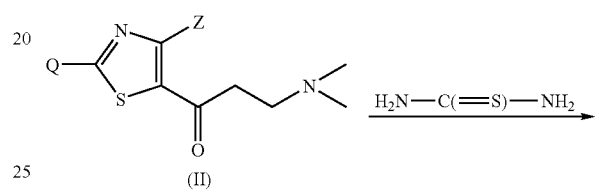

with Q and Z as defined in claim 1;

g) reacting an intermediate of formula (XXXVI) with an intermediate of formula (III) in the presence of a suitable solvent

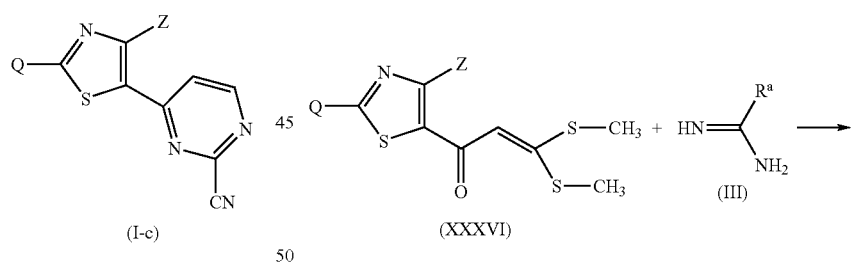

with Q and Z as defined in claim 1 and $R^a$ as defined above in process variant a) and b);

h) reacting an intermediate of formula (II) with hydrazine monohydrate in the presence of a suitable acid

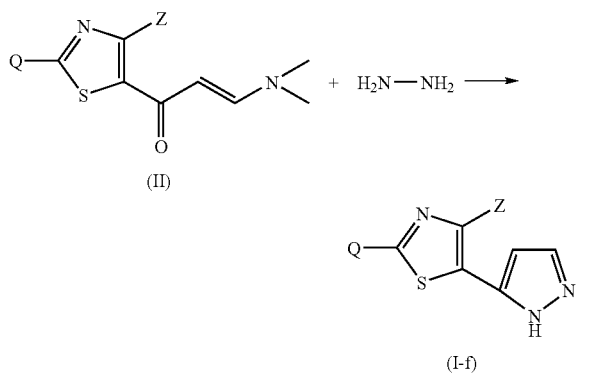

with Q and Z as defined in claim 1;

i) reacting an intermediate of formula (VII) with an intermediate of formula (VIII) in the presence of a suitable base and a suitable solvent

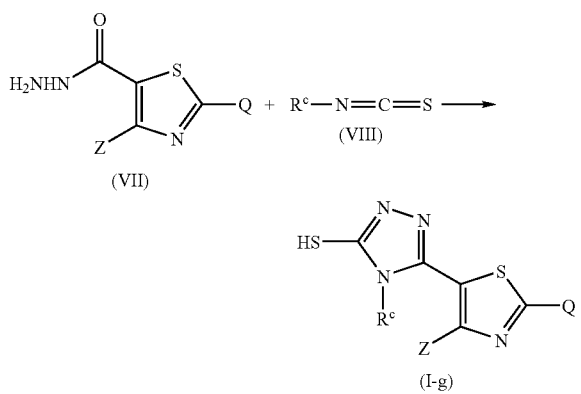

with Q and Z as defined in claim 1 and $R^c$ representing hydrogen or $C_{1-6}$alkyl;

j) reacting an intermediate of formula (VI) with an intermediate of formula (III) or a suitable salt thereof, in the presence of a suitable solvent

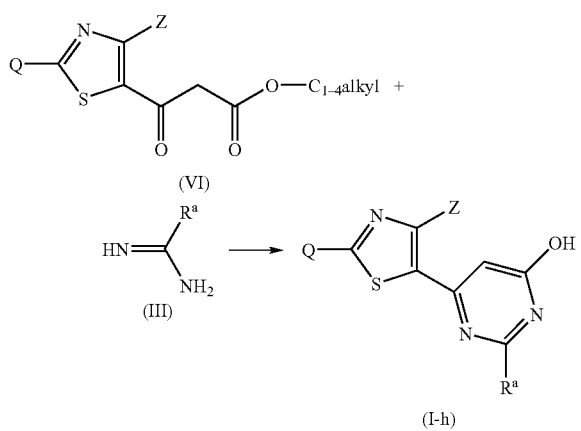

with Q and Z as defined in claim 1 and $R^a$ as defined above in process variant a) and b);

k) reacting an intermediate of formula (XXX) with an intermediate of formula (III) or a suitable salt thereof, in the presence of 1,1-dimethoxy-N,N-dimethyl-methanamine and in the presence of a suitable solvent

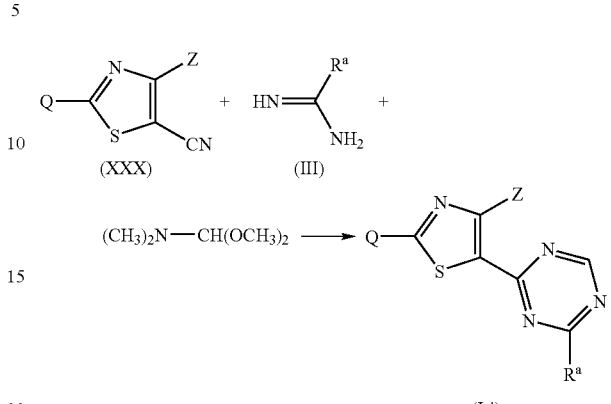

with Q and Z as defined in claim 1 and $R^a$ as defined above in process variant a) and b);

and, if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, quaternary amines or N-oxide forms thereof.

12. A product comprising (a) a compound as defined in claim 6, and (b) another anti-inflammatory or immunosuppressive compound, as a combined preparation for simultaneous, separate or sequential use in the treatment of inflammatory or autoimmune diseases.

13. A pharmaceutical composition comprising a pharmaceutically acceptable carrier and as active ingredients (a) a compound as defined in claim 6, and (b) another anti-inflammatory or immunosuppressive compound.

14. A compound of claim 2 wherein L is furanyl, pyrrolyl, oxazolyl, imidazolyl, pyrazolyl, isothiazolyl, oxadiazolyl, triazolyl, thiadiazolyl, a 5-membered partially saturated heterocycle, a 6-membered partially saturated or aromatic heterocycle or a bicyclic partially saturated or aromatic heterocycle wherein each of the aforesaid ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH—; $Het^1$-NH—; —NH—C(=N—$R^x$)$NR^yR^z$; —C(=N—$R^x$)$NR^yR^z$; $Het^1$; or a radical of formula —X—$C_1$—$Y_1$—$C_2$—$Y_2$—$C_3$—$Y_3$—$C_4$-Z provided L is other than optionally substituted quinoxalinyl.

15. The compound of claim 2 wherein L is a 6-membered partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl;

$C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z.

16. The compound of claim 3 wherein L is a 6-membered partially saturated or aromatic heterocycle wherein each of said ring systems may optionally be substituted with up to 3 substituents, each substituent independently being selected from $C_{1-6}$alkyloxycarbonyl; $C_{1-6}$alkylcarbonyloxy; aminocarbonyl; mono- or di($C_{1-6}$alkyl)aminocarbonyl; $C_{1-6}$alkyl-C(=O)—NH—; $C_{1-6}$alkyloxy-C(=O)—NH—; $H_2N$—C(=O)—NH—; mono- or di($C_{1-4}$alkyl)amino-C(=O)—NH—; Het-NH—; Het$^1$-NH—; —NH—C(=N—R$^x$)NR$^y$R$^z$; —C(=N—R$^x$)NR$^y$R$^z$; Het$^1$; or a radical of formula —X—C$_1$—Y$_1$—C$_2$—Y$_2$—C$_3$—Y$_3$—C$_4$-Z.

17. A pharmaceutical composition comprising a pharmaceutically acceptable carrier and as active ingredient a therapeutically effective amount of the compound of claim 2.

18. A pharmaceutical composition comprising a pharmaceutically acceptable carrier and as active ingredient a therapeutically effective amount of the compound of claim 3.

19. A pharmaceutical composition comprising a pharmaceutically acceptable carrier and as active ingredient a therapeutically effective amount of the compound of claim 4.

20. A pharmaceutical composition comprising a pharmaceutically acceptable carrier and as active ingredient a therapeutically effective amount of the compound of claim 5.

21. A pharmaceutical composition comprising a pharmaceutically acceptable carrier and as active ingredient a therapeutically effective amount of the compound of claim 6.

22. A pharmaceutical composition comprising a pharmaceutically acceptable carrier and as active ingredient a therapeutically effective amount of the compound of claim 7.

23. A pharmaceutical composition comprising a pharmaceutically acceptable carrier and as active ingredient a therapeutically effective amount of the compound of claim 14.

24. A pharmaceutical composition comprising a pharmaceutically acceptable carrier and as active ingredient a therapeutically effective amount of the compound of claim 15.

25. A pharmaceutical composition comprising a pharmaceutically acceptable carrier and as active ingredient a therapeutically effective amount of the compound of claim 16.

26. A product containing (a) a compound as defined in claim 7, and (b) another anti-inflammatory or immunosuppressive compound, as a combined preparation for simultaneous, separate or sequential use in the treatment of inflammatory or autoimmune diseases.

27. A pharmaceutical composition comprising a pharmaceutically acceptable carrier and as active ingredients (a) a compound as defined in claim 7, and (b) another anti-inflammatory or immunosuppressive compound.

* * * * *